(12) United States Patent
Chen-Bettecken

(10) Patent No.: US 7,816,136 B2
(45) Date of Patent: Oct. 19, 2010

(54) METHOD FOR GROWING STEM CELLS ON GENETICALLY MODIFIED SUPPORTER CELLS

(76) Inventor: Yu-hua Una Chen-Bettecken, Biochemistry Institute Friedrichstrasse 24, Giessen (DE) 35392

( * ) Notice: Subject to any disclaimer, the term of this patent is extended or adjusted under 35 U.S.C. 154(b) by 478 days.

(21) Appl. No.: 11/634,373

(22) Filed: Dec. 6, 2006

(65) Prior Publication Data

US 2007/0166293 A1 Jul. 19, 2007

Related U.S. Application Data

(63) Continuation of application No. 09/957,458, filed on Sep. 21, 2001, now abandoned, which is a continuation-in-part of application No. PCT/EP00/08247, filed on Aug. 24, 2000.

(30) Foreign Application Priority Data

Aug. 24, 1999 (EP) .................................. 99116533

(51) Int. Cl.
*C12N 5/02* (2006.01)
(52) U.S. Cl. ........................ 435/373; 435/375; 435/377; 435/455
(58) Field of Classification Search ...................... None
See application file for complete search history.

(56) References Cited

U.S. PATENT DOCUMENTS 5,922,927 A 7/1999 Bujard et al.

FOREIGN PATENT DOCUMENTS

| EP | 0 753 574 A1 | 1/1997 |
|---|---|---|
| WO | WO 97/37009 | 10/1997 |

OTHER PUBLICATIONS

Sturtz et al. Tetracycline-Regulatable Expression Vectorss Tightly Regulate In Vitro Gene Expression of Secreted Proteins. Gene. 1998, vol. 221, pp. 279-285.*
Tao et al. Evidence for Transdifferentation of Human Bone Marrow-Derived Stem Cells: Recent Progress and Controversies. Pathology. 2003, vol. 35, pp. 6-13.*
Manfred Gossen et al., "Tight Control of Gene Expression in Mammalian Cells By Tetracyline-Responsive Promoters", Proc. Natl. Acad. Sci. USA, vol. 89, pges. 5547-5551, Jun. 1992.

* cited by examiner

*Primary Examiner*—Deborah Crouch
(74) *Attorney, Agent, or Firm*—Jacobson Holman PLLC

(57) ABSTRACT

A method for growing stem cells comprising the steps of a
providing stem cells with supporters said supporters being genetically modified in order to provide externally regulatable interactions between the supporters and the stem cells; supporters and stem cells are interchangeable upon genetic modification and interaction;
applying an external signal for starting or stopping the interactions.

9 Claims, 56 Drawing Sheets

Cloning of growth factor genes
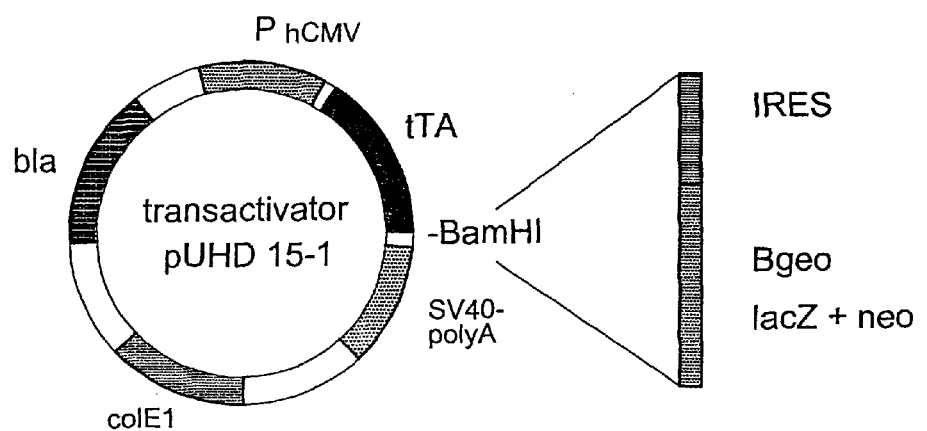
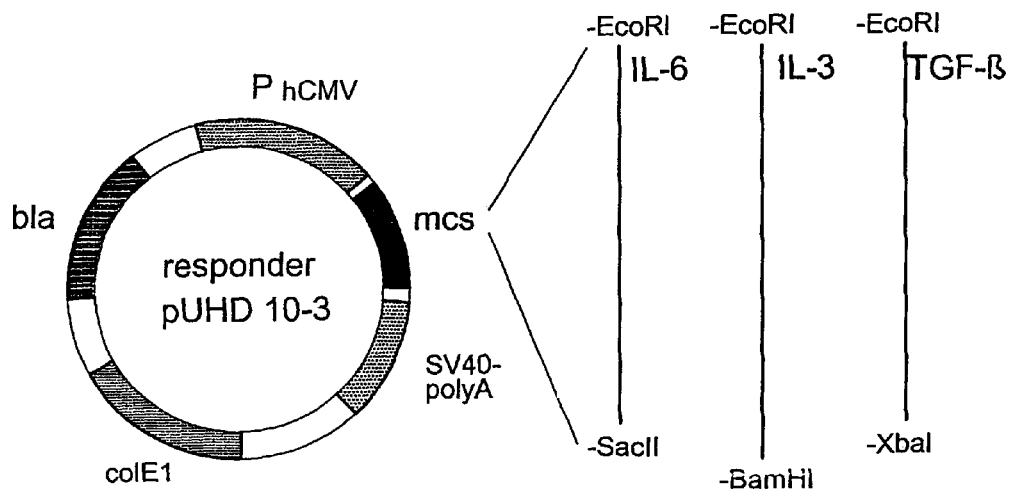
FIG.4

A.MK(MK+H3-GFP) 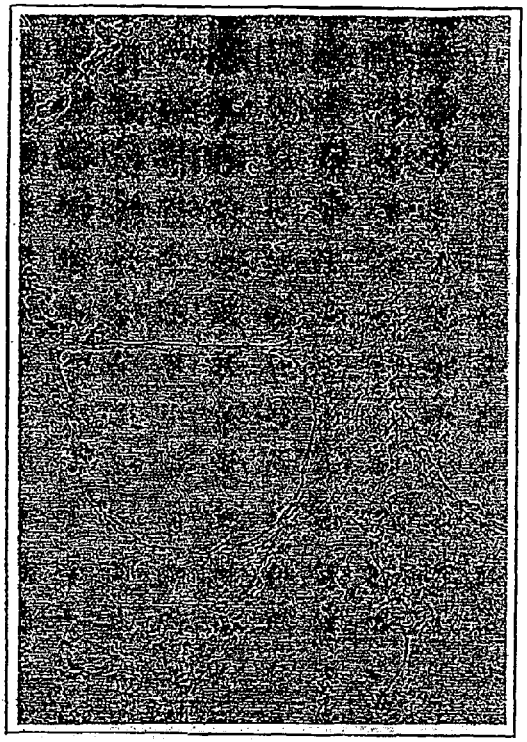 B.H3-GFP(MK+H3-GFP 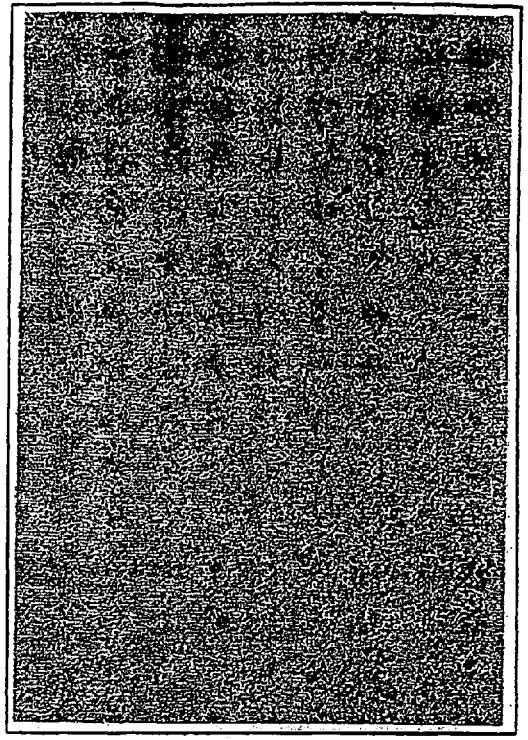
C.MK alone 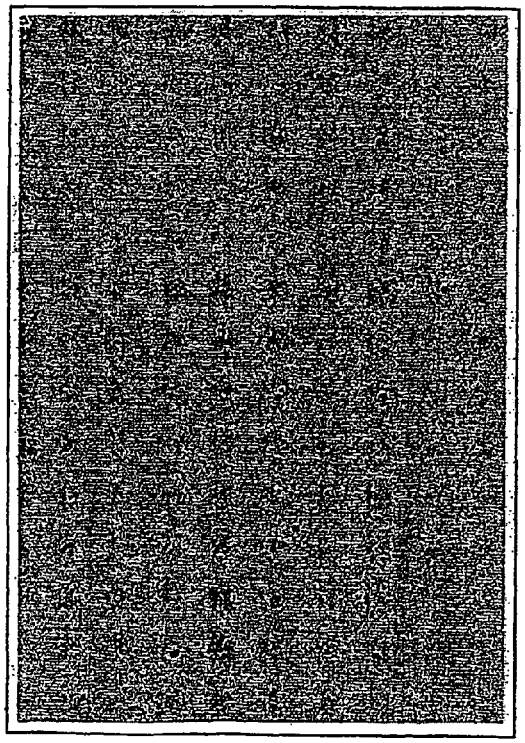 D.H3-GFP alone 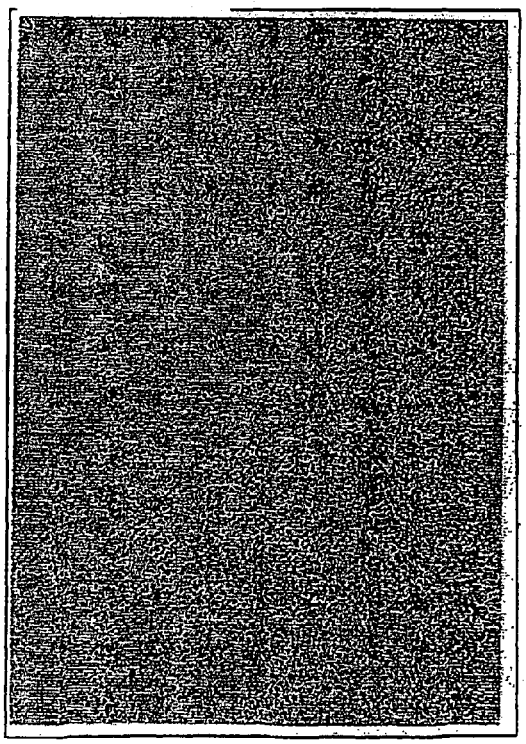
FIG.7

A. MK (MK+H3-GFP-hIL6)
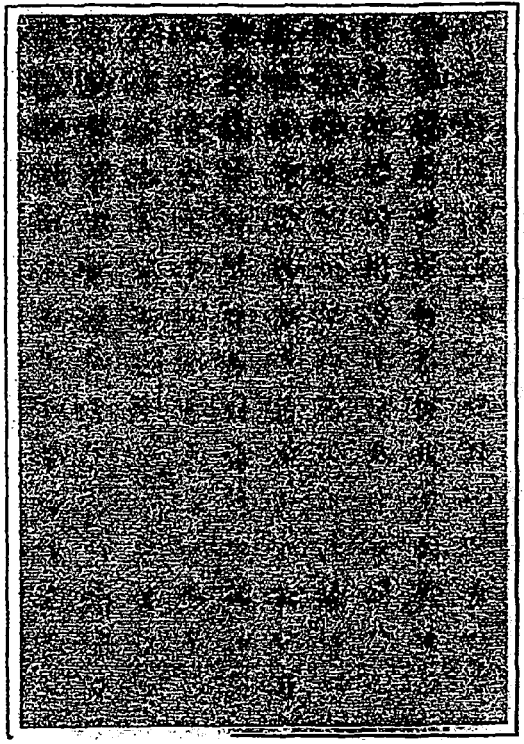
B. H3-GFP-hIL6(MK+H3-GFP-hIL6)
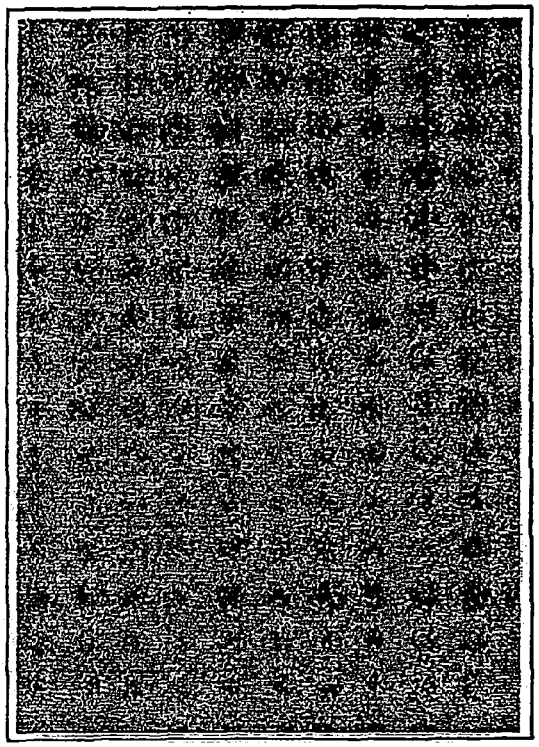
C. MK alone
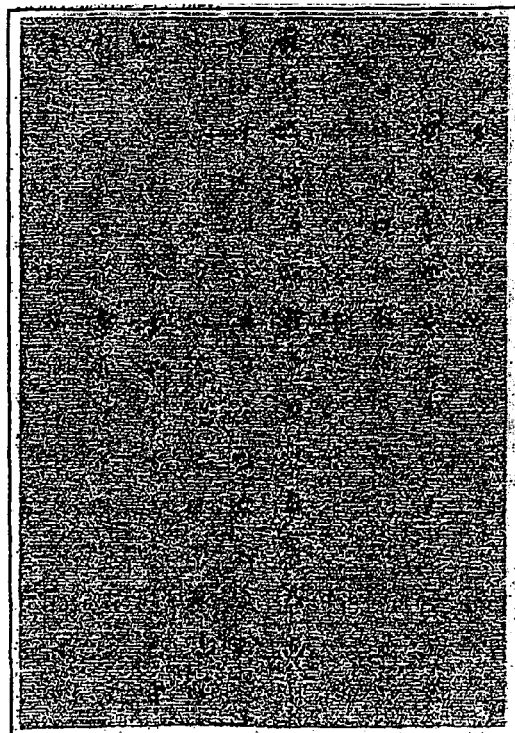
D. H3-GFP-hIL6 alone
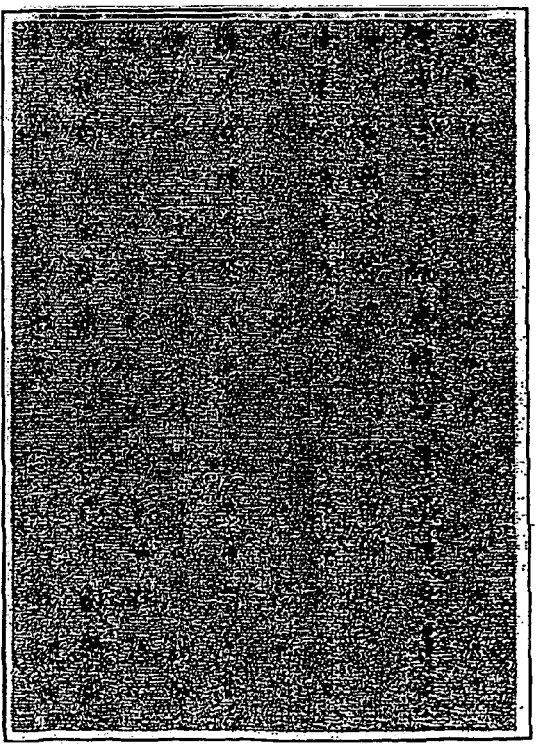
FIG. 8

A.MK (MK+H3-LC)
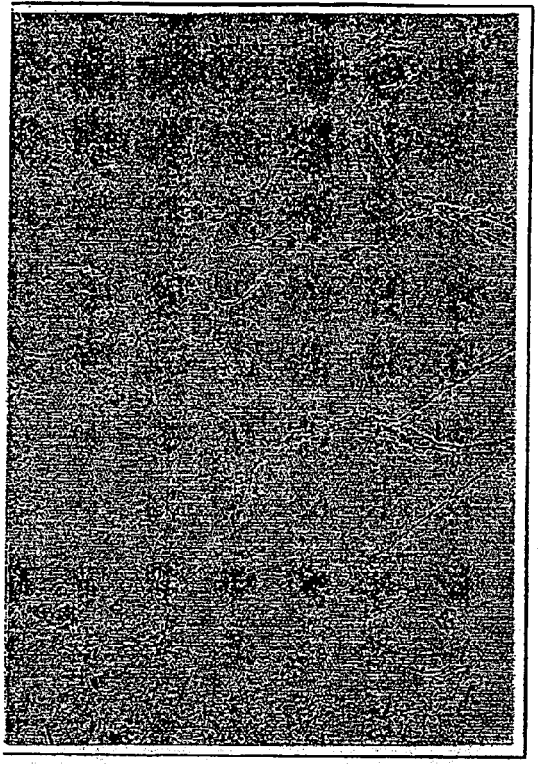
B.H3-LC (MK+H3-LC)
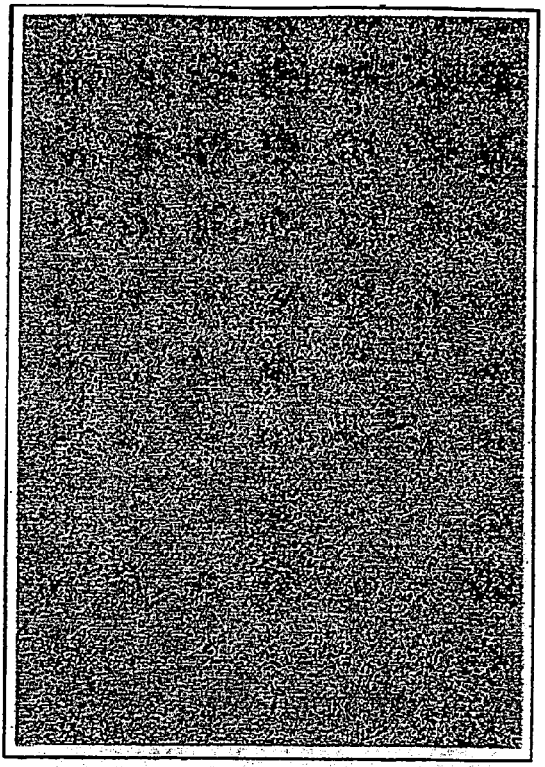
C.MK alone
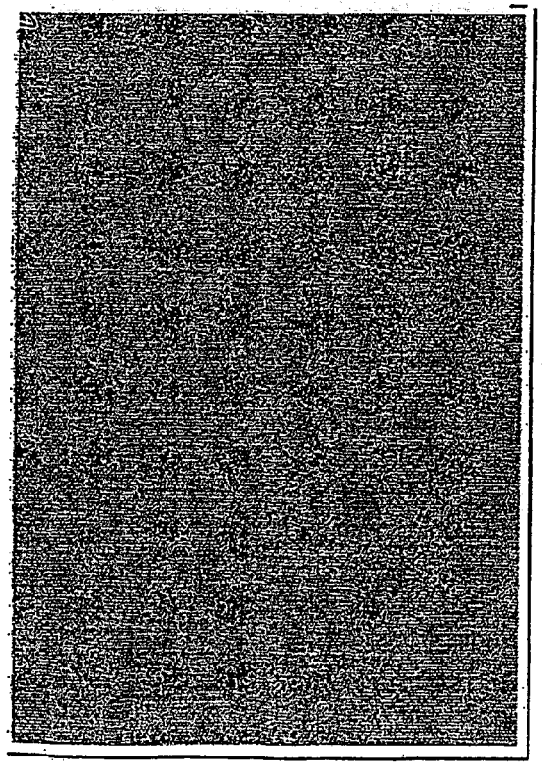
D.H3-LC alone
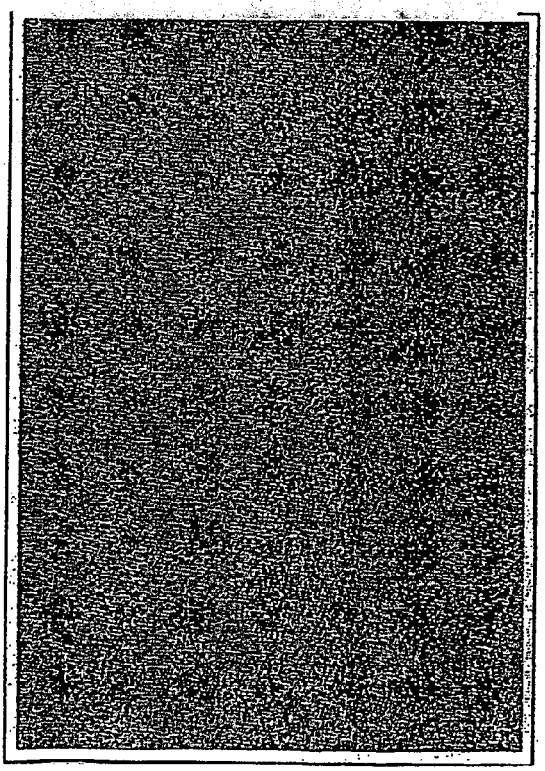
FIG.9

A.Sk (Sk+H3-GFP)    B.H3-GFP (Sk+H3-GFP)
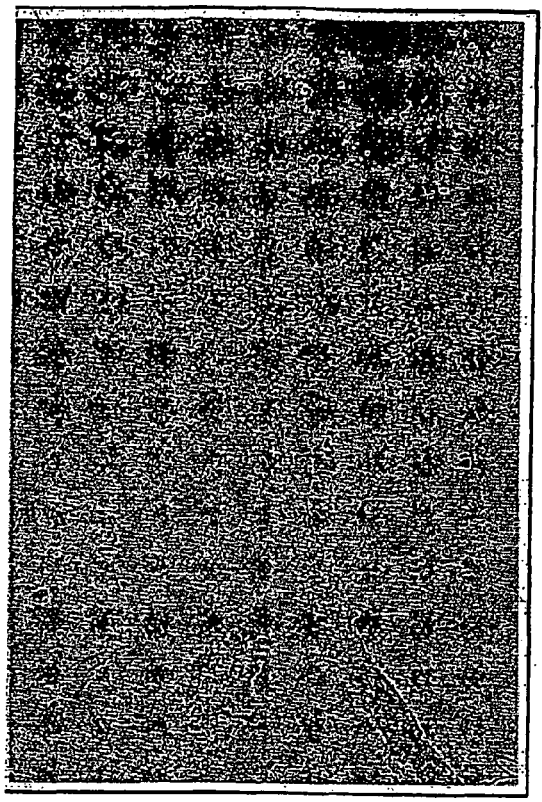 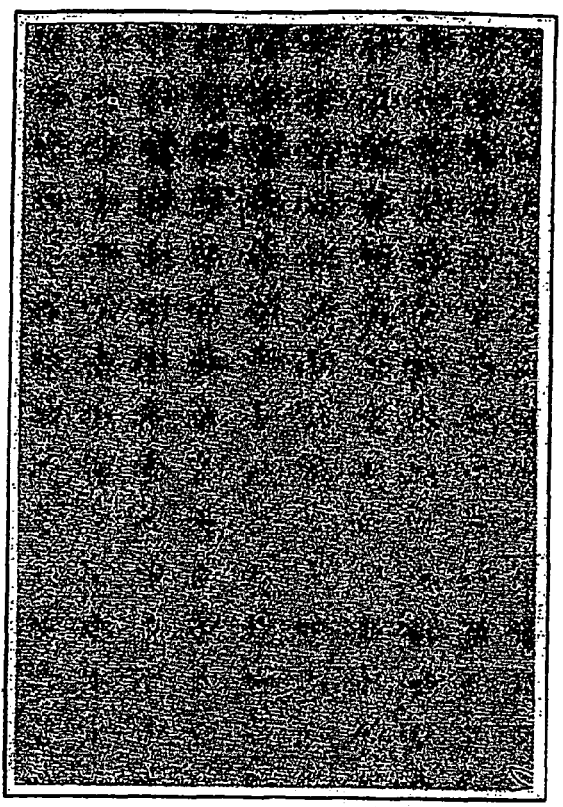
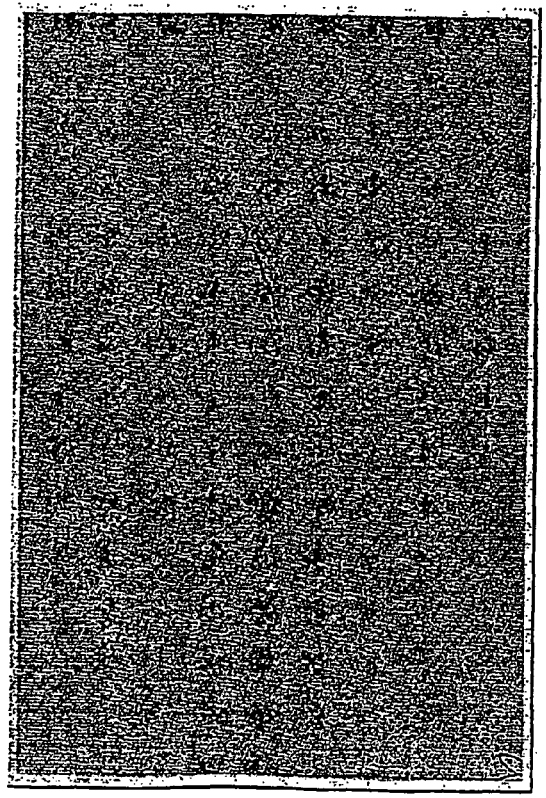 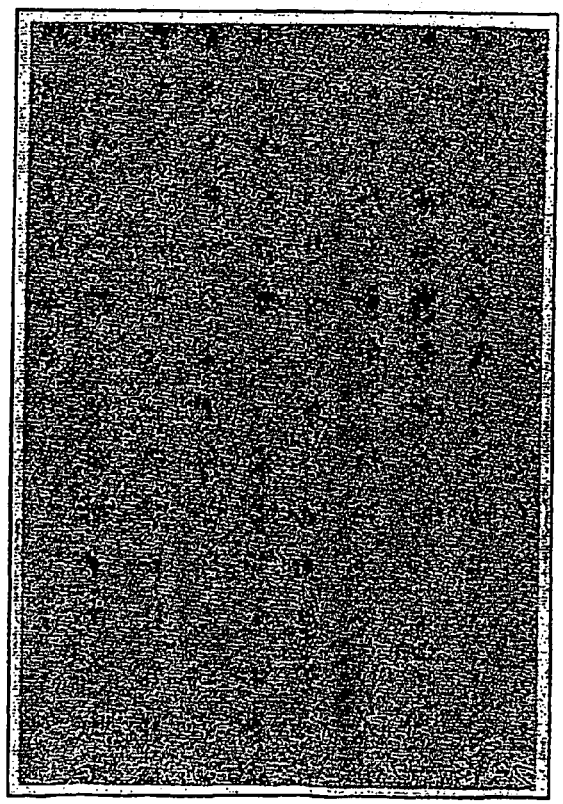
C.Sk alone    D.H3-GFP alone
FIG.10

A. SK (Sk+H3-GFP-hIL6)   B. H3-GFP-hIL6 (Sk+H3-GFP-hIL6)
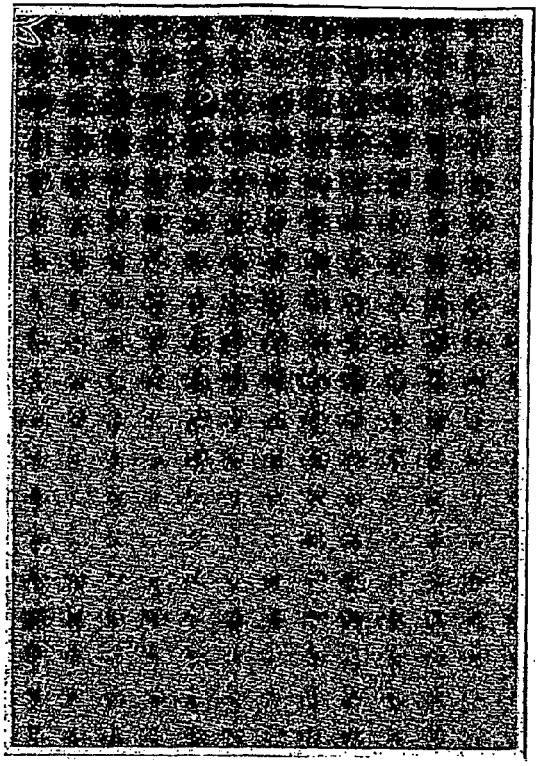 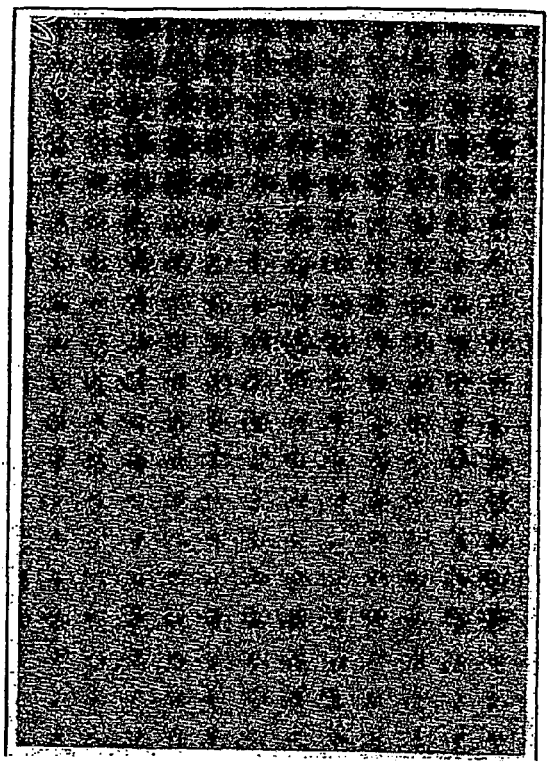
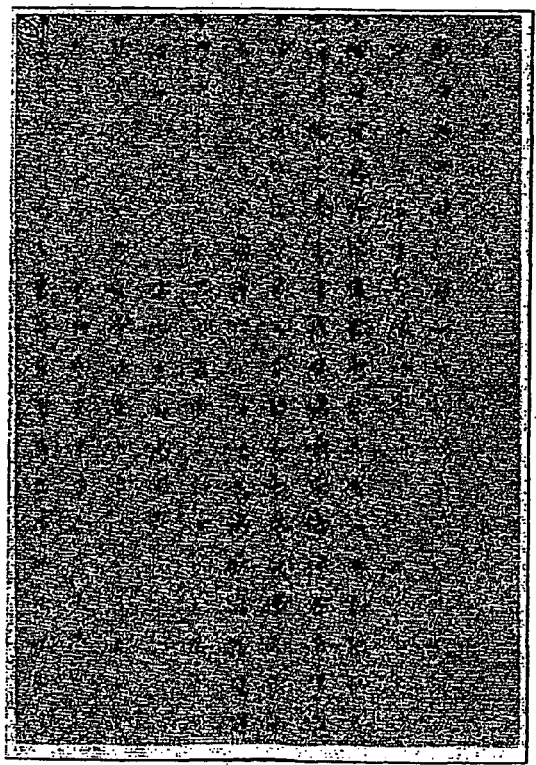 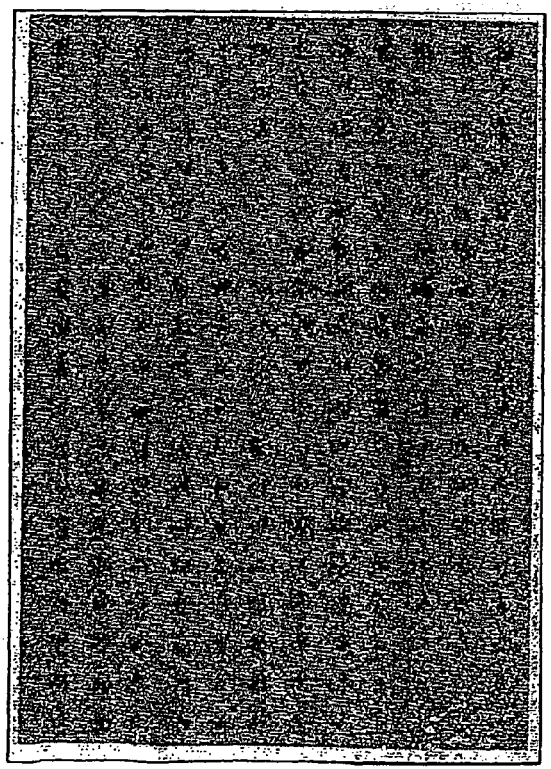
C. Sk alone   D. H3-GFP-hIL6 alone
FIG. 11

A. Sk (Sk+H3-LC) 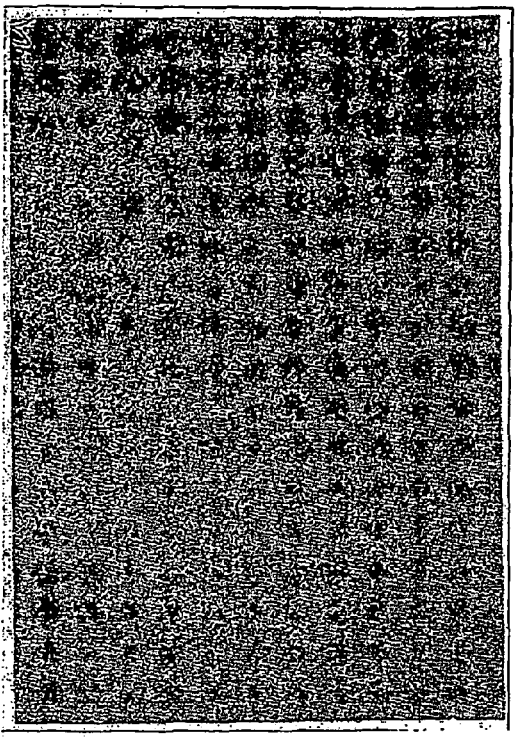 B. H3-LC (Sk+H3-LC) 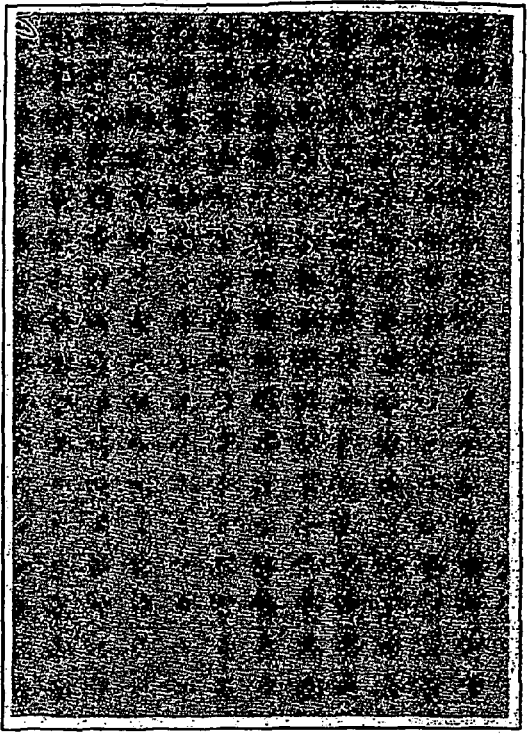
C. Sk alone 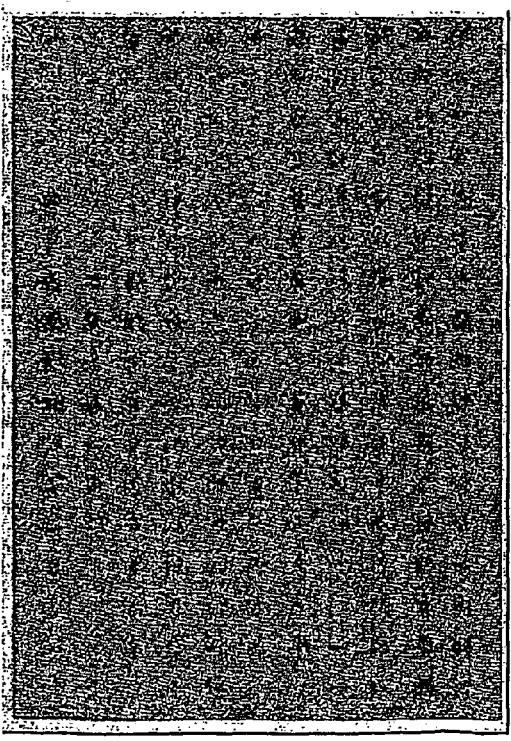 D. H3-LC alone 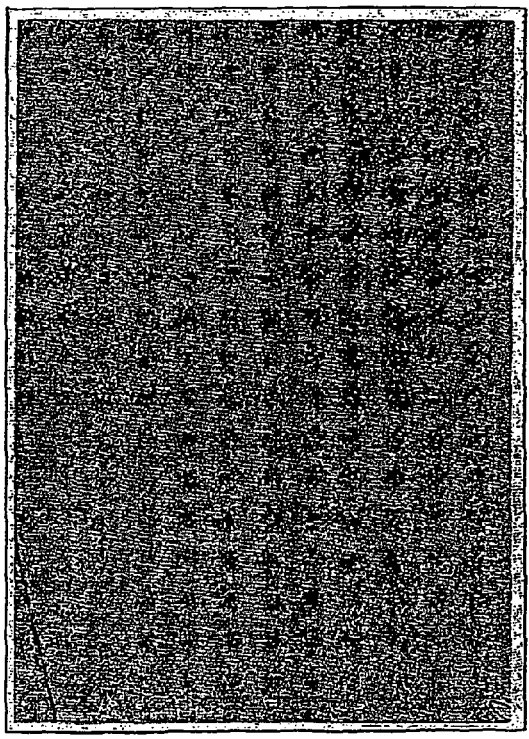
FIG.12

A. Sk (Sk+MK) 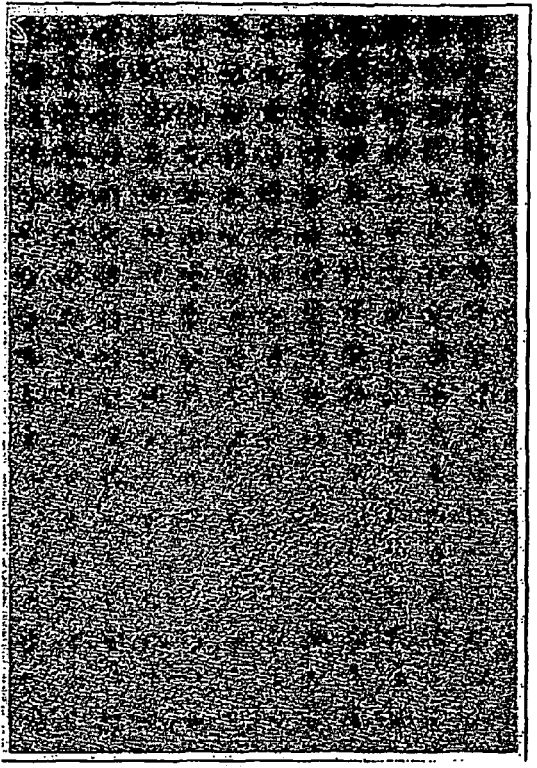 B. MK (Sk+MK) 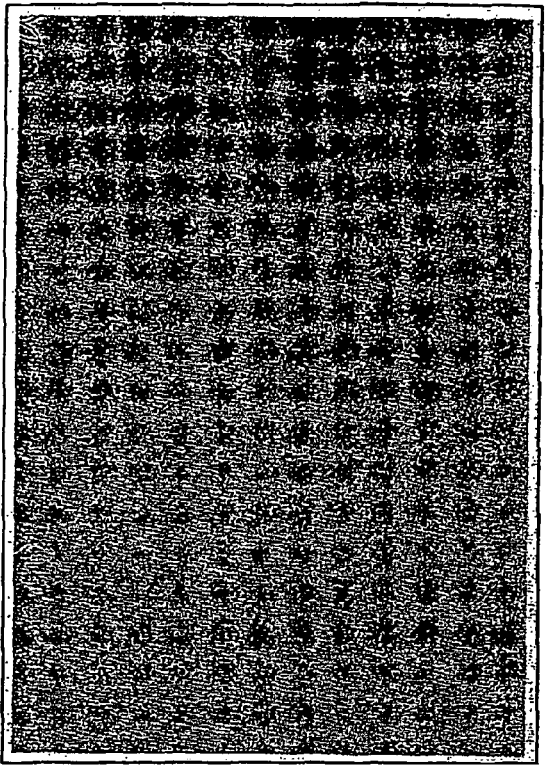
C. Sk alone 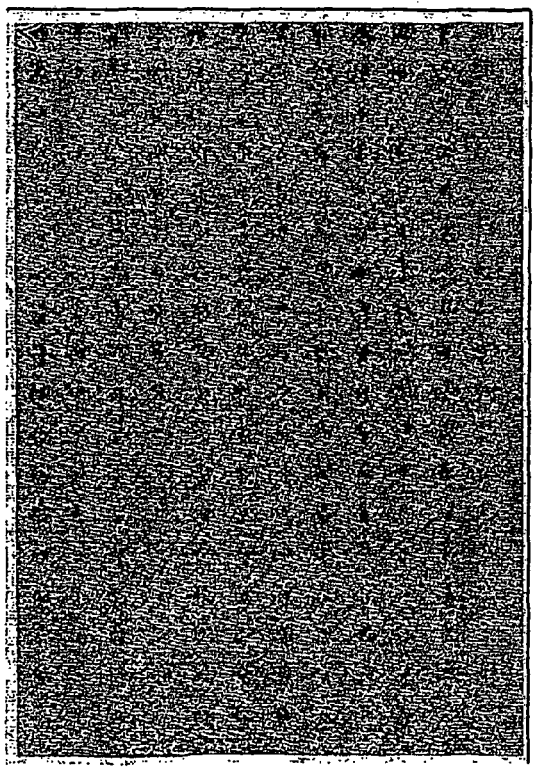 D. MK alone 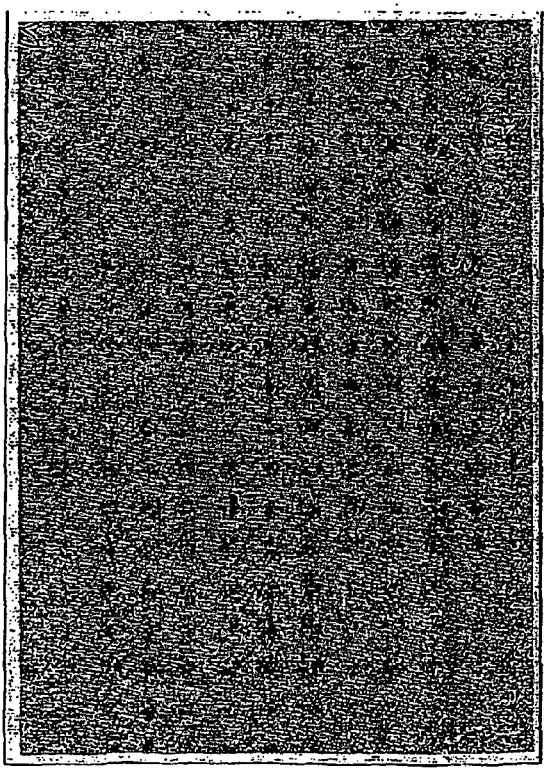
FIG.13

A. Lg (Lg+L14-hIL3)
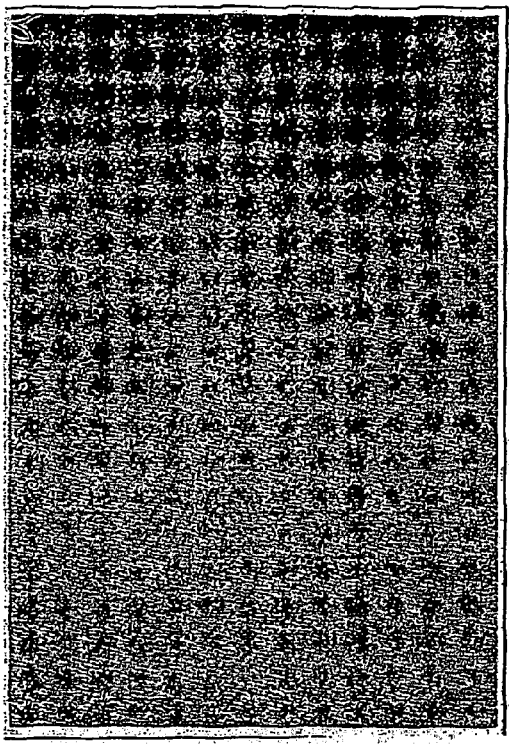
B. L14-hIL3 (Lg+L14-hIL3)
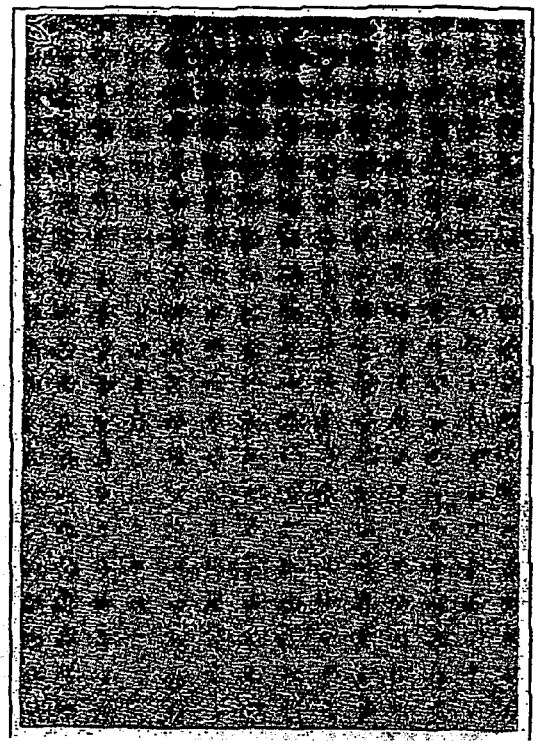
C. Lg alone
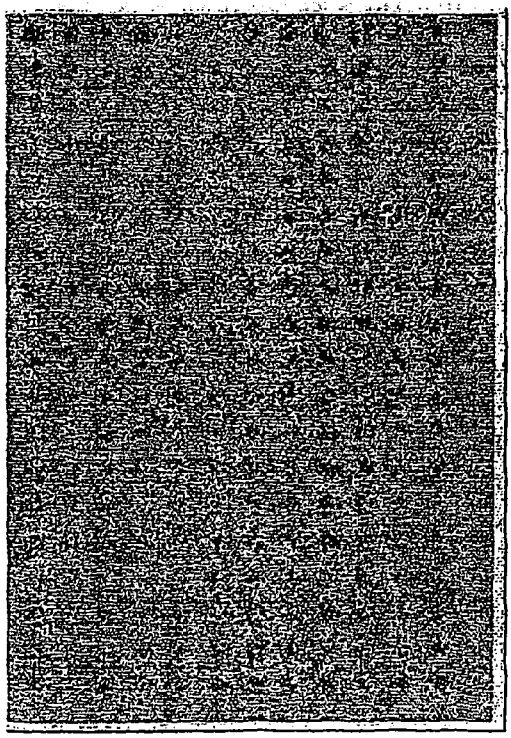
D. L14-hIL3 alone
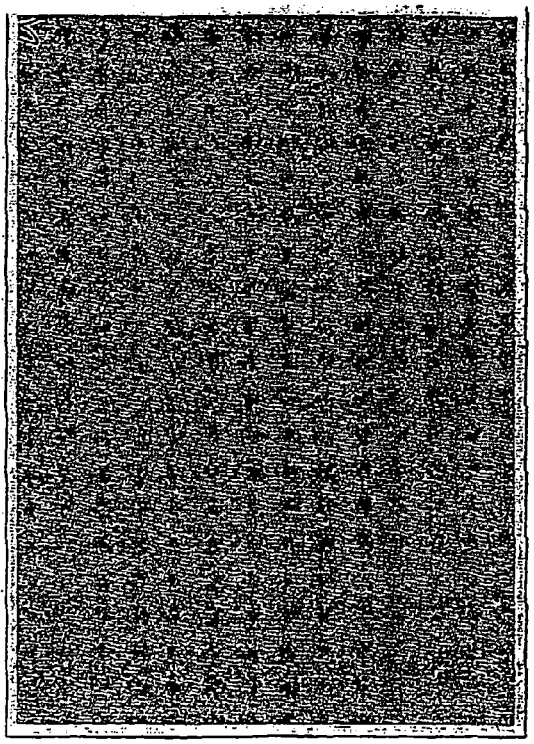
FIG.15 pD12JCVPlong-hCNTF

Length: 7969  July 22, 1999

```
   1 GCTAGCGATT TAGGTGACAC TATAGAATAG ATCtcgacnn nGTCACCCCT
  51 AGAGTCGAGC TGTGACGGTC CTTACAATGA AATGCANCTG GGTTATCTTC
 101 TTCCTGATGG CAGGGGTTAC AGGTAAGGGG CTCCCAAGTC CAAACTTGA
 151 GGGTCCATAA ACTCTGTGAC AGTGGCAATC ACTTTGCCTT TCTTTCTACA
 201 GGGGTGAATT CGGCTTTCAC AGAGCATTCA CCGCTGACCC CTCACCGTCG
 251 GGACCTCTGT AGCCGCTCTA TCTGGCTAGC AAGGAAGATT CGTTCAGACC
 301 TTGACTGCTC TTACGGAATC CTATGTAAGT TGCCTATTTT GCTGTTATCT
 351 GTTTTCCCTT CATCTTTTTT GATCCAGCAA CTTACCATCA CGCATCAGCT
 401 CCATTACCAA TTGTGAAAGC TCTAATCATA TAGTCATTCA TATAGGTTAT
 451 TTGACATGGG CCCTTCCCTT GAGGAAACCC ATGTGACTTT ATTTTCTTCC
 501 TCTGGGCTGT TTAGGAGATG AAGTTACTTG AATGAGAAAA TATATATGGA
 551 GTTCTAGAAA GGATTGGTTT ATATGTCTTG GAGGCTATTT CAAAATTTAT
 601 TTGGCCATAT ATTCTGAATA CTACCTAGAA CAGATTAGCC ATGGGCCCTN
 651 TGGGTTNTTC ATAAGCCATT GTTCTGAANT TTTTTAGCTT TGTAAATGAA
 701 AGGTTTATGG GATAGGAAGA GTNCTATGAA CGTGGGAGGA ATTTGTAAAT
 751 CCTACCAATT TNTNCTATAT AGCATTAGCC CCCACCTTTT ANTATTCTGC
 801 ATCAAAAGTA AGATTGTGTC TAAAGAGAAA GGTNAGCTAT CAAAAGGACT
 851 CCTATAANAT TCNTTGGAAA CTTNTGGAAN TGTCAAATTT NTTTGAGCTA
 901 ATTNTTGGAG TTCCAAANTT TGTCTTNTNA CAGTNAAGGG GGANCCCCAT
 951 TCANATTTNC CCCCCTNNNG ANAATGCTTG GGGGAAAAAA CCTNCCAACC
1001 CCNTTGTGGG ANGAAGTTTT TTTAANNTTT TAAGGCTNGN NGAAACNGGN
1051 TTTTAATTTT TTGGGNCNAN CGCCTNTCCC CGGTACCAGG AAAATCAGGA
1101 CCTNTTTTTG GGGNNGNGCN CCNACNGGGG GGNAAAANGG GAAATTTCNT
1151 CANAAAAAAT CTTTTCCGnn nnnngtgaag catcagggcc tgaacaagaa
1201 catcaacctg gactctgcgg atgggatgcc agtggcaagc actgatcagt
1251 ggagtgagct gaccgaggca gagcgactcc aagagaacct tcaagcttat
1301 cgtaccttcc atgttttgtt ggccaggctc ttagaagacc agcaggtgca
```

Fig. 18-a

```
1351  ttttacccca accgaaggtg acttccatca agctatacat acccttcttc
1401  tccaagtcgc tgcctttgca taccagatag aggagttaat gatactcctg
1451  gaatacaaga tcccccgcaa tgaggctgat gggatgccta ttaatgttgg
1501  agatggtggt ctctttgaga agaagctgtg gggcctaaag gtgctgcagg
1551  agctttcaca gtggacagta aggtccatcc atgaccttcg tttcatttct
1601  tctcatcaga ctgggatccc agcacgtggg agccattata ttgctaacaa
1651  caagaaaatg tagnnnnngc ggccTGCGCC GTCTTTCCCG ACGTTAAAGG
1701  GATGAAACCA CAAGACTTAC CTTCGCTCGG AAGTAAAACG ACAAACACAC
1751  ACAGTTTTGC CCGTTTTCAT GAGAAATGGG ACGTCTGCGC ACGAAACGCG
1801  CCGTCGCTTG AGGAGGACTT GTACAAACAC GATCTATGCA GGTTTCCCCA
1851  ACTGACACAA ACCGTGCAAC TTGAAACTCC GCCTGGTCTT TCCAGGTCTA
1901  GAGGGGTAAC ATTTTGTACT GTGTTTGACT CCACGCTCGA TCCACTAGCG
1951  AGTGTTAGTA GCGGTACTGC TGTCTCGTAG CGGAGCATGT TGGCCGTGGG
2001  AACACCTCCT TGGTAACAAG GACCCACGGG GCCGAAAGCC ATGTCCTAAC
2051  GGACCCAACA TGTGTGCAAC CCCAGCACGG CAGCTTTACT GTGAAACCCA
2101  CTTCAAGGTG ACATTGATAC TGGTACTCAA ACACTGGTGA CAGGCTAAGG
2151  ATGCCCTTCA GGTACCCCGA GGTAACAAGC GACACTCGGG ATCTGAGAAG
2201  GGGACTGGGA CTTCTTTAAA GTGCCCAGTT TAAAAAGCTT CTACGCCTGA
2251  ATAGGTGACC GGAGGCCGGC ACCTTTCCTT TTATAACCAC TGAACACATG
2301  GAAGACGCCA AAAACATAAA GAAAGGCCCG GCGCCATTCT ATCCTCTAGA
2351  GGATGGAACC GCTGGAGAGC AACTGCATAA GGCTATGAAG AGATACGCCC
2401  TGGTTCCTGG AACAATTGCT TTTACAGATG CACATATCGA GGTGAACATC
2451  ACGTACGCGG AATACTTCGA AATGTCCGTT CGGTTGGCAG AAGCTATGAA
2501  ACGATATGGG CTGAATACAA ATCACAGAAT CGTCGTATGC AGTGAAAACT
2551  CTCTTCAATT CTTTATGCCG GTGTTGGGCG CGTTATTTAT CGGAGTTGCA
2601  GTTGCGCCCG CGAACGACAT TTATAATGAA CGTGAATTGC TCAACAGTAT
2651  GAACATTTCG CAGCCTACCG TAGTGTTTGT TTCCAAAAAG GGGTTGCAAA
2701  AAATTTTGAA CGTGCAAAAA AAATTACCAA TAATCCAGAA AATTATTATC
2751  ATGGATTCTA AAACGGATTA CCAGGGATTT CAGTCGATGT ACACGTTCGT
```

Fig. 18-b

```
2801  CACATCTCAT CTACCTCCCG GTTTTAATGA ATACGATTTT GTACCAGAGT
2851  CCTTTGATCG TGACAAAACA ATTGCACTGA TAATGAATTC CTCTGGATCT
2901  ACTGGGTTAC CTAAGGGTGT GGCCCTTCCG CATAGAACTG CCTGCGTCAG
2951  ATTCTCGCAT GCCAGAGATC CTATTTTTGG CAATCAAATC ATTCCGGATA
3001  CTGCGATTTT AAGTGTTGTT CCATTCCATC ACGGTTTTGG AATGTTTACT
3051  ACACTCGGAT ATTTGATATG TGGATTTCGA GTCGTCTTAA TGTATAGATT
3101  TGAAGAAGAG CTGTTTTTAC GATCCCTTCA GGATTACAAA ATTCAAAGTG
3151  CGTTGCTAGT ACCAACCCTA TTTTCATTCT TCGCCAAAAG CACTCTGATT
3201  GACAAATACG ATTTATCTAA TTTACACGAA ATTGCTTCTG GGGGCGCACC
3251  TCTTTCGAAA GAAGTCGGGG AAGCGGTTGC AAAACGCTTC CATCTTCCAG
3301  GGATACGACA AGGATATGGG CTCACTGAGA CTACATCAGC TATTCTGATT
3351  ACACCCGAGG GGGATGATAA ACCGGCGCG GTCGGTAAAG TTGTTCCATT
3401  TTTTGAAGCG AAGGTTGTGG ATCTGGATAC CGGGAAAACG CTGGGCGTTA
3451  ATCAGAGAGG CGAATTATGT GTCAGAGGAC CTATGATTAT GTCCGGTTAT
3501  GTAAACAATC CGGAAGCGAC CAACGCCTTG ATTGACAAGG ATGGATGGCT
3551  ACATTCTGGA GACATAGCTT ACTGGGACGA AGACGAACAC TTCTTCATAG
3601  TTGACCGCTT GAAGTCTTTA ATTAAATACA AAGGATATCA GGTGGCCCCC
3651  GCTGAATTGG AATCGATATT GTTACAACAC CCCAACATCT TCGACGCGGG
3701  CGTGGCAGGT CTTCCCGACG ATGACGCCGG TGAACTTCCC GCCGCCGTTG
3751  TTGTTTTGGA GCACGGAAAG ACGATGACGG AAAAAGAGAT CGTGGATTAC
3801  GTCGCCAGTC AAGTAACAAC CGCGAAAAAG TTGCGCGGAG GAGTTGTGTT
3851  TGTGGACGAA GTACCGAAAG GTCTTACCGG AAAACTCGAC GCAAGAAAAA
3901  TCAGAGAGAT CCTCATAAAG GCCAAGAAGG GCGGAAAGTC CAAATTGTAA
3951  AATGTAACTG TATTCAGCGA TGACGAAATT CTTAGCTATT GTAATGACTC
4001  TAGAGGATCT TTGTGAAGGA ACCTTACTTC TGTGGTGTGA CATAATTGGA
4051  CAAACTACCT ACAGAGATTT AAAGCTCTAA GGTAAATATA AAATTTTTAA
4101  GTGTATAATG TGTTAAACTA CTGATTCTAA TTGTTTGTGT ATTTTAGATT
4151  CCAACCTATG GAACTGATGA ATGGGAGCAG TGGTGGAATG CCTTTAATGA
4201  GGAAAACCTG TTTTGCTCAG AAGAAATGCC ATCTAGTGAT GATGAGGCTA
```

Fig. 18-c

```
4251  CTGCTGACTC TCAACATTCT ACTCCTCCAA AAAAGAAGAG AAAGGTAGAA
4301  GACCCCAAGG ACTTTCCTTC AGAATTGCTA AGTTTTTTGA GTCATGCTGT
4351  GTTTAGTAAT AGAACTCTTG CTTGCTTTGC TATTTACACC ACAAAGGAAA
4401  AAGCTGCACT GCTATACAAG AAAATTATGG AAAAATATTC TGTAACCTTT
4451  ATAAGTAGGC ATAACAGTTA TAATCATAAC ATACTGTTTT TTCTTACTCC
4501  ACACAGGCAT AGAGTGTCTG CTATTAATAA CTATGCTCAA AAATTGTGTA
4551  CCTTTAGCTT TTTAATTTGT AAAGGGGTTA ATAAGGAATA TTTGATGTAT
4601  AGTGCCTTGA CTAGAGATCA TAATCAGCCA TACCACATTT GTAGAGGTTT
4651  TACTTGCTTT AAAAAACCTC CCACACCTCC CCCTGAACCT GAAACATAAA
4701  ATGAATGCAA TTGTTGTTGT TAACTTGTTT ATTGCAGCTT ATAATGGTTA
4751  CAAATAAAGC AATAGCATCA CAAATTTCAC AAATAAAGCA TTTTTTTCAC
4801  TGCATTCTAG TTGTGGTTTG TCCAAACTCA TCAATGTATC TTATCATGTC
4851  TGGATCCCCG GGTCCCTATA GTGAGTCGTA TTAGCTTGGC GTAATCATGG
4901  TCATAGCTGT TTCCTGTGTG AAATTGTTAT CCGCTCACAA TTCCACACAA
4951  CATACGAGCC GGAAGCATAA AGTGTAAAGC CTGGGGTGCC TAATGAGTGA
5001  GCTAACTCAC ATTAATTGCG TTGCGCTCAC TGCCCGCTTT CCAGTCGGGA
5051  AACCTGTCGT GCCAGCTGCA TTAATGAATC GGCCAACGCG CGGGGAGAGG
5101  CGGTTTGCGT ATTGGGCGCT CTTCCGCTTC CTCGCTCACT GACTCGCTGC
5151  GCTCGGTCGT TCGGCTGCGG CGAGCGGTAT CAGCTCACTC AAAGGCGGTA
5201  ATACGGTTAT CCACAGAATC AGGGGATAAC GCAGGAAAGA ACATGTGAGC
5251  AAAAGGCCAG CAAAAGGCCA GGAACCGTAA AAAGGCCGCG TTGCTGGCGT
5301  TTTTCCATAG GCTCCGCCCC CCTGACGAGC ATCACAAAAA TCGACGCTCA
5351  AGTCAGAGGT GGCGAAACCC GACAGGACTA TAAAGATACC AGGCGTTTCC
5401  CCCTGGAAGC TCCCTCGTGC GCTCTCCTGT TCCGACCCTG CCGCTTACCG
5451  GATACCTGTC CGCCTTTCTC CCTTCGGGAA GCGTGGCGCT TTCTCAATGC
5501  TCACGCTGTA GGTATCTCAG TTCGGTGTAG GTCGTTCGCT CCAAGCTGGG
5551  CTGTGTGCAC GAACCCCCCG TTCAGCCCGA CCGCTGCGCC TTATCCGGTA
5601  ACTATCGTCT TGAGTCCAAC CCGGTAAGAC ACGACTTATC GCCACTGGCA
5651  GCAGCCACTG GTAACAGGAT TAGCAGAGCG AGGTATGTAG GCGGTGCTAC
```

Fig. 18-d

5701 AGAGTTCTTG AAGTGGTGGC CTAACTACGG CTACACTAGA AGGACAGTAT
5751 TTGGTATCTG CGCTCTGCTG AAGCCAGTTA CCTTCGGAAA AAGAGTTGGT
5801 AGCTCTTGAT CCGGCAAACA AACCACCGCT GGTAGCGGTG GTTTTTTTGT
5851 TTGCAAGCAG CAGATTACGC GCAGAAAAAA AGGATCTCAA GAAGATCCTT
5901 TGATCTTTTC TACGGGGTCT GACGCTCAGT GGAACGAAAA CTCACGTTAA
5951 GGGATTTTGG TCATGAGATT ATCAAAAAGG ATCTTCACCT AGATCCTTTT
6001 AAATTAAAAA TGAAGTTTTA AATCAATCTA AGTATATAT GAGTAAACTT
6051 GGTCTGACAG TTACCAATGC TTAATCAGTG AGGCACCTAT CTCAGCGATC
6101 TGTCTATTTC GTTCATCCAT AGTTGCCTGA CTCCCCGTCG TGTAGATAAC
6151 TACGATACGG GAGGGCTTAC CATCTGGCCC CAGTGCTGCA ATGATACCGC
6201 GAGACCCACG CTCACCGGCT CCAGATTTAT CAGCAATAAA CCAGCCAGCC
6251 GGAAGGGCCG AGCGCAGAAG TGGTCCTGCA ACTTTATCCG CCTCCATCCA
6301 GTCTATTAAT TGTTGCCGGG AAGCTAGAGT AAGTAGTTCG CCAGTTAATA
6351 GTTTGCGCAA CGTTGTTGCC ATTGCTACAG GCATCGTGGT GTCACGCTCG
6401 TCGTTTGGTA TGGCTTCATT CAGCTCCGGT TCCCAACGAT CAAGGCGAGT
6451 TACATGATCC CCCATGTTGT GCAAAAAAGC GGTTAGCTCC TTCGGTCCTC
6501 CGATCGTTGT CAGAAGTAAG TTGGCCGCAG TGTTATCACT CATGGTTATG
6551 GCAGCACTGC ATAATTCTCT TACTGTCATG CCATCCGTAA GATGCTTTTC
6601 TGTGACTGGT GAGTACTCAA CCAAGTCATT CTGAGAATAG TGTATGCGGC
6651 GACCGAGTTG CTCTTGCCCG GCGTCAATAC GGGATAATAC CGCGCCACAT
6701 AGCAGAACTT TAAAAGTGCT CATCATTGGA AAACGTTCTT CGGGGCGAAA
6751 ACTCTCAAGG ATCTTACCGC TGTTGAGATC CAGTTCGATG TAACCCACTC
6801 GTGCACCCAA CTGATCTTCA GCATCTTTTA CTTTCACCAG CGTTTCTGGG
6851 TGAGCAAAAA CAGGAAGGCA AAATGCCGCA AAAAAGGGAA TAAGGGCGAC
6901 ACGGAAATGT TGAATACTCA TACTCTTCCT TTTTCAATAT TATTGAAGCA
6951 TTTATCAGGG TTATTGTCTC ATGAGCGGAT ACATATTTGA ATGTATTTAG
7001 AAAAATAAAC AAATAGGGGT TCCGCGCACA TTTCCCCGAA AAGTGCCACC
7051 TGACGTCTAA GAAACCATTA TTATCATGAC ATTAACCTAT AAAAATAGGC
7101 GTATCACGAG GCCCTTTCGT CTCGCGCGTT TCGGTGATGA CGGTGAAAAC

Fig. 18-e

```
7151  CTCTGACACA TGCAGCTCCC GGAGACGGTC ACAGCTTGTC TGTAAGCGGA
7201  TGCCGGGAGC AGACAAGCCC GTCAGGGCGC GTCAGCGGGT GTTGGCGGGT
7251  GTCGGGCTG GCTTAACTAT GCGGCATCAG AGCAGATTGT ACTGAGAGTG
7301  CACCATATGC GGTGTGAAAT ACCGCACAGA TGCGTAAGGA GAAAATACCG
7351  CATCAGGCGC CATTCGCCAT TCAGGCTGCG CAACTGTTGG GAAGGGCGAT
7401  CGGTGCGGGC CTCTTCGCTA TTACGCCAGC TGGCGAAAGG GGGATGTGCT
7451  GCAAGGCGAT TAAGTTGGGT AACGCCAGGG TTTTCCCAGT CACGACGTTG
7501  TAAAACGACG GCCAGTGAAT TCGACCTGC AGTCGACAGA AGCCTTACGT
7551  GACAGCTGGC GAAGAACCAT GGCCAGCTGG TGACAAGCCA AAACAGCTCT
7601  GGCTCGCAAA ACATGTTCCC TTGGCTGCTT TCCACTTCCC CTTGTGCTTT
7651  GTTTACTTGT GTCAGCTGGT TGGCTCCCTA GGTATGAGCT CATGCTTGGC
7701  TGGCAGCCAT CCAGTTTTAG CCAGCTCTGC TTTGTTTACT TGTGTCAGCT
7751  GGTTGGCTCC CTAGGTATGA GCTCATGCTT GGCTGGCAGC CATCCAGTTT
7801  TAGCCAGCTC CTCCCTACCT TCCCTTTTTT TTATATATAC AGGAGGCCGA
7851  GGCCGCCTCC GCCTCCAAGC TTACTCAGAA GTAGTAAGGG CGTGGAGGCT
7901  TTTTAGGAGG CCAGGGAAAT TCCCTTGTTT TTCCCTTTTT TGCAGTAATT
7951  TTTTGCTGCA AAAAGCTAA
```

Fig. 18-f

```
JCVPlong-gdnf  Length: 6971  June 8, 1999 16:42  Type: N  Check: 3588
       1 GCTAGCGATT TAGGTGACAC TATAGAATAG ATCCCCATGA AGTTATGGGA
      51 TGTCGTGGCT GTCTGCCTGG TGCTGCTCCA CACCGCGTCC GCCTTCCCGC
     101 TGCCCGCCGG TAAGAGGCCT CCCGAGGCGC CCGCCGAAGA CCGCTCCCTC
     151 GGCCGCCGCC GCGCGCCCTT CGCGCTGAGC AGTGACTCAA ATATGCCAGA
     201 GGATTATCCT GATCAGTTCG ATGATGTCAT GGATTTTATT CAAGCCACCA
     251 TTAAAAGACT GAAAAGGTCA CCAGATAAAC AAATGGCAGT GCTTCCTAGA
     301 AGAGAGCGGA ATCGGCAGGC TGCAGCTGCC AACCCAGAGA ATTCCAGAGG
     351 AAAAGGTCGG AGAGGCCAGA GGGGCAAAAA CCGGGGTTGT GTCTTAACTG
     401 CAATACATTT AAATGTCACT GACTTGGGTC TGGGCTATGA AACCAAGGAG
     451 GAACTGATTT TTAGGTACTG CAGCGGCTCT TGCGATGCAG CTGAGACAAC
     501 GTACGACAAA ATATTGAAAA ACTTATCCAG AAATAGAAGG CTGGTGAGTG
     551 ACAAAGTAGG GCAGGCATGT TGCAGACCCA TCGCCTTTGA TGATGACCTG
     601 TCGTTTTTAG ATGATAACCT GGTTTACCAT ATTCTAAGAA AGCATTCCGC
     651 TAAAAGGTGT GGATGTATCT GACTGGTGCG CCGTCTTTCC CGACGTTAAA
     701 GGGATGAAAC CACAAGACTT ACCTTCGCTC GGAAGTAAAA CGACAAACAC
     751 ACACAGTTTT GCCCGTTTTC ATGAGAAATG GGACGTCTGC GCACGAAACG
     801 CGCCGTCGCT TGAGGAGGAC TTGTACAAAC ACGATCTATG CAGGTTTCCC
     851 CAACTGACAC AAACCGTGCA ACTTGAAACT CCGCCTGGTC TTTCCAGGTC
     901 TAGAGGGGTA ACATTTTGTA CTGTGTTTGA CTCCACGCTC GATCCACTAG
     951 CGAGTGTTAG TAGCGGTACT GCTGTCTCGT AGCGGAGCAT GTTGGCCGTG
    1001 GGAACACCTC CTTGGTAACA AGGACCCACG GGGCCGAAAG CCATGTCCTA
    1051 ACGGACCCAA CATGTGTGCA ACCCCAGCAC GGCAGCTTTA CTGTGAAACC
    1101 CACTTCAAGG TGACATTGAT ACTGGTACTC AAACACTGGT GACAGGCTAA
    1151 GGATGCCCTT CAGGTACCCC GAGGTAACAA GCGACACTCG GGATCTGAGA
    1201 AGGGGACTGG GACTTCTTTA AAGTGCCCAG TTTAAAAAGC TTCTACGCCT
    1251 GAATAGGTGA CCGGAGGCCG GCACCTTTCC TTTTATAACC ACTGAACACA
    1301 TGGAAGACGC CAAAAACATA AAGAAAGGCC CGGCGCCATT CTATCCTCTA
    1351 GAGGATGGAA CCGCTGGAGA GCAACTGCAT AAGGCTATGA AGAGATACGC
    1401 CCTGGTTCCT GGAACAATTG CTTTTACAGA TGCACATATC GAGGTGAACA
    1451 TCACGTACGC GGAATACTTC GAAATGTCCG TTCGGTTGGC AGAAGCTATG
    1501 AAACGATATG GCTGAATAC AAATCACAGA ATCGTCGTAT GCAGTGAAAA
    1551 CTCTCTTCAA TTCTTTATGC CGGTGTTGGG CGCGTTATTT ATCGGAGTTG
    1601 CAGTTGCGCC CGCGAACGAC ATTTATAATG AACGTGAATT GCTCAACAGT
    1651 ATGAACATTT CGCAGCCTAC CGTAGTGTTT GTTTCAAAAA AGGGGTTGCA
    1701 AAAAATTTTG AACGTGCAAA AAAAATTACC AATAATCCAG AAAATTATTA
    1751 TCATGGATTC TAAAACGGAT TACCAGGGAT TTCAGTCGAT GTACACGTTC
    1801 GTCACATCTC ATCTACCTCC CGGTTTTAAT GAATACGATT TTGTACCAGA
    1851 GTCCTTTGAT CGTGACAAAA CAATTGCACT GATAATGAAT TCCTCTGGAT
    1901 CTACTGGGTT ACCTAAGGGT GTGGCCCTTC CGCATAGAAC TGCCTGCGTC
    1951 AGATTCTCGC ATGCCAGAGA TCCTATTTTT GGCAATCAAA TCATTCCGGA
    2001 TACTGCGATT TTAAGTGTTG TTCCATTCCA TCACGGTTTT GGAATGTTTA
    2051 CTACACTCGG ATATTTGATA TGTGGATTTC GAGTCGTCTT AATGTATAGA
    2101 TTTGAAGAAG AGCTGTTTTT ACGATCCCTT CAGGATTACA AAATTCAAAG
    2151 TGCGTTGCTA GTACCAACCC TATTTTCATT CTTCGCCAAA AGCACTCTGA
    2201 TTGACAAATA CGATTTATCT AATTTACACG AAATTGCTTC TGGGGGCGCA
    2251 CCTCTTTCGA AAGAAGTCGG GGAAGCGGTT GCAAAACGCT TCCATCTTCC
    2301 AGGGATACGA CAAGGATATG GGCTCACTGA GACTACATCA GCTATTCTGA
    2351 TTACACCCGA GGGGGATGAT AAACCGGGCG CGGTCGGTAA AGTTGTTCCA
    2401 TTTTTTGAAG CGAAGGTTGT GGATCTGGAT ACCGGGAAAA CGCTGGGCGT
    2451 TAATCAGAGA GGCGAATTAT GTGTCAGAGG ACCTATGATT ATGTCCGGTT
    2501 ATGTAAACAA TCCGGAAGCG ACCAACGCCT TGATTGACAA GGATGGATGG
    2551 CTACATTCTG GAGACATAGC TTACTGGGAC GAAGACGAAC ACTTCTTCAT
    2601 AGTTGACCGC TTGAAGTCTT TAATTAAATA CAAAGGATAT CAGGTGGCCC
    2651 CCGCTGAATT GGAATCGATA TTGTTACAAC ACCCCAACAT CTTCGACGCG
    2701 GGCGTGGCAG GTCTTCCCGA CGATGACGCC GGTGAACTTC CCGCCGCCGT
    2751 TGTTGTTTG GAGCACGGAA AGACGATGAC GGAAAAAGAG ATCGTGGATT
    2801 ACGTCGCCAG TCAAGTAACA ACCGCGAAAA AGTTGCGCGG AGGAGTTGTG
    2851 TTTGTGGACG AAGTACCGAA AGGTCTTACC GGAAAACTCG ACGCAAGAAA
    2901 AATCAGAGAG ATCCTCATAA AGGCCAAGAA GGGCGGAAAG TCCAAATTGT
    2951 AAAATGTAAC TGTATTCAGC GATGACGAAA TTCTTAGCTA TTGTAATGAC
    3001 TCTAGAGGAT CTTTGTGAAG GAACCTTACT TCTGTGGTGT GACATAATTG
    3051 GACAAACTAC CTACAGAGAT TTAAAGCTCT AAGGTAAATA TAAAATTTTT
    3101 AAGTGTATAA TGTGTTAAAC TACTGATTCT AATTGTTTGT GTATTTTAGA
    3151 TTCCAACCTA TGGAACTGAT GAATGGGAGC AGTGGTGGAA TGCCTTTAAT
    3201 GAGGAAAACC TGTTTTGCTC AGAAGAAATG CCATCTAGTG ATGATGAGGC
```

Fig. 19-a

```
3251  TACTGCTGAC TCTCAACATT CTACTCCTCC AAAAAAGAAG AGAAAGGTAG
3301  AAGACCCCAA GGACTTTCCT TCAGAATTGC TAAGTTTTTT GAGTCATGCT
3351  GTGTTTAGTA ATAGAACTCT TGCTTGCTTT GCTATTTACA CCACAAAGGA
3401  AAAAGCTGCA CTGCTATACA AGAAAATTAT GGAAAAATAT TCTGTAACCT
3451  TTATAAGTAG GCATAACAGT TATAATCATA ACATACTGTT TTTTCTTACT
3501  CCACACAGGC ATAGAGTGTC TGCTATTAAT AACTATGCTC AAAAATTGTG
3551  TACCTTTAGC TTTTTAATTT GTAAAGGGGT TAATAAGGAA TATTTGATGT
3601  ATAGTGCCTT GACTAGAGAT CATAATCAGC CATACCACAT TTGTAGAGGT
3651  TTTACTTGCT TTAAAAAACC TCCCACACCT CCCCCTGAAC CTGAAACATA
3701  AAATGAATGC AATTGTTGTT GTTAACTTGT TTATTGCAGC TTATAATGGT
3751  TACAAATAAA GCAATAGCAT CACAAATTTC ACAAATAAAG CATTTTTTTC
3801  ACTGCATTCT AGTTGTGGTT TGTCCAAACT CATCAATGTA TCTTATCATG
3851  TCTGGATCCC CGGGTCCCTA TAGTGAGTCG TATTAGCTTG GCGTAATCAT
3901  GGTCATAGCT GTTTCCTGTG TGAAATTGTT ATCCGCTCAC AATTCCACAC
3951  AACATACGAG CCGGAAGCAT AAAGTGTAAA GCCTGGGGTG CCTAATGAGT
4001  GAGCTAACTC ACATTAATTG CGTTGCGCTC ACTGCCCGCT TTCCAGTCGG
4051  GAAACCTGTC GTGCCAGCTG CATTAATGAA TCGGCCAACG CGCGGGGAGA
4101  GGCGGTTTGC GTATTGGGCG CTCTTCCGCT TCCTCGCTCA CTGACTCGCT
4151  GCGCTCGGTC GTTCGGCTGC GGCGAGCGGT ATCAGCTCAC TCAAAGGCGG
4201  TAATACGGTT ATCCACAGAA TCAGGGGATA ACGCAGGAAA GAACATGTGA
4251  GCAAAAGGCC AGCAAAAGGC CAGGAACCGT AAAAAGGCCG CGTTGCTGGC
4301  GTTTTTCCAT AGGCTCCGCC CCCCTGACGA GCATCACAAA AATCGACGCT
4351  CAAGTCAGAG GTGGCGAAAC CCGACAGGAC TATAAAGATA CCAGGCGTTT
4401  CCCCCTGGAA GCTCCCTCGT GCGCTCTCCT GTTCCGACCC TGCCGCTTAC
4451  CGGATACCTG TCCGCCTTTC TCCCTTCGGG AAGCGTGGCG CTTTCTCAAT
4501  GCTCACGCTG TAGGTATCTC AGTTCGGTGT AGGTCGTTCG CTCCAAGCTG
4551  GGCTGTGTGC ACGAACCCCC CGTTCAGCCC GACCGCTGCG CCTTATCCGG
4601  TAACTATCGT CTTGAGTCCA ACCCGGTAAG ACACGACTTA TCGCCACTGG
4651  CAGCAGCCAC TGGTAACAGG ATTAGCAGAG CGAGGTATGT AGGCGGTGCT
4701  ACAGAGTTCT TGAAGTGGTG GCCTAACTAC GGCTACACTA GAAGGACAGT
4751  ATTTGGTATC TGCGCTCTGC TGAAGCCAGT TACCTTCGGA AAAAGAGTTG
4801  GTAGCTCTTG ATCCGGCAAA CAAACCACCG CTGGTAGCGG TGGTTTTTTT
4851  GTTTGCAAGC AGCAGATTAC GCGCAGAAAA AAAGGATCTC AAGAAGATCC
4901  TTTGATCTTT TCTACGGGGT CTGACGCTCA GTGGAACGAA AACTCACGTT
4951  AAGGGATTTT GGTCATGAGA TTATCAAAAA GGATCTTCAC CTAGATCCTT
5001  TTAAATTAAA AATGAAGTTT TAAATCAATC TAAAGTATAT ATGAGTAAAC
5051  TTGGTCTGAC AGTTACCAAT GCTTAATCAG TGAGGCACCT ATCTCAGCGA
5101  TCTGTCTATT TCGTTCATCC ATAGTTGCCT GACTCCCCGT CGTGTAGATA
5151  ACTACGATAC GGGAGGGCTT ACCATCTGGC CCCAGTGCTG CAATGATACC
5201  GCGAGACCCA CGCTCACCGG CTCCAGATTT ATCAGCAATA AACCAGCCAG
5251  CCGGAAGGGC CGAGCGCAGA AGTGGTCCTG CAACTTTATC CGCCTCCATC
5301  CAGTCTATTA ATTGTTGCCG GGAAGCTAGA GTAAGTAGTT CGCCAGTTAA
5351  TAGTTTGCGC AACGTTGTTG CCATTGCTAC AGGCATCGTG GTGTCACGCT
5401  CGTCGTTTGG TATGGCTTCA TTCAGCTCCG GTTCCCAACG ATCAAGGCGA
5451  GTTACATGAT CCCCCATGTT GTGCAAAAAA GCGGTTAGCT CCTTCGGTCC
5501  TCCGATCGTT GTCAGAAGTA AGTTGGCCGC AGTGTTATCA CTCATGGTTA
5551  TGGCAGCACT GCATAATTCT CTTACTGTCA TGCCATCCGT AAGATGCTTT
5601  TCTGTGACTG GTGAGTACTC AACCAAGTCA TTCTGAGAAT AGTGTATGCG
5651  GCGACCGAGT TGCTCTTGCC CGGCGTCAAT ACGGGATAAT ACCGCGCCAC
5701  ATAGCAGAAC TTTAAAAGTG CTCATCATTG GAAAACGTTC TTCGGGGCGA
5751  AAACTCTCAA GGATCTTACC GCTGTTGAGA TCCAGTTCGA TGTAACCCAC
5801  TCGTGCACCC AACTGATCTT CAGCATCTTT TACTTTCACC AGCGTTTCTG
5851  GGTGAGCAAA AACAGGAAGG CAAAATGCCG CAAAAAAGGG AATAAGGGCG
5901  ACACGGAAAT GTTGAATACT CATACTCTTC CTTTTTCAAT ATTATTGAAG
5951  CATTTATCAG GGTTATTGTC TCATGAGCGG ATACATATTT GAATGTATTT
6001  AGAAAAATAA ACAAATAGGG GTTCCGCGCA CATTTCCCCG AAAAGTGCCA
6051  CCTGACGTCT AAGAAACCAT TATTATCATG ACATTAACCT ATAAAAATAG
6101  GCGTATCACG AGGCCCTTTC GTCTCGCGCG TTTCGGTGAT GACGGTGAAA
6151  ACCTCTGACA CATGCAGCTC CCGGAGACGG TCACAGCTTG TCTGTAAGCG
6201  GATGCCGGGA GCAGACAAGC CCGTCAGGGC GCGTCAGCGG GTGTTGGCGG
6251  GTGTCGGGGC TGGCTTAACT ATGCGGCATC AGAGCAGATT GTACTGAGAG
6301  TGCACCATAT GCGGTGTGAA ATACCGCACA GATGCGTAAG GAGAAAATAC
6351  CGCATCAGGC GCCATTCGCC ATTCAGGCTG CGCAACTGTT GGGAAGGGCG
6401  ATCGGTGCGG GCCTCTTCGC TATTACGCCA GCTGGCGAAA GGGGGATGTG
6451  CTGCAAGGCG ATTAAGTTGG GTAACGCCAG GGTTTTCCCA GTCACGACGT
6501  TGTAAAACGA CGGCCAGTGA ATTCGACCT GCAGTCGACA GAAGCCTTAC
6551  GTGACAGCTG GCGAAGAACC ATGGCCAGCT GGTGACAAGC CAAAACAGCT
```

Fig. 19-b

```
6601  CTGGCTCGCA  AAACATGTTC  CCTTGGCTGC  TTTCCACTTC  CCCTTGTGCT
6651  TTGTTTACTT  GTGTCAGCTG  GTTGGCTCCC  TAGGTATGAG  CTCATGCTTG
6701  GCTGGCAGCC  ATCCAGTTTT  AGCCAGCTCT  GCTTTGTTTA  CTTGTGTCAG
6751  CTGGTTGGCT  CCCTAGGTAT  GAGCTCATGC  TTGGCTGGCA  GCCATCCAGT
6801  TTTAGCCAGC  TCCTCCCTAC  CTTCCCTTTT  TTTTATATAT  ACAGGAGGCC
6851  GAGGCCGCCT  CCGCCTCCAA  GCTTACTCAG  AAGTAGTAAG  GGCGTGGAGG
6901  CTTTTTAGGA  GGCCAGGGAA  ATTCCCTTGT  TTTTCCCTTT  TTTGCAGTAA
6951  TTTTTTGCTG  CAAAAAGCTA  A
```

Fig. 19-c pD12JCVPshort-hCNTF

Length: 7558

```
   1  GCTAGCGATT TAGGTGACAC TATAGAATCt cgacnnGTCA CCCCTAGAGT
  51  CGAGCTGTGA CGGTCCTTAC AATGAAATGC ANCTGGGTTA TCTTCTTCCT
 101  GATGGCAGGG GTTACAGGTA AGGGGCTCCC AAGTCCCAAA CTTGAGGGTC
 151  CATAAACTCT GTGACAGTGG CAATCACTTT GCCTTTCTTT CTACAGGGGT
 201  GAATTCGGCT TTCACAGAGC ATTCACCGCT GACCCCTCAC CGTCGGGACC
 251  TCTGTAGCCG CTCTATCTGG CTAGCAAGGA AGATTCGTTC AGACCTTGAC
 301  TGCTCTTACG GAATCCTATG TAAGTTGCCT ATTTTGCTGT TATCTGTTTT
 351  CCCTTCATCT TTTTTGATCC AGCAACTTAC CATCACGCAT CAGCTCCATT
 401  ACCAATTGTG AAAGCTCTAA TCATATAGTC ATTCATATAG GTTATTTGAC
 451  ATGGGCCCTT CCCTTGAGGA AACCCATGTG ACTTTATTTT CTTCCTCTGG
 501  GCTGTTTAGG AGATGAAGTT ACTTGAATGA GAAAATATAT ATGGAGTTCT
 551  AGAAAGGATT GGTTTATATG TCTTGGAGGC TATTTCAAAA TTTATTTGGC
 601  CATATATTCT GAATACTACC TAGAACAGAT TAGCCATGGG CCCTNTGGGT
 651  TNTTCATAAG CCATTGTTCT GAANTTTTTT AGCTTTGTAA ATGAAAGGTT
 701  TATGGGATAG GAAGAGTNCT ATGAACGTGG GAGGAATTTG TAAATCCTAC
 751  CAATTTNTNC TATATAGCAT TAGCCCCCAC CTTTTANTAT TCTGCATCAA
 801  AAGTAAGATT GTGTCTAAAG AGAAAGGTNA GCTATCAAAA GGACTCCTAT
 851  AANATTCNTT GGAAACTTNT GGAANTGTCA AATTTNTTTG AGCTAATTNT
 901  TGGAGTTCCA AANTTTGTCT TNTNACAGTN AAGGGGGANC CCCATTCANA
 951  TTTNCCCCCC TNNNGANAAT GCTTGGGGGA AAAAACCTNC CAACCCCNTT
1001  GTGGGANGAA GTTTTTTTAA NNTTTTAAGG CTNGNNGAAA CNGGNTTTTA
1051  ATTTTTTGGG NCNANCGCCT NTCCCCGGTA CCAGGAAAAT CAGGACCTNT
1101  TTTTGGGGNN GNGCNCCNAC NGGGGGGNAA AANGGGAAAT TCNTCANAA
1151  AAAATCTTTT CCGnnnnnng tgaagcatca gggcctgaac aagaacatca
1201  acctggactc tgcggatggg atgccagtgg caagcactga tcagtggagt
1251  gagctgaccg aggcagagcg actccaagag aaccttcaag cttatcgtac
1301  cttccatgtt ttgttggcca ggctcttaga agaccagcag gtgcatttta
1351  ccccaaccga aggtgacttc atcaagcta tacatacct tcttctccaa
```

Fig. 20-a

```
1401  gtcgctgcct ttgcatacca gatagaggag ttaatgatac tcctggaata
1451  caagatcccc cgcaatgagg ctgatgggat gcctattaat gttggagatg
1501  gtggtctctt tgagaagaag ctgtggggcc taaaggtgct gcaggagctt
1551  tcacagtgga cagtaaggtc catccatgac cttcgtttca tttcttctca
1601  tcagactggg atcccagcac gtgggagcca ttatattgct aacaacaaga
1651  aaatgtagnn nnngcggccT GCGCCGTCTT TCCCGACGTT AAAGGGATGA
1701  AACCACAAGA CTTACCTTCG CTCGGAAGTA AAACGACAAA CACACACAGT
1751  TTTGCCCGTT TTCATGAGAA ATGGGACGTC TGCGCACGAA ACGCGCCGTC
1801  GCTTGAGGAG GACTTGTACA AACACGATCT ATGCAGGTTT CCCCAACTGA
1851  CACAAACCGT GCAACTTGAA ACTCCGCCTG GTCTTTCCAG GTCTAGAGGG
1901  GTAACATTTT GTACTGTGTT TGACTCCACG CTCGATCCAC TAGCGAGTGT
1951  TAGTAGCGGT ACTGCTGTCT CGTAGCGGAG CATGTTGGCC GTGGGAACAC
2001  CTCCTTGGTA ACAAGGACCC ACGGGCCGA AGCCATGTC CTAACGGACC
2051  CAACATGTGT GCAACCCCAG CACGGCAGCT TTACTGTGAA ACCCACTTCA
2101  AGGTGACATT GATACTGGTA CTCAAACACT GGTGACAGGC TAAGGATGCC
2151  CTTCAGGTAC CCCGAGGTAA CAAGCGACAC TCGGGATCTG AGAAGGGGAC
2201  TGGGACTTCT TTAAAGTGCC CAGTTTAAAA AGCTTCTACG CCTGAATAGG
2251  TGACCGGAGG CCGGCACCTT TCCTTTTATA ACCACTGAAC ACATGGAAGA
2301  CGCCAAAAAC ATAAAGAAAG GCCCGGCGCC ATTCTATCCT CTAGAGGATG
2351  GAACCGCTGG AGAGCAACTG CATAAGGCTA TGAAGAGATA CGCCCTGGTT
2401  CCTGGAACAA TTGCTTTTAC AGATGCACAT ATCGAGGTGA ACATCACGTA
2451  CGCGGAATAC TTCGAAATGT CCGTTCGGTT GGCAGAAGCT ATGAAACGAT
2501  ATGGGCTGAA TACAAATCAC AGAATCGTCG TATGCAGTGA AAACTCTCTT
2551  CAATTCTTTA TGCCGGTGTT GGGCGCGTTA TTTATCGGAG TTGCAGTTGC
2601  GCCCGCGAAC GACATTTATA ATGAACGTGA ATTGCTCAAC AGTATGAACA
2651  TTTCGCAGCC TACCGTAGTG TTTGTTTCCA AAAAGGGGTT GCAAAAAATT
2701  TTGAACGTGC AAAAAAAATT ACCAATAATC CAGAAAATTA TTATCATGGA
2751  TTCTAAAACG GATTACCAGG GATTTCAGTC GATGTACACG TTCGTCACAT
2801  CTCATCTACC TCCCGGTTTT AATGAATACG ATTTTGTACC AGAGTCCTTT
```

Fig. 20-b

2851 GATCGTGACA AAACAATTGC ACTGATAATG AATTCCTCTG GATCTACTGG
2901 GTTACCTAAG GGTGTGGCCC TTCCGCATAG AACTGCCTGC GTCAGATTCT
2951 CGCATGCCAG AGATCCTATT TTTGGCAATC AAATCATTCC GGATACTGCG
3001 ATTTTAAGTG TTGTTCCATT CCATCACGGT TTTGGAATGT TTACTACACT
3051 CGGATATTTG ATATGTGGAT TTCGAGTCGT CTTAATGTAT AGATTTGAAG
3101 AAGAGCTGTT TTTACGATCC CTTCAGGATT ACAAAATTCA AAGTGCGTTG
3151 CTAGTACCAA CCCTATTTTC ATTCTTCGCC AAAAGCACTC TGATTGACAA
3201 ATACGATTTA TCTAATTTAC ACGAAATTGC TTCTGGGGGC GCACCTCTTT
3251 CGAAAGAAGT CGGGGAAGCG GTTGCAAAAC GCTTCCATCT TCCAGGGATA
3301 CGACAAGGAT ATGGGCTCAC TGAGACTACA TCAGCTATTC TGATTACACC
3351 CGAGGGGGAT GATAAACCGG GCGCGGTCGG TAAAGTTGTT CCATTTTTTG
3401 AAGCGAAGGT TGTGGATCTG GATACCGGGA AAACGCTGGG CGTTAATCAG
3451 AGAGGCGAAT TATGTGTCAG AGGACCTATG ATTATGTCCG GTTATGTAAA
3501 CAATCCGGAA GCGACCAACG CCTTGATTGA CAAGGATGGA TGGCTACATT
3551 CTGGAGACAT AGCTTACTGG GACGAAGACG AACACTTCTT CATAGTTGAC
3601 CGCTTGAAGT CTTTAATTAA ATACAAAGGA TATCAGGTGG CCCCCGCTGA
3651 ATTGGAATCG ATATTGTTAC AACACCCCAA CATCTTCGAC GCGGGCGTGG
3701 CAGGTCTTCC CGACGATGAC GCCGGTGAAC TTCCCGCCGC CGTTGTTGTT
3751 TTGGAGCACG GAAAGACGAT GACGGAAAAA GAGATCGTGG ATTACGTCGC
3801 CAGTCAAGTA ACAACCGCGA AAAAGTTGCG CGGAGGAGTT GTGTTTGTGG
3851 ACGAAGTACC GAAAGGTCTT ACCGGAAAAC TCGACGCAAG AAAAATCAGA
3901 GAGATCCTCA TAAAGGCCAA GAAGGGCGGA AAGTCCAAAT TGTAAAATGT
3951 AACTGTATTC AGCGATGACG AAATTCTTAG CTATTGTAAT GACTCTAGAG
4001 GATCTTTGTG AAGGAACCTT ACTTCTGTGG TGTGACATAA TTGGACAAAC
4051 TACCTACAGA GATTTAAAGC TCTAAGGTAA ATATAAAATT TTTAAGTGTA
4101 TAATGTGTTA AACTACTGAT TCTAATTGTT TGTGTATTTT AGATTCCAAC
4151 CTATGGAACT GATGAATGGG AGCAGTGGTG AATGCCTTT AATGAGGAAA
4201 ACCTGTTTTG CTCAGAAGAA ATGCCATCTA GTGATGATGA GGCTACTGCT
4251 GACTCTCAAC ATTCTACTCC TCCAAAAAAG AAGAGAAAGG TAGAAGACCC
4301 CAAGGACTTT CCTTCAGAAT TGCTAAGTTT TTTGAGTCAT GCTGTGTTTA

Fig. 20-c

```
4351  GTAATAGAAC TCTTGCTTGC TTTGCTATTT ACACCACAAA GGAAAAAGCT
4401  GCACTGCTAT ACAAGAAAAT TATGGAAAAA TATTCTGTAA CCTTTATAAG
4451  TAGGCATAAC AGTTATAATC ATAACATACT GTTTTTTCTT ACTCCACACA
4501  GGCATAGAGT GTCTGCTATT AATAACTATG CTCAAAAATT GTGTACCTTT
4551  AGCTTTTTAA TTTGTAAAGG GGTTAATAAG GAATATTTGA TGTATAGTGC
4601  CTTGACTAGA GATCATAATC AGCCATACCA CATTTGTAGA GGTTTTACTT
4651  GCTTTAAAAA ACCTCCCACA CCTCCCCCTG AACCTGAAAC ATAAAATGAA
4701  TGCAATTGTT GTTGTTAACT TGTTTATTGC AGCTTATAAT GGTTACAAAT
4751  AAAGCAATAG CATCACAAAT TTCACAAATA AAGCATTTTT TTCACTGCAT
4801  TCTAGTTGTG GTTTGTCCAA ACTCATCAAT GTATCTTATC ATGTCTGGAT
4851  CCCCGGGTCC CTATAGTGAG TCGTATTAGC TTGGCGTAAT CATGGTCATA
4901  GCTGTTTCCT GTGTGAAATT GTTATCCGCT CACAATTCCA CACAACATAC
4951  GAGCCGGAAG CATAAAGTGT AAAGCCTGGG GTGCCTAATG AGTGAGCTAA
5001  CTCACATTAA TTGCGTTGCG CTCACTGCCC GCTTTCCAGT CGGGAAACCT
5051  GTCGTGCCAG CTGCATTAAT GAATCGGCCA ACGCGCGGGG AGAGGCGGTT
5101  TGCGTATTGG GCGCTCTTCC GCTTCCTCGC TCACTGACTC GCTGCGCTCG
5151  GTCGTTCGGC TGCGGCGAGC GGTATCAGCT CACTCAAAGG CGGTAATACG
5201  GTTATCCACA GAATCAGGGG ATAACGCAGG AAAGAACATG TGAGCAAAAG
5251  GCCAGCAAAA GGCCAGGAAC CGTAAAAAGG CCGCGTTGCT GGCGTTTTTC
5301  CATAGGCTCC GCCCCCCTGA CGAGCATCAC AAAAATCGAC GCTCAAGTCA
5351  GAGGTGGCGA AACCCGACAG GACTATAAAG ATACCAGGCG TTTCCCCCTG
5401  GAAGCTCCCT CGTGCGCTCT CCTGTTCCGA CCCTGCCGCT TACCGGATAC
5451  CTGTCCGCCT TTCTCCCTTC GGGAAGCGTG GCGCTTTCTC AATGCTCACG
5501  CTGTAGGTAT CTCAGTTCGG TGTAGGTCGT TCGCTCCAAG CTGGGCTGTG
5551  TGCACGAACC CCCCGTTCAG CCCGACCGCT GCGCCTTATC CGGTAACTAT
5601  CGTCTTGAGT CCAACCCGGT AAGACACGAC TTATCGCCAC TGGCAGCAGC
5651  CACTGGTAAC AGGATTAGCA GAGCGAGGTA TGTAGGCGGT GCTACAGAGT
5701  TCTTGAAGTG GTGGCCTAAC TACGGCTACA CTAGAAGGAC AGTATTTGGT
5751  ATCTGCGCTC TGCTGAAGCC AGTTACCTTC GGAAAAAGAG TTGGTAGCTC
```

Fig. 20-d

```
5801  TTGATCCGGC AAACAAACCA CCGCTGGTAG CGGTGGTTTT TTTGTTTGCA
5851  AGCAGCAGAT TACGCGCAGA AAAAAGGAT CTCAAGAAGA TCCTTTGATC
5901  TTTTCTACGG GGTCTGACGC TCAGTGGAAC GAAAACTCAC GTTAAGGGAT
5951  TTTGGTCATG AGATTATCAA AAAGGATCTT CACCTAGATC CTTTTAAATT
6001  AAAAATGAAG TTTTAAATCA ATCTAAAGTA TATATGAGTA AACTTGGTCT
6051  GACAGTTACC AATGCTTAAT CAGTGAGGCA CCTATCTCAG CGATCTGTCT
6101  ATTTCGTTCA TCCATAGTTG CCTGACTCCC CGTCGTGTAG ATAACTACGA
6151  TACGGGAGGG CTTACCATCT GGCCCCAGTG CTGCAATGAT ACCGCGAGAC
6201  CCACGCTCAC CGGCTCCAGA TTTATCAGCA ATAAACCAGC CAGCCGGAAG
6251  GGCCGAGCGC AGAAGTGGTC CTGCAACTTT ATCCGCCTCC ATCCAGTCTA
6301  TTAATTGTTG CCGGGAAGCT AGAGTAAGTA GTTCGCCAGT TAATAGTTTG
6351  CGCAACGTTG TTGCCATTGC TACAGGCATC GTGGTGTCAC GCTCGTCGTT
6401  TGGTATGGCT TCATTCAGCT CCGGTTCCCA ACGATCAAGG CGAGTTACAT
6451  GATCCCCCAT GTTGTGCAAA AAAGCGGTTA GCTCCTTCGG TCCTCCGATC
6501  GTTGTCAGAA GTAAGTTGGC CGCAGTGTTA TCACTCATGG TTATGGCAGC
6551  ACTGCATAAT TCTCTTACTG TCATGCCATC CGTAAGATGC TTTTCTGTGA
6601  CTGGTGAGTA CTCAACCAAG TCATTCTGAG AATAGTGTAT GCGGCGACCG
6651  AGTTGCTCTT GCCCGGCGTC AATACGGGAT AATACCGCGC CACATAGCAG
6701  AACTTTAAAA GTGCTCATCA TTGGAAAACG TTCTTCGGGG CGAAAACTCT
6751  CAAGGATCTT ACCGCTGTTG AGATCCAGTT CGATGTAACC CACTCGTGCA
6801  CCCAACTGAT CTTCAGCATC TTTTACTTTC ACCAGCGTTT CTGGGTGAGC
6851  AAAAACAGGA AGGCAAAATG CCGCAAAAAA GGGAATAAGG GCGACACGGA
6901  AATGTTGAAT ACTCATACTC TTCCTTTTTC AATATTATTG AAGCATTTAT
6951  CAGGGTTATT GTCTCATGAG CGGATACATA TTTGAATGTA TTTAGAAAAA
7001  TAAACAAATA GGGGTTCCGC GCACATTTCC CCGAAAAGTG CCACCTGACG
7051  TCTAAGAAAC CATTATTATC ATGACATTAA CCTATAAAAA TAGGCGTATC
7101  ACGAGGCCCT TTCGTCTCGC GCGTTTCGGT GATGACGGTG AAAACCTCTG
7151  ACACATGCAG CTCCCGGAGA CGGTCACAGC TTGTCTGTAA GCGGATGCCG
7201  GGAGCAGACA AGCCCGTCAG GGCGCGTCAG CGGGTGTTGG CGGGTGTCGG
7251  GGCTGGCTTA ACTATGCGGC ATCAGAGCAG ATTGTACTGA GAGTGCACCA
```

Fig. 20-e

```
7301  TATGCGGTGT GAAATACCGC ACAGATGCGT AAGGAGAAAA TACCGCATCA
7351  GGCGCCATTC GCCATTCAGG CTGCGCAACT GTTGGGAAGG GCGATCGGTG
7401  CGGGCCTCTT CGCTATTACG CCAGCTGGCG AAAGGGGGAT GTGCTGCAAG
7451  GCGATTAAGT TGGGTAACGC CAGGGTTTTC CCAGTCACGA CGTTGTAAAA
7501  CGACGGCCAG TGAATTTCGA CCTGCAGtcg acttttttta tatatacagg
7551  aggccgag
```

Fig. 20-f

JCVPshort-hgdnf  Length: 6565  June 8, 1999 16:57  Type: N  Check:

```
   1  GCTAGCGATT TAGGTGACAC TATAGAATAG ATCCCCATGA AGTTATGGGA
  51  TGTCGTGGCT GTCTGCCTGG TGCTGCTCCA CACCGCGTCC GCCTTCCCGC
 101  TGCCCGCCGG TAAGAGGCCT CCCGAGGCGC CCGCCGAAGA CCGCTCCCTC
 151  GGCCGCCGCC GCGCGCCCTT CGCGCTGAGC AGTGACTCAA ATATGCCAGA
 201  GGATTATCCT GATCAGTTCG ATGATGTCAT GGATTTTATT CAAGCCACCA
 251  TTAAAAGACT GAAAAGGTCA CCAGATAAAC AAATGGCAGT GCTTCCTAGA
 301  AGAGAGCGGA ATCGGCAGGC TGCAGCTGCC AACCCAGAGA ATTCCAGAGG
 351  AAAAGGTCGG AGAGGCCAGA GGGGCAAAAA CCGGGGTTGT GTCTTAACTG
 401  CAATACATTT AAATGTCACT GACTTGGGTC TGGGCTATGA AACCAAGGAG
 451  GAACTGATTT TTAGGTACTG CAGCGGCTCT TGCGATGCAG CTGAGACAAC
 501  GTACGACAAA ATATTGAAAA ACTTATCCAG AAATAGAAGG CTGGTGAGTG
 551  ACAAAGTAGG GCAGGCATGT TGCAGACCCA TCGCCTTTGA TGATGACCTG
 601  TCGTTTTTAG ATGATAACCT GGTTTACCAT ATTCTAAGAA AGCATTCCGC
 651  TAAAAGGTGT GGATGTATCT GACTGGTGCG CCGTCTTTCC CGACGTTAAA
 701  GGGATGAAAC CACAAGACTT ACCTTCGCTC GGAAGTAAAA CGACAAACAC
 751  ACACAGTTTT GCCCGTTTTC ATGAGAAATG GGACGTCTGC GCACGAAACG
 801  CGCCGTCGCT TGAGGAGGAC TTGTACAAAC ACGATCTATG CAGGTTTCCC
 851  CAACTGACAC AAACCGTGCA ACTTGAAACT CCGCCTGGTC TTTCCAGGTC
 901  TAGAGGGGTA ACATTTTGTA CTGTGTTTGA CTCCACGCTC GATCCACTAG
 951  CGAGTGTTAG TAGCGGTACT GCTGTCTCGT AGCGGAGCAT GTTGGCCGTG
1001  GGAACACCTC CTTGGTAACA AGGACCCACG GGGCCGAAAG CCATGTCCTA
1051  ACGGACCCAA CATGTGTGCA ACCCCAGCAC GGCAGCTTTA CTGTGAAACC
1101  CACTTCAAGG TGACATTGAT ACTGGTACTC AAACACTGGT GACAGGCTAA
1151  GGATGCCCTT CAGGTACCCC GAGGTAACAA GCGACACTCG GGATCTGAGA
1201  AGGGGACTGG GACTTCTTTA AAGTGCCCAG TTTAAAAAGC TTCTACGCCT
1251  GAATAGGTGA CCGGAGGCCG GCACCTTTCC TTTTATAACC ACTGAACACA
1301  TGGAAGACGC CAAAAACATA AAGAAAGGCC CGGCGCCATT CTATCCTCTA
1351  GAGGATGGAA CCGCTGGAGA GCAACTGCAT AAGGCTATGA AGAGATACGC
1401  CCTGGTTCCT GGAACAATTG CTTTTACAGA TGCACATATC GAGGTGAACA
1451  TCACGTACGC GGAATACTTC GAAATGTCCG TTCGGTTGGC AGAAGCTATG
1501  AAACGATATG GGCTGAATAC AAATCACAGA ATCGTCGTAT GCAGTGAAAA
1551  CTCTCTTCAA TTCTTTATGC CGGTGTTGGG CGCGTTATTT ATCGGAGTTG
1601  CAGTTGCGCC CGCAACGAC ATTTATAATG AACGTGAATT GCTCAACAGT
1651  ATGAACATTT CGCAGCCTAC CGTAGTGTTT GTTTCCAAAA AGGGGTTGCA
1701  AAAAATTTTG AACGTGCAAA AAAAATTACC AATAATCCAG AAAATTATTA
1751  TCATGGATTC TAAAACGGAT TACCAGGGAT TTCAGTCGAT GTACACGTTC
1801  GTCACATCTC ATCTACCTCC CGGTTTTAAT GAATACGATT TTGTACCAGA
1851  GTCCTTTGAT CGTGACAAAA CAATTGCACT GATAATGAAT TCCTCTGGAT
1901  CTACTGGGTT ACCTAAGGGT GTGGCCCTTC CGCATAGAAT TGCCTGCGTC
1951  AGATTCTCGC ATGCCAGAGA TCCTATTTTT GGCAATCAAA TCATTCCGGA
2001  TACTGCGATT TTAAGTGTTG TTCCATTCCA TCACGGTTTT GGAATGTTTA
2051  CTACACTCGG ATATTTGATA TGTGGATTTC GAGTCGTCTT AATGTATAGA
2101  TTTGAAGAAG AGCTGTTTTT ACGATCCCTT CAGGATTACA AAATTCAAAG
2151  TGCGTTGCTA GTACCAACCC TATTTTCATT CTTCGCCAAA AGCACTCTGA
2201  TTGACAAATA CGATTTATCT AATTTACACG AAATTGCTTC TGGGGGCGCA
2251  CCTCTTTCGA AAGAAGTCGG GGAAGCGGTT GCAAAACGCT TCCATCTTCC
2301  AGGGATACGA CAAGGATATG GGCTCACTGA GACTACATCA GCTATTCTGA
2351  TTACACCCGA GGGGGATGAT AAACCGGGCG CGGTCGGTAA AGTTGTTCCA
2401  TTTTTTGAAG CGAAGGTTGT GGATCTGGAT ACCGGGAAAA CGCTGGGCGT
2451  TAATCAGAGA GGCGAATTAT GTGTCAGAGG ACCTATGATT ATGTCCGGTT
2501  ATGTAAACAA TCCGGAAGCG ACCAACGCCT TGATTGACAA GGATGGATGG
2551  CTACATTCTG GAGACATAGC TTACTGGGAC GAAGACGAAC ACTTCTTCAT
2601  AGTTGACCGC TTGAAGTCTT TAATTAAATA CAAAGGATAT CAGGTGGCCC
2651  CCGCTGAATT GGAATCGATA TTGTTACAAC ACCCCAACAT CTTCGACGCG
2701  GGCGTGGCAG GTCTTCCCGA CGATGACGCC GGTGAACTTC CCGCCGCCGT
2751  TGTTGTTTTG GAGCACGGAA AGACGATGAC GGAAAAAGAG ATCGTGGATT
2801  ACGTCGCCAG TCAAGTAACA ACCGCGAAAA AGTTGCGCGG AGGAGTTGTG
2851  TTTGTGGACG AAGTACCGAA AGGTCTTACC GGAAAACTCG ACGCAAGAAA
2901  AATCAGAGAG ATCCTCATAA AGGCCAAGAA GGGCGGAAAG TCCAAATTGT
2951  AAAATGTAAC TGTATTCAGC GATGACGAAA TTCTTAGCTA TTGTAATGAC
3001  TCTAGAGGAT CTTTGTGAAG GAACCTTACT TCTGTGGTGT GACATAATTG
3051  GACAAACTAC CTACAGAGAT TTAAAGCTCT AAGGTAAATA TAAAATTTTT
3101  AAGTGTATAA TGTGTTAAAC TACTGATTCT AATTGTTTGT GTATTTTAGA
3151  TTCCAACCTA TGGAACTGAT GAATGGGAGC AGTGGTGGAA TGCCTTTAAT
```

Fig. 21-a

```
3201 GAGGAAAACC TGTTTTGCTC AGAAGAAATG CCATCTAGTG ATGATGAGGC
3251 TACTGCTGAC TCTCAACATT CTACTCCTCC AAAAAAGAAG AGAAAGGTAG
3301 AAGACCCCAA GGACTTTCCT TCAGAATTGC TAAGTTTTT GAGTCATGCT
3351 GTGTTTAGTA ATAGAACTCT TGCTTGCTTT GCTATTTACA CCACAAAGGA
3401 AAAAGCTGCA CTGCTATACA AGAAAATTAT GGAAAAATAT TCTGTAACCT
3451 TTATAAGTAG GCATAACAGT TATAATCATA ACATACTGTT TTTTCTTACT
3501 CCACACAGGC ATAGAGTGTC TGCTATTAAT AACTATGCTC AAAAATTGTG
3551 TACCTTTAGC TTTTTAATTT GTAAAGGGGT TAATAAGGAA TATTTGATGT
3601 ATAGTGCCTT GACTAGAGAT CATAATCAGC CATACCACAT TTGTAGAGGT
3651 TTTACTTGCT TTAAAAAACC TCCCACACCT CCCCCTGAAC CTGAAACATA
3701 AAATGAATGC AATTGTTGTT GTTAACTTGT TTATTGCAGC TTATAATGGT
3751 TACAAATAAA GCAATAGCAT CACAAATTTC ACAAATAAAG CATTTTTTTC
3801 ACTGCATTCT AGTTGTGGTT TGTCCAAACT CATCAATGTA TCTTATCATG
3851 TCTGGATCCC CGGGTCCCTA TAGTGAGTCG TATTAGCTTG GCGTAATCAT
3901 GGTCATAGCT GTTTCCTGTG TGAAATTGTT ATCCGCTCAC AATTCCACAC
3951 AACATACGAG CCGGAAGCAT AAAGTGTAAA GCCTGGGGTG CCTAATGAGT
4001 GAGCTAACTC ACATTAATTG CGTTGCGCTC ACTGCCCGCT TTCCAGTCGG
4051 GAAACCTGTC GTGCCAGCTG CATTAATGAA TCGGCCAACG CGCGGGGAGA
4101 GGCGGTTTGC GTATTGGGCG CTCTTCCGCT TCCTCGCTCA CTGACTCGCT
4151 GCGCTCGGTC GTTCGGCTGC GGCGAGCGGT ATCAGCTCAC TCAAAGGCGG
4201 TAATACGGTT ATCCACAGAA TCAGGGGATA ACGCAGGAAA GAACATGTGA
4251 GCAAAAGGCC AGCAAAAGGC CAGGAACCGT AAAAAGGCCG CGTTGCTGGC
4301 GTTTTTCCAT AGGCTCCGCC CCCCTGACGA GCATCACAAA AATCGACGCT
4351 CAAGTCAGAG GTGGCGAAAC CCGACAGGAC TATAAAGATA CCAGGCGTTT
4401 CCCCCTGGAA GCTCCCTCGT GCGCTCTCCT GTTCCGACCC TGCCGCTTAC
4451 CGGATACCTG TCCGCCTTTC TCCCTTCGGG AAGCGTGGCG CTTTCTCAAT
4501 GCTCACGCTG TAGGTATCTC AGTTCGGTGT AGGTCGTTCG CTCCAAGCTG
4551 GGCTGTGTGC ACGAACCCCC CGTTCAGCCC GACCGCTGCG CCTTATCCGG
4601 TAACTATCGT CTTGAGTCCA ACCCGGTAAG ACACGACTTA TCGCCACTGG
4651 CAGCAGCCAC TGGTAACAGG ATTAGCAGAG CGAGGTATGT AGGCGGTGCT
4701 ACAGAGTTCT TGAAGTGGTG GCCTAACTAC GGCTACACTA GAAGGACAGT
4751 ATTTGGTATC TGCGCTCTGC TGAAGCCAGT TACCTTCGGA AAAAGAGTTG
4801 GTAGCTCTTG ATCCGGCAAA CAAACCACCG CTGGTAGCGG TGGTTTTTTT
4851 GTTTGCAAGC AGCAGATTAC GCGCAGAAAA AAAGGATCTC AAGAAGATCC
4901 TTTGATCTTT TCTACGGGGT CTGACGCTCA GTGGAACGAA AACTCACGTT
4951 AAGGGATTTT GGTCATGAGA TTATCAAAAA GGATCTTCAC CTAGATCCTT
5001 TTAAATTAAA AATGAAGTTT TAAATCAATC TAAAGTATAT ATGAGTAAAC
5051 TTGGTCTGAC AGTTACCAAT GCTTAATCAG TGAGGCACCT ATCTCAGCGA
5101 TCTGTCTATT TCGTTCATCC ATAGTTGCCT GACTCCCCGT CGTGTAGATA
5151 ACTACGATAC GGGAGGGCTT ACCATCTGGC CCCAGTGCTG CAATGATACC
5201 GCGAGACCCA CGCTCACCGG CTCCAGATTT ATCAGCAATA AACCAGCCAG
5251 CCGGAAGGGC CGAGCGCAGA AGTGGTCCTG CAACTTTATC CGCCTCCATC
5301 CAGTCTATTA ATTGTTGCCG GGAAGCTAGA GTAAGTAGTT CGCCAGTTAA
5351 TAGTTTGCGC AACGTTGTTG CCATTGCTAC AGGCATCGTG GTGTCACGCT
5401 CGTCGTTTGG TATGGCTTCA TTCAGCTCCG GTTCCCAACG ATCAAGGCGA
5451 GTTACATGAT CCCCCATGTT GTGCAAAAAA GCGGTTAGCT CCTTCGGTCC
5501 TCCGATCGTT GTCAGAAGTA AGTTGGCCGC AGTGTTATCA CTCATGGTTA
5551 TGGCAGCACT GCATAATTCT CTTACTGTCA TGCCATCCGT AAGATGCTTT
5601 TCTGTGACTG GTGAGTACTC AACCAAGTCA TTCTGAGAAT AGTGTATGCG
5651 GCGACCGAGT TGCTCTTGCC CGGCGTCAAT ACGGGATAAT ACCGCGCCAC
5701 ATAGCAGAAC TTTAAAAGTG CTCATCATTG GAAAACGTTC TTCGGGGCGA
5751 AAACTCTCAA GGATCTTACC GCTGTTGAGA TCCAGTTCGA TGTAACCCAC
5801 TCGTGCACCC AACTGATCTT CAGCATCTTT TACTTTCACC AGCGTTTCTG
5851 GGTGAGCAAA AACAGGAAGG CAAAATGCCG CAAAAAAGGG AATAAGGGCG
5901 ACACGGAAAT GTTGAATACT CATACTCTTC CTTTTTCAAT ATTATTGAAG
5951 CATTTATCAG GGTTATTGTC TCATGAGCGG ATACATATTT GAATGTATTT
6001 AGAAAAATAA ACAAATAGGG GTTCCGCGCA CATTTCCCCG AAAAGTGCCA
6051 CCTGACGTCT AAGAAACCAT TATTATCATG ACATTAACCT ATAAAAATAG
6101 GCGTATCACG AGGCCCTTTC GTCTCGCGCG TTTCGGTGAT GACGGTGAAA
6151 ACCTCTGACA CATGCAGCTC CCGGAGACGG TCACAGCTTG TCTGTAAGCG
6201 GATGCCGGGA GCAGACAAGC CCGTCAGGGC GCGTCAGCGG GTGTTGGCGG
6251 GTGTCGGGGC TGGCTTAACT ATGCGGCATC AGAGCAGATT GTACTGAGAG
6301 TGCACCATAT GCGGTGTGAA ATACCGCACA GATGCGTAAG GAGAAAATAC
6351 CGCATCAGGC GCCATTCGCC ATTCAGGCTG CGCAACTGTT GGGAAGGGCG
6401 ATCGGTGCGG GCCTCTTCGC TATTACGCCA GCTGGCGAAA GGGGGATGTG
6451 CTGCAAGGCG ATTAAGTTGG GTAACGCCAG GGTTTTCCCA GTCACGACGT
6501 TGTAAAACGA CGGCCAGTGA ATTCGACCT GCAGtcgact tttttatat
```

Fig. 21-b 6551 atacaggagg ccgag

Fig. 21-c pRetroOFF-E6E7  Length: 7840  June 10, 1999 12:21  Type: N
Check: 5234

```
   1 TCGAGTTTAC CACTCCCTAT CAGTGATAGA GAAAAGTGAA AGTCGAGTTT
  51 ACCACTCCCT ATCAGTGATA GAGAAAAGTG AAAGTCGAGT TTACCACTCC
 101 CTATCAGTGA TAGAGAAAGT GAAAGTCGAG TTTACCACTC CCTATCAGTG
 151 ATAGAGAAAA GTGAAAGTCG AGTTTACCAC TCCCTATCAG TGATAGAGAA
 201 AAGTGAAAGT CGAGTTTACC ACTCCCTATC AGTGATAGAG AAAAGTGAAG
 251 TCGAGTTTAC CACTCCCTAT CAGTGATAGA GAAAAGTGAA AGTCGAGCTC
 301 GGTACCCGGG TCGAGTAGGC GTGTACGGTG GGAGGCCTAT ATAAGCAGAG
 351 CTCGTTTAGT GAACCGTCAG ATCGCCTGGA GACGCCATCC ACGCTGTTTT
 401 GACCTCCATA GAAGACACCG GGACCGATCC AGCCTgcggc cgcagatcta
 451 attaccggt tagtataaaa gcagacattt tatgcaccaa aagagaactg
 501 caatgtttca ggacccacag gagcgaccca gaaagttacc acagttatgc
 551 acagagctgc aaacaactat acatgatata atattagaat gtgtgtactg
 601 caagcaacag ttactgcgac gtgaggtata tgactttgct tttcgggatt
 651 tatgcatagt atatagagat gggaatccat atgctgtatg tgataaatgt
 701 ttaaagtttt attctaaaat tagtgagtat agacattatt gttatagttt
 751 gtatggaaca acattagaac agcaatacaa caaaccgttg tgtgatttgt
 801 taattaggtg tattaactgt caaaagccac tgtgtcctga agaaaagcaa
 851 agacatctgg acaaaaagca aagattccat aatataaggg gtcggtggac
 901 cggtcgatgt atgtcttgtt gcagatcatc aagaacacgt agagaaaccc
 951 agctgtaatc atgcatggag atacacctac attgcatgaa tatatgttag
1001 atttgcaacc agagacaact gatctctact gttatgagca attaaatgac
1051 agctcagagg aggaggatga aatagatggt ccagctggac aagcagaacc
1101 ggacagagcc cattacaata ttgtaacctt ttgttgcaag tgtgactcta
1151 cgcttcggtt gtgcgtacaa agcacacg tagacattcg tactttggaa
1201 gacctgttaa tgggcacact aggaattgtg tgccccatct gttctcagaa
1251 accataatct accatggctg atcctgcagg atcCCCGGG AACAACAACA
1301 ATTGCATTCA TTTTATGTTT CAGGTTCAGG GGGAGGTGTG GGAGGTTTTT
1351 TAAAGCAAGT AAAACCTCTA CAAATGTGGT ATGGCTGATT ATGATCCTGC
1401 AAGCCTCGTC GTCTGGCCGG ACCACGCTAT CTGTGCAAGG TCCCCGGACG
1451 CGCGCTCCAT GAGCAGAGCG TCGCGCCCCC TACCCACCGT ACTCGTCAAT
1501 TCCAAGGGCA TCGGTAAACA GAGCGCCGTA GGGGCGGAG TCGTGGGGG
1551 TAAATCCCGG ACCCGGGGAA TCCCCGTCCC CCAACATGTC CAGATCGAAA
1601 TCGTCTAGCG CGTCGGCATG CGCCATCGCC ACGTCCTCGC CGTATAAGTG
1651 GAGCTCGTCC CCCAGGCTGA CATCGGTCGG GGGGCCGTC GACAGTCTGC
1701 GCGTGTGTCC GCGGGGAGAA AGGACAGGCG CGGAGCCGCC AGCCCCGCCT
1751 CTTCGGGGGC GTCGTCGTCC GGGAGATCGA GCAGGCCCTC GATGGTAGAC
1801 CCGTAATTGT TTTTCGTACG CGCGCGGCTG TACGCGGACC CACTTTCACA
1851 TTTAAGTTGT TTTTCTAATC CGCATATGAT CAATTCAAGG CCGAATAAGA
1901 AGGCTGGCTC TGCACCTTGG TGATCAAATA ATTCGATAGC TTGTCGTAAT
1951 AATGGCGGCA TACTATCAGT AGTAGGTGTT TCCCTTTCTT CTTTAGCGAC
2001 TTGATGCTCT TGATCTTCCA ATACGCAACC TAAAGTAAAA TGCCCCACAG
2051 CGCTGAGTGC ATATAATGCA TTCTCTAGTG AAAAACCTTG TTGGCATAAA
2101 AAGGCTAATT GATTTTCGAG AGTTTCATAC TGTTTTTCTG TAGGCCGTGT
2151 ACCTAAATGT ACTTTTGCTC CATCGCGATG ACTTAGTAAA GCACATCTAA
2201 AACTTTTAGC GTTATTACGT AAAAAATCTT GCCAGCTTTC CCCTTCTAAA
2251 GGGCAAAAGT GAGTATGGTG CCTATCTAAC ATCTCAATGG CTAAGGCGTC
2301 GAGCAAAGCC CGCTTATTTT TTACATGCCA ATACAATGTA GGCTGCTCTA
2351 CACCTAGCTT CTGGGCGAGT TTACGGGTTG TTAAACCTTC GATTCCGACC
2401 TCATTAAGCA GCTCTAATGC GCTGTTAATC ACTTTACTTT TATCTAATCT
2451 AGACATGGTG GAAGCTTTTT GCAAAAGCCT AGGCCTCCAA AAAAGCCTCC
2501 TCACTACTTC TGGAATAGCT CAGAGGCCGA GGCGGCCTCG GCCTCTGCAT
2551 AAATAAAAAA AATTAGTCAG CCATGGGGCG GAGAATGGGC GGAACTGGGC
2601 GGAGTTAGGG GCGGGATGGG CGGAGTTAGG GGCGGGACTA TGGTTGCTGA
2651 CTAATTGAGA TGCATGCTTT GCATACTTCT GCCTGCTGGG GAGCCTGGGG
2701 ACTTTCCACA CCTGGTTGCT GACTAATTGA GATGCATGCT TTGCATACTT
2751 CTGCCTGCTG GGGAGCCTGG GGACTTTCCA CACCCTAACT GACACACATT
```

Fig. 22-a

```
2801  CCACAGGTCG ACTAGATCGA ATTCTCAATT GTTTTACGCG GCCCGATGCA
2851  TGGGGTCGTG CGCTCCTTTC GGTCGGGCGC TGCGGGTCGT GGGGCGGGCG
2901  TCAGGCACCG GGCTTGCGGG TCATGCACCA GGTCGCGCGG TCCTTCGGGC
2951  ACTCGACGTC GGCGGTGACG GTGAAGCCGA GCCGCTCGTA GAAGGGGAGG
3001  TTGCGGGGCG CGGAGGTCTC CAGGAAGGCG GGCACCCCGG CGCGCTCGGC
3051  CGCCTCCACT CCGGGGAGCA CGACGGCGCT GCCCAGACCC TTGCCCTGGT
3101  GGTCGGGCGA GACGCCGACG GTGGCCAGGA ACCACGCGGG CTCCTTGGGC
3151  CGGTGCGGCG CCAGGAGGCC TTCCATCTGT TGCTGCGCGG CCAGCCGGGA
3201  ACCGCTCAAC TCGGCCATGC GCGGGCCGAT CTCGGCGAAC ACCGCCCCCG
3251  CTTCGACGCT CTCCGGCGTG GTCCAGACCG CCACCGCGGC GCCGTCGTCC
3301  GCGACCCACA CCTTGCCGAT GTCGAGCCCG ACGCGCGTGA GGAAGAGTTC
3351  TTGCAGCTCG GTGACCCGCT CGATGTGGCG GTCCGGATCG ACGGTGTGGC
3401  GCGTGGCGGG GTAGTCGGCG AACGCGGCGG CGAGGGTGCG TACGGCCCTG
3451  GGGACGTCGT CGCGGGTGGC GAGGCGCACC GTGGGCTTGT ACTCGGTCAT
3501  GGTAAGCTGA TCCGGCCGGC GCCTAGAGAA GGAGTGAGGG CTGGATAAAG
3551  GGAGGATTGA GGCGGGGTCG AAAGAGGAGG TTCAAGGGGG AGAGACGGCG
3601  CGGATGGAAG AAGAGGAGGC GGAGGCTTAG GGTGTACAAA GGGCTTGACC
3651  CAGGGAGGGG GGTCAAAAGC CAAGGCTTCC CAGGTCACGA TGTAGGGGAC
3701  CTGGTCTGGG TGTCCATGCG GCCAGGTGA AAAGACCTTG ATCTTAACCT
3751  GGGTGATGAG GTCTCGGTTA AAGGTGCCGT CTCGCGGCCA TCCGACGTTA
3801  AAGGTTGGCC ATTCTGCAGA GCAGAAGGTA ACCCAACGTC TCTTCTTGAC
3851  ATCTACCGAC TGGTTGTGAG CGAGCCGCTC GACATCTTTC CAGTGATCTA
3901  AGGTCAAACT TAAGGGAGTG GTAACAGTCT GGCCCTAATT TTCAGACAAA
3951  TACAGAAACA CAGTCAGACA GAGACAACAC AGAACGATGC TGCAGCAGAC
4001  AAGACGCGCG GCTTCGGTTC CAAACCGAAA GCAAAAATTC AGACGGAGGC
4051  GGGAACTGTT TTAGGTTCTC GTCTCCTACC AGAACCACAT ATCCTGACGG
4101  GGTCGGATTC CACATCGACT CCCTTCCTCA GGTCGGGCCA CAAAAACGGC
4151  CCCCAAAGTC CCTGGGACGT CTCCCAGGGT TGCGGCCGGG TGTTCAGAAC
4201  TCGTCAGTTC CACCACGGGT CCGCCAGATA CAGAGCTAGT TAGCTAACTA
4251  GTACCGACGC AGGCGCATAA AATCAGTCAT AGACACTAGA CAATCGGACA
4301  GACACAGATA AGTTGCTGGC CAGCTTACCT CCCGGTGGTG GGTCGGTGGT
4351  CCCTGGGCAG GGGTCTCCCG ATCCCGGACG AGCCCCCAAA TGAAAGACCC
4401  CCGCTGACGG GTAGTCAATC ACTCAGAGGA GACCCTCCCA AGGAACAGCG
4451  AGACCACAAG TCGGATGCAA CTGCAAGAGG GTTTATTGGA TACACGGGTA
4501  CCCGGGCGAC TCAGTCAATC GGAGGACTGG CGCCCCGAGT GAGGGGTTGT
4551  GGGCTCTTTT ATTGAGCTCG GGGAGCAGAA GCGCGCGAAC AGAAGCGAGA
4601  AGCGAACTGA TTGGTTAGTT CAAATAAGGC ACAGGGTCAT TTCAGGTCCT
4651  TGGGCACCC TGGAAACATC TGATGGTTCT CTAGAAACTG CTGAGGGCTG
4701  GACCGCATCT GGGGACCATC TGTTCTTGGC CCTGAGCCGG GGCAGGAACT
4751  GCTTACCACA GATATCCTGT TTGGCCCATA TTCAGCTGTT CCATCTGTTC
4801  TTGGCCCTGA GCCGGGCAG GAACTGCTTA CCACAGATAT CCTGTTTGGC
4851  CCATATTCAG GCTGCAGGTG GCACTTTTCG GGGAAATGTG CGCGGAACCC
4901  CTATTTGTTT ATTTTTCTAA ATACATTCAA ATATGTATCC GCTCATGAGA
4951  CAATAACCCT GATAAATGCT TCAATAATAT TGAAAAGGA AGAGTATGAG
5001  TATTCAACAT TTCCGTGTCG CCCTTATTCC CTTTTTTGCG GCATTTTGCC
5051  TTCCTGTTTT TGCTCACCCA GAAACGCTGG TGAAAGTAAA AGATGCTGAA
5101  GATCAGTTGG GTGCACGAGT GGGTTACATC GAACTGGATC TCAACAGCGG
5151  TAAGATCCTT GAGAGTTTTC GCCCCGAAGA ACGTTTTCCA ATGATGAGCA
5201  CTTTTAAAGT TCTGCTATGT GGCGCGGTAT TATCCCGTGT TGACGCCGGG
5251  CAAGAGCAAC TCGGTCGCCG CATACACTAT TCTCAGAATG ACTTGGTTGA
5301  GTACTCACCA GTCACAGAAA AGCATCTTAC GGATGGCATG ACAGTAAGAG
5351  AATTATGCAG TGCTGCCATA ACCATGAGTG ATAACACTGC GGCCAACTTA
5401  CTTCTGACAA CGATCGGAGG ACCGAAGGAG CTAACCGCTT TTTTGCACAA
5451  CATGGGGGAT CATGTAACTC GCCTTGATCG TTGGGAACCG GAGCTGAATG
5501  AAGCCATACC AAACGACGAG CGTGACACCA CGATGCCTGT AGCAATGGCA
5551  ACAACGTTGC GCAAACTATT AACTGGCGAA CTACTTACTC TAGCTTCCCG
5601  GCAACAATTA ATAGACTGGA TGGAGGCGGA TAAAGTTGCA GGACCACTTC
5651  TGCGCTCGGC CCTTCCGGCT GGCTGGTTTA TTGCTGATAA ATCTGGAGCC
5701  GGTGAGCGTG GGTCTCGCGG TATCATTGCA GCACTGGGGC CAGATGGTAA
5751  GCCCTCCCGT ATCGTAGTTA TCTACACGAC GGGGAGTCAG GCAACTATGG
```

Fig. 22-b

```
5801  ATGAACGAAA TAGACAGATC GCTGAGATAG GTGCCTCACT GATTAAGCAT
5851  TGGTAACTGT CAGACCAAGT TTACTCATAT ATACTTTAGA TTGATTTGCG
5901  GCCGGCCGCA AACTTCATTT TTAATTTAAA AGGATCTAGG TGAAGATCCT
5951  TTTTGATAAT CTCATGACCA AAATCCCTTA ACGTGAGTTT TCGTTCCACT
6001  GAGCGTCAGA CCCCGTAGAA AAGATCAAAG GATCTTCTTG AGATCCTTTT
6051  TTTCTGCGCG TAATCTGCTG CTTGCAAACA AAAAAACCAC CGCTACCAGC
6101  GGTGGTTTGT TTGCCGGATC AAGAGCTACC AACTCTTTTT CCGAAGGTAA
6151  CTGGCTTCAG CAGAGCGCAG ATACCAAATA CTGTCCTTCT AGTGTAGCCG
6201  TAGTTAGGCC ACCACTTCAA GAACTCTGTA GCACCGCCTA CATACCTCGC
6251  TCTGCTAATC CTGTTACCAG TGGCTGCTGC CAGTGGCGAT AAGTCGTGTC
6301  TTACCGGGTT GGACTCAAGA CGATAGTTAC CGGATAAGGC GCAGCGGTCG
6351  GGCTGAACGG GGGGTTCGTG CACACAGCCC AGCTTGGAGC GAACGACCTA
6401  CACCGAACTG AGATACCTAC AGCGTGAGCT ATGAGAAAGC GCCACGCTTC
6451  CCGAAGGGAG AAAGGCGGAC AGGTATCCGG TAAGCGGCAG GGTCGGAACA
6501  GGAGAGCGCA CGAGGGAGCT TCCAGGGGGA AACGCCTGGT ATCTTTATAG
6551  TCCTGTCGGG TTTCGCCACC TCTGACTTGA GCGTCGATTT TTGTGATGCT
6601  CGTCAGGGGG GCGGAGCCTA TGGAAAAACG CCAGCAACGC GGCCTTTTTA
6651  CGGTTCCTGG CCTTTTGCTG GCCTTTTGCT CACATGTTCT TTCCTGCGTT
6701  ATCCCCTGAT TCTGTGGATA ACCGTATTAC CGCCTTTGAG TGAGCTGATA
6751  CCGCTCGCCG CAGCCGAACG ACCGAGCGCA GCGAGTCAGT GAGCGAGGAA
6801  GCGGAAGAGC GCCAATACGC AAACCGCCTC TCCCCGCGCG TTGGCCGATT
6851  CATTAATGCA ACTATGGCCA TTTAATGTAA ATACTTAAGA AAAAAAACCA
6901  AATTAATTTT GATACATGCT GCATGTGAAG ACCCCGCTG ACGGGTAGTC
6951  AATCACTCAG AGGAGACCCT CCCAAGGCAG CGAGACCACA AGTCGGAAAT
7001  GAAAGACCCC CGCTGACGGG TAGTCAATCA CTCAGAGGAG ACCCTCCCAA
7051  GGAACAGCGA GACCACAAGT CGGATGCAAC TGCAAGAGGG TTTATTGGAT
7101  ACACGGGTAC CCGGGCGACT CAGTCAATCG GAGGACTGGC GCCCCGAGTG
7151  AGGGGTTGTG GGCTCTTTTA TTGAGCTCGG GGAGCAGAAG CGCGCGAACA
7201  GAAGCGAGAA GCGAACTGAT TGGTTAGTTC AAATAAGGCA CAGGGTCATT
7251  TCAGGTCCTT GGGGCACCCT GGAAACATCT GATGGTTCTC TAGAAACTGC
7301  TGAGGGCTGG ACCGCATCTG GGACCATCT GTTCTTGGCC CTGAGCCGGG
7351  GCAGGAACTG CTTACCACAG ATATCCTGTT TGGCCCATAT TCAGCTGTTC
7401  CATCTGTTCT TGGCCCTGAG CCGGGGCAGG AACTGCTTAC CACAGATATC
7451  CTGTTGGCC CATATTCAGC TGTTCCATCT GTTCCTGACC TTGATCTGAA
7501  CTTCTCTATT CTCAGTTATG TATTTTTCCA TGCCTTGCAA AATGGCGTTA
7551  CTTAAGCTAG CAGATCTGCT AGCTTGCCAA ACCTACAGGT GGGGTCTTTC
7601  ATTCCCCCCT TTTTCTGGAG ACTAAATAAA ATCTTTTATT TTATGCGCAC
7651  ATTTCCCCGA AAAGTGCCAC CTGACGTCTA AGAAACCATT ATTATCATGA
7701  CATTAACCTA TAAAAATAGG CGTATCACGA GGCCCTTTCG TCCGCACATT
7751  TCCCGAAAA GTGCCACCTG ACGTCTAAGA AACCATTATT ATCATGACAT
7801  TAACCTATAA AAATAGGCGT ATCACGAGGC CCTTTCGTCC
```

Fig. 22-c pRetroOFF-U19tsa58  Length: 8852

```
   1 TCGAGTTTAC CACTCCCTAT CAGTGATAGA GAAAAGTGAA AGTCGAGTTT
  51 ACCACTCCCT ATCAGTGATA GAGAAAAGTG AAAGTCGAGT TTACCACTCC
 101 CTATCAGTGA TAGAGAAAGT GAAAGTCGAG TTTACCACTC CCTATCAGTG
 151 ATAGAGAAAA GTGAAAGTCG AGTTTACCAC TCCCTATCAG TGATAGAGAA
 201 AAGTGAAAGT CGAGTTTACC ACTCCCTATC AGTGATAGAG AAAAGTGAAG
 251 TCGAGTTTAC CACTCCCTAT CAGTGATAGA GAAAAGTGAA AGTCGAGCTC
 301 GGTACCCGGG TCGAGTAGGC GTGTACGGTG GGAGGCCTAT ATAAGCAGAG
 351 CTCGTTTAGT GAACCGTCAG ATCGCCTGGA GACGCCATCC ACGCTGTTTT
 401 GACCTCCATA GAAGACACCG GACCGATCC AGCCTGCGGC CGCTTAATTA
 451 AGTTTAAACG GATCCxxxxx xxxxxxatgc catctagtga tgatgaggct
 501 actgctgact ctcaacattc tactcctcca aaaaagaaga gaaaggtaga
 551 agacccccaag gactttcctt cagaattgct aagttttttg agtcatgctg
 601 tgtttagtaa tagaactctt gcttgctttg ctatttacac cacaaaggaa
 651 aaagctgcac tgctatacaa gaaaattatg gaaaaatatt ctgtaacctt
 701 tataagtagg cataacagtt ataatcataa catactgttt tttcttactc
 751 cacacaggca tagagtgtct gctattaata actatgctca aaaattgtgt
 801 acctttagct ttttaatttg taaaggggtt aataaggaat atttgatgta
 851 tagtgccttg actagagatc cattttctgt tattgaggaa agtttgccag
 901 gtgggttaaa ggagcatgat tttaatccag aagaagcaga ggaaactaaa
 951 caagtgtcct ggaagcttgt aacagagtat gcaatggaaa caaaatgtga
1001 tgatgtgttg ttattgcttg ggatgtactt ggaatttcag tacagttttg
1051 aaatgtgttt aaaatgtatt aaaaagaac agcccagcca ctataagtac
1101 catgaaaagc attatgcaaa tgctgctata tttgctgaca gcaaaaacca
1151 aaaaaccata tgccaacagg ctgttgatac tgttttagct aaaaagcggg
1201 ttgatagcct acaattaact agagaacaaa tgttaacaaa cagatttaat
1251 gatcttttgg ataggatgga tataatgttt ggttctacag gctctgctga
1301 catagaagaa tggatggctg gagttgcttg gctacactgt tgttgccca
1351 aaatggattc agtggtgtat gacttttaa aatgcatggt gtacaacatt
1401 cctaaaaaaa gatactggct gtttaaagga ccaattgata gtggtaaaac
1451 tacattagca gctgctttgc ttgaattatg tgggggaaa gctttaaatg
1501 ttaatttgcc cttggacagg ctgaactttg agctaggagt agctattgac
1551 cagtttttag tagtttttga ggatgtaaag ggcactggag gggagtccag
1601 agatttgcct tcaggtcagg gaattaataa cctggacaat ttaagggatt
1651 atttggatgg cagtgttaag gtaaacttag aaaagaaaca cctaaataaa
1701 agaactcaaa tatttccccc tggaatagtc accatgaatg agtacagtgt
1751 gcctaaaaca ctgcaggcca gatttgtaaa acaaatagat tttaggccca
1801 aagattattt aaagcattgc ctggaacgca gtgagttttt gttagaaaag
1851 agaataattc aaagtggcat tgctttgctt cttatgttaa tttggtacag
1901 acctgtggct gagtttgctc aaagtattca gagcagaatt gtggagtgga
1951 aagagagatt ggacaaagag tttagtttgt cagtgtatca aaaaatgaag
2001 tttaatgtgg ctatgggaat tggagtttta gattggctaa gaaacagtga
2051 tgatgatgat gaagacagcc aggaaaatgc tgataaaaat gaagatggtg
2101 gggagaagaa catggaagac tcagggcatg aaacaggcat tgattcacag
2151 tcccaaggct catttcaggc ccctcagtcc tcacagtctg ttcatgatca
2201 taatcagcca taccacattt gtagaggttt tacttgcttt aaaaaacctc
2251 ccacacctcc ccctgaacct gaaacataax xxxxxxxxx ggatccCCCG
2301 GGAACAACAA CAATTGCATT CATTTTATGT TTCAGGTTCA GGGGGAGGTG
2351 TGGGAGGTTT TTTAAAGCAA GTAAAACCTC TACAAATGTG GTATGGCTGA
2401 TTATGATCCT GCAAGCCTCG TCGTCTGGCC GGACCACGCT ATCTGTGCAA
2451 GGTCCCCGGA CGCGCGCTCC ATGAGCAGAG CGTCGCGCCC CTACCCACC
2501 GTACTCGTCA ATTCCAAGGG CATCGGTAAA CAGAGCGCCG TAGGGGGCGG
2551 AGTCGTGGGG GGTAAATCCC GGACCCGGGG AATCCCGTC CCCAACATG
2601 TCCAGATCGA AATCGTCTAG CGCGTCGGCA TGCGCCATCG CCACGTCCTC
2651 GCCGTATAAG TGGAGCTCGT CCCCCAGGCT GACATCGGTC GGGGGGGCCG
2701 TCGACAGTCT GCGCGTGTGT CCGCGGGGAG AAAGGACAGG CGCGGAGCCG
2751 CCAGCCCGC CTCTTCGGGG GCGTCGTCGT CCGGGAGATC GAGCAGGCCC
2801 TCGATGGTAG ACCCGTAATT GTTTTCGTA CGCGCGCGGC TGTACGCGGA
2851 CCCACTTTCA CATTTAAGTT GTTTTTCTAA TCCGCATATG ATCAATTCAA
```

Fig. 23-a

```
2901  GGCCGAATAA AAGGCTGGC TCTGCACCTT GGTGATCAAA TAATTCGATA
2951  GCTTGTCGTA ATAATGGCGG CATACTATCA GTAGTAGGTG TTTCCCTTTC
3001  TTCTTTAGCG ACTTGATGCT CTTGATCTTC CAATACGCAA CCTAAAGTAA
3051  AATGCCCCAC AGCGCTGAGT GCATATAATG CATTCTCTAG TGAAAAACCT
3101  TGTTGGCATA AAAAGGCTAA TTGATTTTCG AGAGTTTCAT ACTGTTTTTC
3151  TGTAGGCCGT GTACCTAAAT GTACTTTTGC TCCATCGCGA TGACTTAGTA
3201  AAGCACATCT AAAACTTTTA GCGTTATTAC GTAAAAAATC TTGCCAGCTT
3251  TCCCCTTCTA AAGGGCAAAA GTGAGTATGG TGCCTATCTA ACATCTCAAT
3301  GGCTAAGGCG TCGAGCAAAG CCCGCTTATT TTTACATGC CAATACAATG
3351  TAGGCTGCTC TACACCTAGC TTCTGGGCGA GTTTACGGGT TGTTAAACCT
3401  TCGATTCCGA CCTCATTAAG CAGCTCTAAT GCGCTGTTAA TCACTTTACT
3451  TTTATCTAAT CTAGACATGG TGGAAGCTTT TTGCAAAAGC CTAGGCCTCC
3501  AAAAAAGCCT CCTCACTACT TCTGGAATAG CTCAGAGGCC GAGGCGGCCT
3551  CGGCCTCTGC ATAAATAAAA AAAATTAGTC AGCCATGGGG CGGAGAATGG
3601  GCGGAACTGG GCGGAGTTAG GGGCGGGATG GCGGAGTTA GGGGCGGGAC
3651  TATGGTTGCT GACTAATTGA GATGCATGCT TTGCATACTT CTGCCTGCTG
3701  GGGAGCCTGG GGACTTTCCA CACCTGGTTG CTGACTAATT GAGATGCATG
3751  CTTTGCATAC TTCTGCCTGC TGGGGAGCCT GGGGACTTTC CACACCCTAA
3801  CTGACACACA TTCCACAGGT CGACTAGATC GAATTCTCAA TTGTTTTACG
3851  CGGCCCGATG CATGGGGTCG TGCGCTCCTT TCGGTCGGGC GCTGCGGGTC
3901  GTGGGGCGGG CGTCAGGCAC CGGGCTTGCG GGTCATGCAC CAGGTCGCGC
3951  GGTCCTTCGG GCACTCGACG TCGGCGGTGA CGGTGAAGCC GAGCCGCTCG
4001  TAGAAGGGGA GGTTGCGGGG CGCGGAGGTC TCCAGGAAGG CGGGCACCCC
4051  GGCGCGCTCG GCCGCCTCCA CTCCGGGGAG CACGACGGCG CTGCCCAGAC
4101  CCTTGCCCTG GTGGTCGGGC GAGACGCCGA CGGTGGCCAG GAACCACGCG
4151  GGCTCCTTGG GCCGGTGCGG CGCCAGGAGG CCTTCCATCT GTTGCTGCGC
4201  GGCCAGCCGG GAACCGCTCA ACTCGGCCAT GCGCGGGCCG ATCTCGGCGA
4251  ACACCGCCCC CGCTTCGACG CTCTCCGGCG TGGTCCAGAC CGCCACCGCG
4301  GCGCCGTCGT CCGCGACCCA CACCTTGCCG ATGTCGAGCC CGACGCGCGT
4351  GAGGAAGAGT TCTTGCAGCT CGGTGACCCG CTCGATGTGG CGGTCCGGAT
4401  CGACGGTGTG GCGCGTGGCG GGGTAGTCGG CGAACGCGGC GGCGAGGGTG
4451  CGTACGGCCC TGGGGACGTC GTCGCGGGTG GCGAGGCGCA CCGTGGGCTT
4501  GTACTCGGTC ATGGTAAGCT GATCCGGCCG GCGCCTAGAG AAGGAGTGAG
4551  GGCTGGATAA AGGGAGGATT GAGGCGGGGT CGAAAGAGGA GGTTCAAGGG
4601  GGAGAGACGG CGCGGATGGA AGAAGAGGAG GCGGAGGCTT AGGGTGTACA
4651  AAGGGCTTGA CCCAGGGAGG GGGGTCAAAA GCCAAGGCTT CCCAGGTCAC
4701  GATGTAGGGG ACCTGGTCTG GGTGTCCATG CGGGCCAGGT GAAAAGACCT
4751  TGATCTTAAC CTGGGTGATG AGGTCTCGGT TAAAGGTGCC GTCTCGCGGC
4801  CATCCGACGT TAAAGGTTGG CCATTCTGCA GAGCAGAAGG TAACCCAACG
4851  TCTCTTCTTG ACATCTACCG ACTGGTTGTG AGCGAGCCGC TCGACATCTT
4901  TCCAGTGATC TAAGGTCAAA CTTAAGGGAG TGGTAACAGT CTGGCCCTAA
4951  TTTTCAGACA AATACAGAAA CACAGTCAGA CAGAGACAAC ACAGAACGAT
5001  GCTGCAGCAG ACAAGACGCG CGGCTTCGGT TCCAAACCGA AAGCAAAAAT
5051  TCAGACGGAG GCGGAACTG TTTTAGGTTC TCGTCTCCTA CCAGAACCAC
5101  ATATCCTGAC GGGGTCGGAT TCCACATCGA CTCCCTTCCT CAGGTCGGGC
5151  CACAAAAACG GCCCCCAAAG TCCCTGGGAC GTCTCCCAGG GTTGCGGCCG
5201  GGTGTTCAGA ACTCGTCAGT TCCACCACGG GTCCGCCAGA TACAGAGCTA
5251  GTTAGCTAAC TAGTACCGAC GCAGGCGCAT AAAATCAGTC ATAGACACTA
5301  GACAATCGGA CAGACACAGA TAAGTTGCTG GCCAGCTTAC CTCCCGGTGG
5351  TGGGTCGGTG GTCCCTGGGC AGGGGTCTCC CGATCCCGGA CGAGCCCCCA
5401  AATGAAAGAC CCCCGCTGAC GGGTAGTCAA TCACTCAGAG GAGACCCTCC
5451  CAAGGAACAG CGAGACCACA AGTCGGATGC AACTGCAAGA GGGTTTATTG
5501  GATACACGGG TACCCGGGCG ACTCAGTCAA TCGGAGGACT GGCGCCCCGA
5551  GTGAGGGGTT GTGGCTCTT TTATTGAGCT CGGGGAGCAG AAGCGCGCGA
5601  ACAGAAGCGA GAAGCGAACT GATTGGTTAG TTCAAATAAG GCACAGGGTC
5651  ATTTCAGGTC CTTGGGGCAC CCTGGAAACA TCTGATGGTT CTCTAGAAAC
5701  TGCTGAGGGC TGGACCGCAT CTGGGGACCA TCTGTTCTTG GCCCTGAGCC
5751  GGGGCAGGAA CTGCTTACCA CAGATATCCT GTTTGGCCCA TATTCAGCTG
5801  TTCCATCTGT TCTTGGCCCT GAGCCGGGGC AGGAACTGCT TACCACAGAT
5851  ATCCTGTTTG GCCCATATTC AGGCTGCAGG TGGCACTTTT CGGGGAAATG
```

Fig. 23-b

```
5901  TGCGCGGAAC CCCTATTTGT TTATTTTTCT AAATACATTC AAATATGTAT
5951  CCGCTCATGA GACAATAACC CTGATAAATG CTTCAATAAT ATTGAAAAAG
6001  GAAGAGTATG AGTATTCAAC ATTTCCGTGT CGCCCTTATT CCCTTTTTTG
6051  CGGCATTTTG CCTTCCTGTT TTTGCTCACC CAGAAACGCT GGTGAAAGTA
6101  AAAGATGCTG AAGATCAGTT GGGTGCACGA GTGGGTTACA TCGAACTGGA
6151  TCTCAACAGC GGTAAGATCC TTGAGAGTTT TCGCCCCGAA GAACGTTTTC
6201  CAATGATGAG CACTTTTAAA GTTCTGCTAT GTGGCGCGGT ATTATCCCGT
6251  GTTGACGCCG GGCAAGAGCA ACTCGGTCGC CGCATACACT ATTCTCAGAA
6301  TGACTTGGTT GAGTACTCAC CAGTCACAGA AAAGCATCTT ACGGATGGCA
6351  TGACAGTAAG AGAATTATGC AGTGCTGCCA TAACCATGAG TGATAACACT
6401  GCGGCCAACT TACTTCTGAC AACGATCGGA GGACCGAAGG AGCTAACCGC
6451  TTTTTTGCAC AACATGGGGG ATCATGTAAC TCGCCTTGAT CGTTGGGAAC
6501  CGGAGCTGAA TGAAGCCATA CCAAACGACG AGCGTGACAC CACGATGCCT
6551  GTAGCAATGG CAACAACGTT GCGCAAACTA TTAACTGGCG AACTACTTAC
6601  TCTAGCTTCC CGGCAACAAT TAATAGACTG GATGGAGGCG GATAAAGTTG
6651  CAGGACCACT TCTGCGCTCG GCCCTTCCGG CTGGCTGGTT TATTGCTGAT
6701  AAATCTGGAG CCGGTGAGCG TGGGTCTCGC GGTATCATTG CAGCACTGGG
6751  GCCAGATGGT AAGCCCTCCC GTATCGTAGT TATCTACACG ACGGGGAGTC
6801  AGGCAACTAT GGATGAACGA AATAGACAGA TCGCTGAGAT AGGTGCCTCA
6851  CTGATTAAGC ATTGGTAACT GTCAGACCAA GTTTACTCAT ATATACTTTA
6901  GATTGATTTG CGGCCGGCCG CAAACTTCAT TTTTAATTTA AAAGGATCTA
6951  GGTGAAGATC CTTTTTGATA ATCTCATGAC CAAAATCCCT TAACGTGAGT
7001  TTTCGTTCCA CTGAGCGTCA GACCCCGTAG AAAAGATCAA AGGATCTTCT
7051  TGAGATCCTT TTTTTCTGCG CGTAATCTGC TGCTTGCAAA CAAAAAAACC
7101  ACCGCTACCA GCGGTGGTTT GTTTGCCGGA TCAAGAGCTA CCAACTCTTT
7151  TTCCGAAGGT AACTGGCTTC AGCAGAGCGC AGATACCAAA TACTGTCCTT
7201  CTAGTGTAGC CGTAGTTAGG CCACCACTTC AAGAACTCTG TAGCACCGCC
7251  TACATACCTC GCTCTGCTAA TCCTGTTACC AGTGGCTGCT GCCAGTGGCG
7301  ATAAGTCGTG TCTTACCGGG TTGGACTCAA GACGATAGTT ACCGGATAAG
7351  GCGCAGCGGT CGGGCTGAAC GGGGGGTTCG TGCACACAGC CCAGCTTGGA
7401  GCGAACGACC TACACCGAAC TGAGATACCT ACAGCGTGAG CTATGAGAAA
7451  GCGCCACGCT TCCCGAAGGG AGAAAGGCGG ACAGGTATCC GGTAAGCGGC
7501  AGGGTCGGAA CAGGAGAGCG CACGAGGGAG CTTCCAGGGG GAAACGCCTG
7551  GTATCTTTAT AGTCCTGTCG GGTTTCGCCA CCTCTGACTT GAGCGTCGAT
7601  TTTTGTGATG CTCGTCAGGG GGGCGGAGCC TATGGAAAAA CGCCAGCAAC
7651  GCGGCCTTTT TACGGTTCCT GGCCTTTTGC TGGCCTTTTG CTCACATGTT
7701  CTTTCCTGCG TTATCCCCTG ATTCTGTGGA TAACCGTATT ACCGCCTTTG
7751  AGTGAGCTGA TACCGCTCGC CGCAGCCGAA CGACCGAGCG CAGCGAGTCA
7801  GTGAGCGAGG AAGCGGAAGA GCGCCAATAC GCAAACCGCC TCTCCCCGCG
7851  CGTTGGCCGA TTCATTAATG CAACTATGGC CATTTAATGT AAATACTTAA
7901  GAAAAAAAAC CAAATTAATT TTGATACATG CTGCATGTGA AGACCCCCGC
7951  TGACGGGTAG TCAATCACTC AGAGGAGACC CTCCCAAGGC AGCGAGACCA
8001  CAAGTCGGAA ATGAAAGACC CCCGCTGACG GGTAGTCAAT CACTCAGAGG
8051  AGACCCTCCC AAGGAACAGC GAGACCACAA GTCGGATGCA ACTGCAAGAG
8101  GGTTTATTGG ATACACGGGT ACCCGGCGA CTCAGTCAAT CGGAGGACTG
8151  GCGCCCCGAG TGAGGGGTTG TGGGCTCTTT TATTGAGCTC GGGGAGCAGA
8201  AGCGCGCGAA CAGAAGCGAG AAGCGAACTG ATTGGTTAGT TCAAATAAGG
8251  CACAGGGTCA TTTCAGGTCC TTGGGGCACC CTGGAAACAT CTGATGGTTC
8301  TCTAGAAACT GCTGAGGGCT GGACCGCATC TGGGGACCAT CTGTTCTTGG
8351  CCCTGAGCCG GGGCAGGAAC TGCTTACCAC AGATATCCTG TTTGGCCCAT
8401  ATTCAGCTGT TCCATCTGTT CTTGGCCCTG AGCCGGGGCA GGAACTGCTT
8451  ACCACAGATA TCCTGTTTGG CCCATATTCA GCTGTTCCAT CTGTTCCTGA
8501  CCTTGATCTG AACTTCTCTA TTCTCAGTTA TGTATTTTTC CATGCCTTGC
8551  AAAATGGCGT TACTTAAGCT AGCAGATCTG CTAGCTTGCC AAACCTACAG
8601  GTGGGGTCTT TCATTCCCCC CTTTTCTGG AGACTAAATA AAATCTTTTA
8651  TTTTATGCGC ACATTTCCCC GAAAAGTGCC ACCTGACGTC TAAGAAACCA
8701  TTATTATCAT GACATTAACC TATAAAAATA GGCGTATCAC GAGGCCCTTT
8751  CGTCCGCACA TTTCCCCGAA AAGTGCCACC TGACGTCTAA GAAACCATTA
8801  TTATCATGAC ATTAACCTAT AAAAATAGGC GTATCACGAG GCCCTTTCGT
8851  CC
```

Fig. 23-c puhd10-3-hIL3   Length: 3621
```
   1 ctcgagttta ccactcccta tcagtgatag agaaaagtga aagtcgagtt
  51 taccactccc tatcagtgat agagaaaagt gaaagtcgag tttaccactc
 101 cctatcagtg atagagaaaa gtgaaagtcg agtttaccac tccctatcag
 151 tgatagagaa aagtgaaagt cgagtttacc actccctatc agtgatagag
 201 aaaagtgaaa gtcgagttta ccactcccta tcagtgatag agaaaagtga
 251 aagtcgagtt taccactccc tatcagtgat agagaaaagt gaaagtcgag
 301 ctcggtaccc gggtcgagta ggcgtgtacg gtgggaggcc tatataagca
 351 gagctcgttt agtgaaccgt cagatcgcct ggagacgcca tccacgctgt
 401 tttgacctcc atagaagaca ccgggaccga tccagcctcc gcggccccga
 451 attaaacagt cgagctacgt caacgaaaaa taaaatccaa acatgagccg
 501 cctgcccgtc ctgctcctgc tccaactcct ggtccgcccc ggactccaag
 551 ctcccatgac ccagacaacg tccttgaaga caagctgggt taactgctct
 601 aacatgatcg atgaaattat aacacactta aagcagccac ctttgccttt
 651 gctggacttc aacaacctca atggggaaga ccaagacatt ctgatggaaa
 701 ataaccttcg aaggccaaac tggaggcat caacagggc tgtcaagagt
 751 ttacagaacg catcagcaat tgagagcatt cttaaaaatc tcctgccatg
 801 tctgccctg gccacggccg cacccacgcg acatccaatc catatcaagg
 851 acggtgactg gaatgaattc cggaggaaac tgacgttcta tctgaaaacc
 901 cttgagaatg cgcaggctca acagacgact ttgagcctcg cgatcttta
 951 gaactcgact ctagacatga taagatacat tgatgagttt ggacaaacca
1001 caactagaat gcagtgaaaa aaatgcttta tttgtgaaat ttgtgatgct
1051 attgctttat ttgtaaccat tataagctgc aataaacaag ttaacaacaa
1101 caattgcatt cattttatgt ttcaggttca gggggaggtg tgggaggttt
1151 tttaaagcaa gtaaaacctc tacaaatgtg gtatggctga ttatgatcct
1201 gcaagcctcg tcgtctggcc ggaccacgct atctgtgcaa ggtccccgga
1251 cgcgcgctcc atgagcagag cgcccgccgc cgaggcaaga ctcgggcggc
1301 gccctgcccg tcccaccagg tcaacaggcg gtaaccggcc tcttcatcgg
1351 gaatgcgcgc gaccttcagc atcgccggca tgtccctgg cggacgggaa
1401 gtatcagctc gaccaagctt ggcgagattt tcaggagcta aggaagctaa
1451 aatggagaaa aaatcactg gatataccac cgttgatata tcccaatggc
1501 atcgtaaaga acattttgag gcatttcagt cagttgctca atgtacctat
1551 aaccagaccg ttcagctgca ttaatgaatc ggccaacgcg cggggagagg
1601 cggtttgcgt attgggcgct cttccgcttc ctcgctcact gactcgctgc
1651 gctcggtcgt tcggctgcgg cgagcggtat cagctcactc aaagtcggta
1701 atacggttat ccacagaatc aggggataac gcaggaaaga acatgtgagc
1751 aaaaggccag caaaaggcca ggaaccgtaa aaaggccgcg ttgctggcgt
1801 ttttccatag gctccgcccc ctgacgagc atcacaaaaa tcgacgctca
1851 agtcagaggt ggcgaaaccc gacaggacta taaagatacc aggcgtttcc
1901 ccctggaagc tccctcgtgc gctctcctgt tccgaccctg ccgcttaccg
1951 gatacctgtc cgcctttctc ccttcgggaa gcgtggcgct ttctcaatgc
2001 tcacgctgta ggtatctcag ttcggtgtag gtcgttcgct ccaagctggg
2051 ctgtgtgcac gaaccccccg ttcagcccga ccgctgcgcc ttatccggta
2101 actatcgtct tgagtccaac ccggtaagac acgacttatc gccactggaa
2151 gcagccactg gtaacaggat tagcagagcg aggtatgtag gcggtgctac
2201 agagttcttg aagtggtggc ctaactacgg ctacactaga aggacagtat
2251 ttggtatctg cgctctgctg aagccagtta ccttcggaaa aagagttggt
2301 agctcttgat ccggcaaaca aaccaccgct ggtagcggtg gtttttttgt
2351 ttgcaagcag cagattacgc gcagaaaaaa aggatctcaa gaagatcctt
2401 tgatcttttc tacggggtct gacgctcagt ggaacgaaaa ctcacgttaa
2451 gggattttgg tcatgagatt atcaaaaagg atcttcacct agatcctttt
2501 aaattaaaaa tgaagtttta aatcaatcta agtatatat gagtaaactt
2551 ggtctgacag ttaccaatgc ttaatcagtg aggcacctat ctcagcgatc
2601 tgtctatttc gttcatccat agttgcctga ctccccgtcg tgtagataac
2651 tacgatacgg gagggcttac catctggccc cagtgctgca atgataccgc
2701 gagacccacg ctcaccggct ccagatttat cagcaataaa ccagccagcc
2751 ggaagggccg agcgcagaag tggtcctgca actttatccg cctccatcca
2801 gtctattaat tgttgccggg aagctagagt aagtagttcg ccagttaata
2851 gtttgcgcaa cgttgttgcc attgctacag gcatcgtgtg gtcacgctcg
```
Fig. 24-a

```
2901  tcgtttggta tggcttcatt cagctccggt tcccaacgat caaggcgagt
2951  tacatgatcc cccatgttgt gcaaaaaagc ggttagctcc ttcggtcctc
3001  cgatcgttgt cagaagtaag ttggccgcag tgttatcact catggttatg
3051  gcagcactgc ataattctct tactgtcatg ccatccgtaa gatgcttttc
3101  tgtgactggt gagtactcaa ccaagtcatt ctgagaatag tgtatgcggc
3151  gaccgagttg ctcttgcccg tcgtcaatac gggataatac cgcgccacat
3201  agcagaactt taaaagtgct catcattgga aaacgttctt cggggcgaaa
3251  actctcaagg atcttaccgc tgttgagatc cagttcgatg taacccactc
3301  gtgcacccaa ctgatcttca gcatctttta ctttcaccag cgtttctggg
3351  tgagcaaaaa caggaaggca aaatgccgca aaaagggaa taagggcgac
3401  acggaaatgt tgaatactca tactcttcct ttttcaatat tattgaagca
3451  tttatcaggg ttattgtctc atgagcggat acatatttga atgtatttag
3501  aaaaataaac aaatagtggt tccgcgcaca tttccccgaa aagtgccacc
3551  tgacgtctaa gaaaccatta ttatcatgac attaacctat aaaaataggc
3601  gtatcacgag gccctttcgt c
```

Fig. 24-b pUHD10-3-hIL6
Length: 3752   June 22, 1999 10:32   Type: N   Check: 8139

```
   1 ctcgagttta ccactcccta tcagtgatag agaaaagtga aagtcgagtt
  51 taccactccc tatcagtgat agagaaaagt gaaagtcgag tttaccactc
 101 cctatcagtg atagagaaaa gtgaaagtcg agtttaccac tccctatcag
 151 tgatagagaa aagtgaaagt cgagtttacc actccctatc agtgatagag
 201 aaaagtgaaa gtcgagttta ccactcccta tcagtgatag agaaaagtga
 251 aagtcgagtt taccactccc tatcagtgat agagaaaagt gaaagtcgag
 301 ctcggtaccc gggtcgagta ggcgtgtacg gtgggaggcc tatataagca
 351 gagctcgttt agtgaaccgt cagatcgcct ggagacgcca tccacgctgt
 401 tttgacctcc atagaagaca ccgggaccga tccagcctcc gcggtggcgg
 451 ccgctctaga actagtggat cccccagctt acctgccatg ccagtacccc
 501 caggagaaga ttccaaagat gtagccgccc cacacagaca gccactcacc
 551 tcttcagaac gaattgacaa acaaattcgg tacatcctcg acggcatctc
 601 agccctgaga aaggagacat gtaacaagag taacatgtgt gaaagcagca
 651 aagaggcact ggcagaaaac aacctgaacc ttccaaagat ggctgaaaaa
 701 gatggatgct tccaatctgg attcaatgag gagacttgcc tggtgaaaat
 751 catcactggt cttttggagt tgaggtata cctagagtac ctccagaaca
 801 gatttgagag tagtgaggaa caagccagag ctgtccagat gagtacaaaa
 851 gtcctgatcc agttcctgca gaaaaaggca agaatctag atgcaataac
 901 caccectgac ccaaccacaa atgccagcct gctgacgaag ctgcaggcac
 951 agaaccagtg gctgcaggac atgacaactc atctcattct gcgcagcttt
1001 aaggagttcc tgcagtccag cctgagggct cttcggcaaa tgtagtaagg
1051 atccgaattc gagctcggta cccggggatc tctagagga tccagacatg
1101 ataagataca tgatgagtt tggacaaacc acaactagaa tgcagtgaaa
1151 aaaatgcttt atttgtgaaa tttgtgatgc tattgcttta tttgtaacca
1201 ttataagctg caataaacaa gttaacaaca acaattgcat tcattttatg
1251 tttcaggttc agggggaggt gtgggaggtt ttttaaagca agtaaaacct
1301 ctacaaatgt ggtatgctg attatgatcc tgcaagcctc gtcgtctggc
1351 cggaccacgc tatctgtgca aggtccccgg acgcgcgctc catgagcaga
1401 gcgccgccg ccgaggcaag actcgggcgg cgccctgccc gtcccaccag
1451 gtcaacaggc ggtaaccggc ctcttcatcg ggaatgcgcg cgaccttcag
1501 catcgccggc atgtcccctg gcggacggga agtatcagct cgaccaagct
1551 tggcgagatt tcaggagct aaggaagcta aaatggagaa aaaaatcact
1601 ggatatacca ccgttgatat atcccaatgg catcgtaaag aacatttga
1651 ggcatttcag tcagttgctc aatgtaccta taaccagacc gttcagctgc
1701 attaatgaat cggccaacgc gcggggagag gcggtttgcg tattgggcgc
1751 tcttccgctt cctcgctcac tgactcgctg cgctcggtcg ttcggctgcg
1801 gcgagcggta tcagctcact caaagtcggt aatacggtta tccacagaat
1851 caggggataa cgcaggaaag aacatgtgag caaaaggcca gcaaaaggcc
1901 aggaaccgta aaaaggccgc gttgctggcg ttttccata ggctccgccc
1951 ccctgacgag catcacaaaa atcgacgctc aagtcagagg tggcgaaacc
2001 cgacaggact ataaagatac caggcgtttc ccctggaag ctccctcgtg
2051 cgctctcctg ttccgaccct gccgcttacc ggatacctgt ccgcctttct
2101 cccttcggga agcgtggcgc tttctcaatg ctcacgctgt aggtatctca
2151 gttcggtgta ggtcgttcgc tccaagctgg ctgtgtgca cgaaccccc
2201 gttcagcccg accgctgcgc cttatccggt aactatcgtc ttgagtccaa
2251 cccggtaaga cacgacttat cgccactgga agcagccact ggtaacagga
2301 ttagcagagc gaggtatgta ggcggtgcta cagagttctt gaagtggtgg
2351 cctaactacg gctacactag aaggacagta tttggtatct gcgctctgct
2401 gaagccagtt accttcggaa aaagagttgg tagctcttga tccggcaaac
2451 aaaccaccgc tggtagcggt ggttttttg tttgcaagca gcagattacg
2501 cgcagaaaaa aaggatctca agaagatcct tgatctttt ctacggggtc
2551 tgacgctcag tggaacgaaa actcacgtta agggattttg gtcatgagat
2601 tatcaaaaag gatcttacc tagatccttt taaattaaaa atgaagtttt
2651 aaatcaatct aaagtatata tgagtaaact tggtctgaca gttaccaatg
2701 cttaatcagt gaggcaccta tctcagcgat ctgtctattt cgttcatcca
2751 tagttgcctg actccccgtc gtgtagataa ctacgatacg ggagggctta
```

Fig. 25-a

```
2801  ccatctggcc ccagtgctgc aatgataccg cgagacccac gctcaccggc
2851  tccagattta tcagcaataa accagccagc cggaagggcc gagcgcagaa
2901  gtggtcctgc aactttatcc gcctccatcc agtctattaa ttgttgccgg
2951  gaagctagag taagtagttc gccagttaat agtttgcgca acgttgttgc
3001  cattgctaca ggcatcgtgt ggtcacgctc gtcgtttggt atggcttcat
3051  tcagctccgg ttcccaacga tcaaggcgag ttacatgatc ccccatgttg
3101  tgcaaaaaag cggttagctc cttcggtcct ccgatcgttg tcagaagtaa
3151  gttggccgca gtgttatcac tcatggttat ggcagcactg cataattctc
3201  ttactgtcat gccatccgta agatgctttt ctgtgactgg tgagtactca
3251  accaagtcat tctgagaata gtgtatgcgg cgaccgagtt gctcttgccc
3301  gtcgtcaata cgggataata ccgcgccaca tagcagaact ttaaaagtgc
3351  tcatcattgg aaaacgttct cggggcgaaa actctcaag gatcttaccg
3401  ctgttgagat ccagttcgat gtaacccact cgtgcaccca actgatcttc
3451  agcatctttt actttcacca gcgtttctgg gtgagcaaaa acaggaaggc
3501  aaaatgccgc aaaaaaggga ataagggcga cacggaaatg ttgaatactc
3551  atactcttcc ttttcaata ttattgaagc atttatcagg gttattgtct
3601  catgagcgga tacatatttg aatgtattta gaaaaataaa caaatagggg
3651  ttccgcgcac atttccccga aagtgccac ctgacgtcta agaaaccatt
3701  attatcatga cattaaccta taaaaatagg cgtatcacga ggccctttcg
3751  tc
```

Fig. 25-b puhd10-3-tgf

```
        ctcgagtttaccactccctatcagtgatagagaaaagtgaaagtcgagtttaccactccc
   1    ---------+---------+---------+---------+---------+---------+  60
        tatcagtgatagagaaaagtgaaagtcgagtttaccactccctatcagtgatagagaaaa
  61    ---------+---------+---------+---------+---------+---------+  120
        gtgaaagtcgagtttaccactccctatcagtgatagagaaaagtgaaagtcgagtttacc
 121    ---------+---------+---------+---------+---------+---------+  180
        actccctatcagtgatagagaaaagtgaaagtcgagtttaccactccctatcagtgatag
 181    ---------+---------+---------+---------+---------+---------+  240
        agaaaagtgaaagtcgagtttaccactccctatcagtgatagagaaaagtgaaagtcgag
 241    ---------+---------+---------+---------+---------+---------+  300
        ctcggtacccgggtcgagtaggcgtgtacggtgggaggcctatataagcagagctcgttt
 301    ---------+---------+---------+---------+---------+---------+  360
        agtgaaccgtcagatcgcctggagacgccatccacgctgttttgacctccatagaagaca
 361    ---------+---------+---------+---------+---------+---------+  420
        ccgggaccgatccagcctccgcggccccgaattcctgcagcccATGCACTTGCAAAGGGC
 421    ---------+---------+---------+---------+---------+---------+  480
        TCTGGTAGTCCTGGCCCTGCTGAACTTGGCCACAATCAGCCTCTCTCTGTCCACTTGCAC
 481    ---------+---------+---------+---------+---------+---------+  540
        CACGTTGGACTTCGGCCACATCAAGAAGAAGAGGGTGGAAGCCATTAGGGGACAGATCTT
 541    ---------+---------+---------+---------+---------+---------+  600
        GAGCAAGCTCAGGCTCACCAGCCCCCCTGAGCCATCGGTGATGACCCACGTCCCCTATCA
 601    ---------+---------+---------+---------+---------+---------+  660
        GGTCCTGGCACTTTACAACAGCACCCGGGAGTTGCTGGAAGAGATGCACGGGGAGAGGGA
 661    ---------+---------+---------+---------+---------+---------+  720
        GGAAGGCTGCACTCAGGAGACCTCGGAGTCTGAGTACTATGCCAAAGAGATCCATAAATT
 721    ---------+---------+---------+---------+---------+---------+  780
        CGACATGATCCAGGGACTGGCGGAGCACAATGAACTGGCCGTCTGCCCCAAAGGAATTAC
 781    ---------+---------+---------+---------+---------+---------+  840
        CTCTAAGGTTTTTCGTTTCAATGTGTCCTCAGTGGAGAAAAATGGAACCAATCTGTTCCG
 841    ---------+---------+---------+---------+---------+---------+  900
        GGCAGAGTTCCGGGTCTTGCGGGTGCCCAACCCCAGCTCCAAGCGCACAGAGCAGAGAAT
 901    ---------+---------+---------+---------+---------+---------+  960
        TGAGCTCTTCCAGATACTTCGACCGGATGAGCACATAGCCAAGCAGCGCTACATAGGTGG
 961    ---------+---------+---------+---------+---------+---------+ 1020
        CAAGAATCTGCCCACAAGGGGCACCGCTGAATGGCTGTCTTTCGATGTCACTGACACTGT
1021    ---------+---------+---------+---------+---------+---------+ 1080
        GCGCGAGTGGCTGTTGAGGAGAGAGTCCAACTTGGGTCTGGAAATCAGCATCCACTGTCC
1081    ---------+---------+---------+---------+---------+---------+ 1140
        ATGTCACACCTTTCAGCCCAATGGAGACATACTGGAAAATGTTCATGAGGTGATGGAAAT
1141    ---------+---------+---------+---------+---------+---------+ 1200
        CAAATTCAAAGGAGTGGACAATGAAGATGACCATGGCCGTGGAGACCTGGGGCGTCTCAA
1201    ---------+---------+---------+---------+---------+---------+ 1260
        GAAGCAAAAGGATCACCACAACCCACACCTGATCCTCATGATGATCCCCCCACACCGACT
1261    ---------+---------+---------+---------+---------+---------+ 1320
```

Fig. 26-a

```
         GGACAGCCCAGGCCAGGGCAGTCAGAGGAAGAAGAGGGCCCTGGACACCAATTACTGCTT
1321  ---------+---------+---------+---------+---------+---------+  1380

CCGCAACCTGGAGGAGAACTGCTGTGTACGCCCCCTTTATATTGACTTCCGGCAGGATCT
1381  ---------+---------+---------+---------+---------+---------+  1440

AGGCTGGAAATGGGTCCACGAACCTAAGGGTTACTATGCCAACTTCTGCTCAGGCCCTTG
1441  ---------+---------+---------+---------+---------+---------+  1500

CCCATACCTCCGCAGCGCAGACACAACCCATAGCACGGTGCTTGGACTATACAACACCCT
1501  ---------+---------+---------+---------+---------+---------+  1560

GAACCCAGAGGCGTCTGCCTCGCCATGCTGCGTCCCCCAGGACCTGGAGCCCCTGACCAT
1561  ---------+---------+---------+---------+---------+---------+  1620

CTTGTACTATGTGGGCAGAACCCCCAAGGTGGAGCAGCTGTCCAACATGGTGGTGAAGTC
1621  ---------+---------+---------+---------+---------+---------+  1680

GTGTAAGTGCAGCTGAgggggatccactagttctagaggatccagacatgataagataca
1681  ---------+---------+---------+---------+---------+---------+  1740 ttgatgagtttggacaaaccacaactagaatgcagtgaaaaaaatgctttatttgtgaaa
1741  ---------+---------+---------+---------+---------+---------+  1800 tttgtgatgctattgctttatttgtaaccattataagctgcaataaacaagttaacaaca
1801  ---------+---------+---------+---------+---------+---------+  1860 acaattgcattcatttttatgtttcaggttcaggggggaggtgtgggaggttttttaaagca
1861  ---------+---------+---------+---------+---------+---------+  1920 agtaaaacctctacaaatgtggtatggctgattatgatcctgcaagcctcgtcgtctggc
1921  ---------+---------+---------+---------+---------+---------+  1980 cggaccacgctatctgtgcaaggtccccggacgcgcgctccatgagcagagcgcccgccg
1981  ---------+---------+---------+---------+---------+---------+  2040 ccgaggcaagactcgggcggcgccctgcccgtcccaccaggtcaacaggcggtaaccggc
2041  ---------+---------+---------+---------+---------+---------+  2100 ctcttcatcgggaatgcgcgcgaccttcagcatcgccggcatgtcccctggcggacggga
2101  ---------+---------+---------+---------+---------+---------+  2160 agtatcagctcgaccaagcttggcgagattttcaggagctaaggaagctaaaatggagaa
2161  ---------+---------+---------+---------+---------+---------+  2220 aaaaatcactggatataccaccgttgatatatcccaatggcatcgtaaagaacatttga
2221  ---------+---------+---------+---------+---------+---------+  2280 ggcatttcagtcagttgctcaatgtacctataaccagaccgttcagctgcattaatgaat
2281  ---------+---------+---------+---------+---------+---------+  2340 cggccaacgcgcggggagaggcggtttgcgtattgggcgctcttccgcttcctcgctcac
2341  ---------+---------+---------+---------+---------+---------+  2400 tgactcgctgcgctcggtcgttcggctgcggcgagcggtatcagctcactcaaagtcggt
2401  ---------+---------+---------+---------+---------+---------+  2460 aatacggttatccacagaatcaggggataacgcaggaaagaacatgtgagcaaaaggcca
2461  ---------+---------+---------+---------+---------+---------+  2520 gcaaaaggccaggaaccgtaaaaaggccgcgttgctggcgtttttccataggctccgccc
2521  ---------+---------+---------+---------+---------+---------+  2580 ccctgacgagcatcacaaaaatcgacgctcaagtcagaggtggcgaaacccgacaggact
2581  ---------+---------+---------+---------+---------+---------+  2640
```

Fig. 26-b

```
        ataaagataccaggcgtttcccoctggaagctccctcgtgcgctctcctgttccgaccct
2641    ---------+---------+---------+---------+---------+---------+ 2700 gccgcttaccggatacctgtccgcctttctcccttcgggaagcgtggcgctttctcaatg
2701    ---------+---------+---------+---------+---------+---------+ 2760 ctcacgctgtaggtatctcagttcggtgtaggtcgttcgctccaagctgggctgtgtgca
2761    ---------+---------+---------+---------+---------+---------+ 2820 cgaaccccccgttcagcccgaccgctgcgccttatccggtaactatcgtcttgagtccaa
2821    ---------+---------+---------+---------+---------+---------+ 2880 cccggtaagacacgacttatcgccactggaagcagccactggtaacaggattagcagagc
2881    ---------+---------+---------+---------+---------+---------+ 2940 gaggtatgtaggcggtgctacagagttcttgaagtggtggcctaactacggctacactag
2941    ---------+---------+---------+---------+---------+---------+ 3000 aaggacagtatttggtatctgcgctctgctgaagccagttaccttcggaaaaagagttgg
3001    ---------+---------+---------+---------+---------+---------+ 3060 tagctcttgatccggcaaacaaaccaccgctggtagcggtggttttttgtttgcaagca
3061    ---------+---------+---------+---------+---------+---------+ 3120 gcagattacgcgcagaaaaaaaggatctcaagaagatcctttgatcttttctacggggtc
3121    ---------+---------+---------+---------+---------+---------+ 3180 tgacgctcagtggaacgaaaactcacgttaagggattttggtcatgagattatcaaaaag
3181    ---------+---------+---------+---------+---------+---------+ 3240 gatcttcacctagatcctttttaaattaaaaatgaagttttaaatcaatctaaagtatata
3241    ---------+---------+---------+---------+---------+---------+ 3300 tgagtaaacttggtctgacagttaccaatgcttaatcagtgaggcacctatctcagcgat
3301    ---------+---------+---------+---------+---------+---------+ 3360 ctgtctatttcgttcatccatagttgcctgactccccgtcgtgtagataactacgatacg
3361    ---------+---------+---------+---------+---------+---------+ 3420 ggagggcttaccatctggccccagtgctgcaatgataccgcgagacccacgctcaccggc
3421    ---------+---------+---------+---------+---------+---------+ 3480 tccagatttatcagcaataaaccagccagccggaagggccgagcgcagaagtggtcctgc
3481    ---------+---------+---------+---------+---------+---------+ 3540 aactttatccgcctccatccagtctattaattgttgccgggaagctagagtaagtagttc
3541    ---------+---------+---------+---------+---------+---------+ 3600 gccagttaatagtttgcgcaacgttgttgccattgctacaggcatcgtgtggtcacgctc
3601    ---------+---------+---------+---------+---------+---------+ 3660 gtcgtttggtatggcttcattcagctccggttcccaacgatcaaggcgagttacatgatc
3661    ---------+---------+---------+---------+---------+---------+ 3720 ccccatgttgtgcaaaaaagcggttagctccttcggtcctccgatcgttgtcagaagtaa
3721    ---------+---------+---------+---------+---------+---------+ 3780 gttggccgcagtgttatcactcatggttatggcagcactgcataattctcttactgtcat
3781    ---------+---------+---------+---------+---------+---------+ 3840 gccatccgtaagatgcttttctgtgactggtgagtactcaaccaagtcattctgagaata
3841    ---------+---------+---------+---------+---------+---------+ 3900 gtgtatgcggcgaccgagttgctcttgcccgtcgtcaatacgggataataccgcgccaca
3901    ---------+---------+---------+---------+---------+---------+ 3960 tagcagaactttaaaagtgctcatcattggaaaacgttcttcggggcgaaaactctcaag
```

Fig. 26-c

```
3961 ---------+---------+---------+---------+---------+---------+ 4020
        gatcttaccgctgttgagatccagttcgatgtaacccactcgtgcacccaactgatcttc
4021 ---------+---------+---------+---------+---------+---------+ 4080
        agcatcttttactttcaccagcgtttctgggtgagcaaaaacaggaaggcaaaatgccgc
4081 ---------+---------+---------+---------+---------+---------+ 4140
        aaaaaagggaataagggcgacacggaaatgttgaatactcatactcttccttttcaata
4141 ---------+---------+---------+---------+---------+---------+ 4200
        ttattgaagcatttatcagggttattgtctcatgagcggatacatatttgaatgtattta
4201 ---------+---------+---------+---------+---------+---------+ 4260
        gaaaataaacaatagggggttccgcgcacatttccccgaaaagtgccacctgacgtcta
4261 ---------+---------+---------+---------+---------+---------+ 4320
        agaaaccattattatcatgacattaacctataaaaataggcgtatcacgaggcccttcg
4321 ---------+---------+---------+---------+---------+---------+ 4380
        tc
4381 -- 4382
```

Fig. 26-d pUHD10.3-hflt3 Ligand-exon 6 plasmid Length: 4224
1 CTCGAGTTTA CCACTCCCTA TCAGTGATAG AGAAAAGTGA AAGTCGAGTT
51 TACCACTCCC TATCAGTGAT AGAGAAAAGT GAAAGTCGAG TTTACCACTC
101 CCTATCAGTG ATAGAGAAAA GTGAAAGTCG AGTTTACCAC TCCCTATCAG
151 TGATAGAGAA AAGTGAAAGT CGAGTTTACC ACTCCCTATC AGTGATAGAG
201 AAAAGTGAAA GTCGAGTTTA CCACTCCCTA TCAGTGATAG AGAAAAGTGA
251 AAGTCGAGTT TACCACTCCC TATCAGTGAT AGAGAAAAGT GAAAGTCGAG
301 CTCGGTACCC GGGTCGAGTA GGCGTGTACG GTGGGAGGCC TATATAAGCA
351 GAGCTCGTTT AGTGAACCGT CAGATCGCCT GGAGACGCCA TCCACGCTGT
401 TTTGACCTCC ATAGAAGACA CCGGGACCGA TCCAGCCTCC GCGGCCCCGA
451 ATTCCggggc ccccggccga aATGacagtg ctggcgccag cctggagccc
501 aacaacctat ctcctcctgc tgctgctgct gagctcggga ctcagtggga
551 cccaggactg ctccttccaa cacagcccca tctcctccga cttcgctgtc
601 aaaatccgtg agctgtctga ctacctgctt caagattacc cagtcaccgt
651 ggcctccaac ctgcaggacg aggagctctg cggggggcctc tggcggctgg
701 tcctggcaca gcgctggatg gagcggctca agactgtcgc tgggtccaag
751 atgcaaggct tgctggagcg cgtgaacacg gagatacact ttgtcaccaa
801 atgtgccttt cagccccccc ccagctgtct tcgcttcgtc cagaccaaca
851 tctcccgcct cctgcaggag acctccgagc agctggtggc gctgaagccc
901 tggatcactc gccagaactt ctcccggtgc ctggagctgc agtgtcagcc
951 cgtagagacg gtgtttcacc gtgtcagcca ggatggtctc gatctcctga
1001 cctcgTGAtc tgcccgcctc ggcctcccaa agtgctagga ttacagatac
1051 tcctcaaccc tgccacccc atggagtccc cggcccctgg aggccacagc
1101 cccgacagcc ccgcagcccc ctctgctcct cctactgctg ctgcccgtgg
1151 gcctcctgct gctggccgct gcctggtgcc tgcactggca gaggacgcgg
1201 cggaggacac cccgccctgg ggagcaggtg cccccgtcc ccagtcccca
1251 ggacctgctg cttgtggagc actgacctgg ccaaggcctc atcctgcgga
1301 gccttaaaca acgcagtgag acagacatct atcatcccat tttacagggg
1351 aggatactga ggcacacaga ggggagtcac cagccagagg atgtatagcc
1401 tggacacaga ggaagttggc tagaggccgg tccttccttt gggccctct
1451 cattccctcc ccagaatgga ggcaacgcca gaatccagca ccggcccat
1501 ttacccaact ctgaacaaag cccCCGGAAT TCGAGCTCGG TACCCGGGGA

```
1551 TCCTCTAGAG GATCCAGACA TGATAAGATA CATTGATGAG TTTGGACAAA
1601 CCACAACTAG AATGCAGTGA AAAAAATGCT TTATTTGTGA AATTTGTGAT
1651 GCTATTGCTT TATTTGTAAC CATTATAAGC TGCAATAAAC AAGTTAACAA
1701 CAACAATTGC ATTCATTTTA TGTTTCAGGT TCAGGGGGAG GTGTGGGAGG
1751 TTTTTTAAAG CAAGTAAAAC CTCTACAAAT GTGGTATGGC TGATTATGAT
1801 CCTGCAAGCC TCGTCGTCTG GCCGGACCAC GCTATCTGTG CAAGGTCCCC
1851 GGACGCGCGC TCCATGAGCA GAGCGCCCGC CGCCGAGGCA AGACTCGGGC
1901 GGCGCCTGC CCGTCCCACC AGGTCAACAG GCGGTAACCG GCCTCTTCAT
1951 CGGGAATGCG CGCGACCTTC AGCATCGCCG GCATGTCCCC TGGCGGACGG
2001 GAAGTATCAG CTCGACCAAG CTTGGCGAGA TTTTCAGGAG CTAAGGAAGC
2051 TAAAATGGAG AAAAAAATCA CTGGATATAC CACCGTTGAT ATATCCCAAT
2101 GGCATCGTAA AGAACATTTT GAGGCATTTC AGTCAGTTGC TCAATGTACC
2151 TATAACCAGA CCGTTCAGCT GCATTAATGA ATCGGCCAAC GCGCGGGGAG
2201 AGGCGGTTTG CGTATTGGGC GCTCTTCCGC TTCCTCGCTC ACTGACTCGC
2251 TGCGCTCGGT CGTTCGGCTG CGGCGAGCGG TATCAGCTCA CTCAAAGGCG
2301 GTAATACGGT TATCCACAGA ATCAGGGGAT AACGCAGGAA AGAACATGTG
2351 AGCAAAAGGC CAGCAAAAGG CCAGGAACCG TAAAAAGGCC GCGTTGCTGG
2401 CGTTTTTCCA TAGGCTCCGC CCCCCTGACG AGCATCACAA AAATCGACGC
2451 TCAAGTCAGA GGTGGCGAAA CCCGACAGGA CTATAAAGAT ACCAGGCGTT
2501 TCCCCCTGGA AGCTCCCTCG TGCGCTCTCC TGTTCCGACC CTGCCGCTTA
2551 CCGGATACCT GTCCGCCTTT CTCCCTTCGG GAAGCGTGGC GCTTTCTCAA
2601 TGCTCACGCT GTAGGTATCT CAGTTCGGTG TAGGTCGTTC GCTCCAAGCT
2651 GGGCTGTGTG CACGAACCCC CCGTTCAGCC CGACCGCTGC GCCTTATCCG
2701 GTAACTATCG TCTTGAGTCC AACCCGGTAA GACACGACTT ATCGCCACTG
2751 GCAGCAGCCA CTGGTAACAG GATTAGCAGA GCGAGGTATG TAGGCGGTGC
2801 TACAGAGTTC TTGAAGTGGT GGCCTAACTA CGGCTACACT AGAAGGACAG
2851 TATTTGGTAT CTGCGCTCTG CTGAAGCCAG TTACCTTCGG AAAAAGAGTT
2901 GGTAGCTCTT GATCCGGCAA ACAAACCACC GCTGGTAGCG GTGGTTTTTT
2951 TGTTTGCAAG CAGCAGATTA CGCGCAGAAA AAAAGGATCT CAAGAAGATC
3001 CTTTGATCTT TTCTACGGGG TCTGACGCTC AGTGGAACGA AAACTCACGT
3051 TAAGGGATTT TGGTCATGAG ATTATCAAAA AGGATCTTCA CCTAGATCCT
3101 TTTAAATTAA AAATGAAGTT TTAAATCAAT CTAAAGTATA TATGAGTAAA
3151 CTTGGTCTGA CAGTTACCAA TGCTTAATCA GTGAGGCACC TATCTCAGCG
```

Fig. 26a-b

```
3201 ATCTGTCTAT TTCGTTCATC CATAGTTGCC TGACTCCCCG TCGTGTAGAT
3251 AACTACGATA CGGGAGGGCT TACCATCTGG CCCCAGTGCT GCAATGATAC
3301 CGCGAGACCC ACGCTCACCG GCTCCAGATT TATCAGCAAT AAACCAGCCA
3351 GCCGGAAGGG CCGAGCGCAG AAGTGGTCCT GCAACTTTAT CCGCCTCCAT
3401 CCAGTCTATT AATTGTTGCC GGGAAGCTAG AGTAAGTAGT TCGCCAGTTA
3451 ATAGTTTGCG CAACGTTGTT GCCATTGCTA CAGGCATCGT GGTGTCACGC
3501 TCGTCGTTTG GTATGGCTTC ATTCAGCTCC GGTTCCCAAC GATCAAGGCG
3551 AGTTACATGA TCCCCCATGT TGTGCAAAAA AGCGGTTAGC TCCTTCGGTC
3601 CTCCGATCGT TGTCAGAAGT AAGTTGGCCG CAGTGTTATC ACTCATGGTT
3651 ATGGCAGCAC TGCATAATTC TCTTACTGTC ATGCCATCCG TAAGATGCTT
3701 TTCTGTGACT GGTGAGTACT CAACCAAGTC ATTCTGAGAA TAGTGTATGC
3751 GGCGACCGAG TTGCTCTTGC CCGGCGTCAA TACGGGATAA TACCGCGCCA
3801 CATAGCAGAA CTTTAAAAGT GCTCATCATT GGAAAACGTT CTTCGGGGCG
3851 AAAACTCTCA AGGATCTTAC CGCTGTTGAG ATCCAGTTCG ATGTAACCCA
3901 CTCGTGCACC CAACTGATCT TCAGCATCTT TTACTTTCAC CAGCGTTTCT
3951 GGGTGAGCAA AAACAGGAAG GCAAAATGCC GCAAAAAAGG GAATAAGGGC
4001 GACACGGAAA TGTTGAATAC TCATACTCTT CCTTTTTCAA TATTATTGAA
4051 GCATTTATCA GGGTTATTGT CTCATGAGCG GATACATATT TGAATGTATT
4101 TAGAAAAATA AACAAATAGG GGTTCCGCGC ACATTTCCCC GAAAAGTGCC
4151 ACCTGACGTC TAAGAAACCA TTATTATCAT GACATTAACC TATAAAAATA
4201 GGCGTATCAC GAGGCCCTTT CGTC
```

Fig. 26a-c

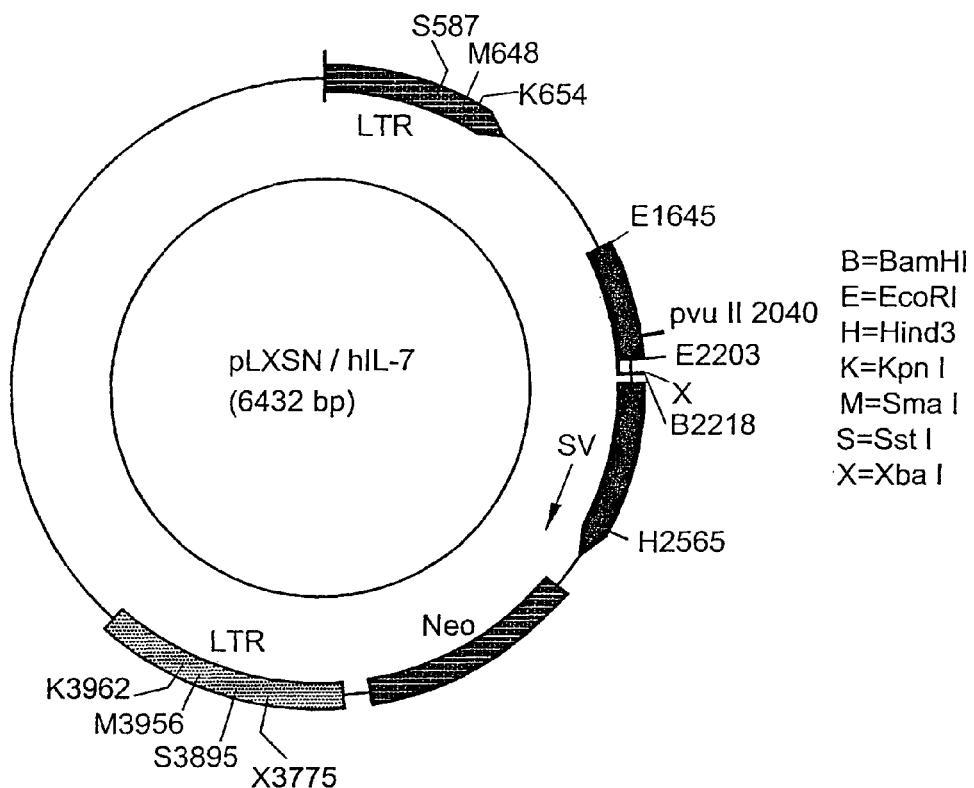
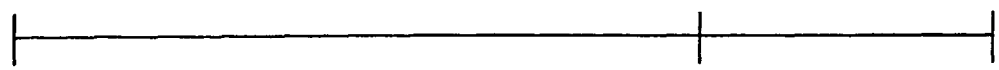
FIG.27

Plasmid-chart

Designation: pLXSN/hIL-2  
Insert: hIl-2 (473bp)  
Vector: pLXSN (5874bp)  
Recovery of insert: Eco RI /Bam HI  
    Hpal / Bam HI  
    Xho I / Bam HI Log no.:  
Location:  
Selection: Amp  
Ref.: pLXSN BioTechniques 7,980-987(1989)  
    hIL-2 Nature 302,305-309(1983)

Insert: Bgl II  
5' AGA TCT ACA - IL-2 - TAA TTA AGT BamHI 473 bp

SEQUENCE LISTING

```
<160> NUMBER OF SEQ ID NOS: 10

<210> SEQ ID NO 1
<211> LENGTH: 7969
<212> TYPE: DNA
<213> ORGANISM: Artificial Sequence
<220> FEATURE:
<223> OTHER INFORMATION: Vector for transforming supporting cell with a
      foreign to express a gene product of interest
<220> FEATURE:
<221> NAME/KEY: misc_feature
<222> LOCATION: (39)..(41)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
```

-continued

```
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (904)..(904)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (935)..(935)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (959)..(959)
<223> OTHER INFORMATION: n is a, c, g, or t
<220> FEATURE:
<221> NAME/KEY: misc_feature
<222> LOCATION: (967)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (994)..(994)
```

-continued

```
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1012)..(1012)
<223> OTHER INFORMATION: n is a, c, g, or t
<220> FEATURE:
<221> NAME/KEY: misc_feature
<222> LOCATION: (1026)..(1027)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1040)..(1041)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1070)..(1070)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1114)..(1115)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1120)..(1120)
<223> OTHER INFORMATION: n is a, c, g, or t
<220> FEATURE:
<221> NAME/KEY: misc_feature
<222> LOCATION: (1123)..(1123)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t
<220> FEATURE:
<221> NAME/KEY: misc_feature
```

```
<222> LOCATION: (1149)..(1149)
<223> OTHER INFORMATION: n is a, c, g, or t
<220> FEATURE:
<221> NAME/KEY: misc_feature
<222> LOCATION: (1153)..(1153)
<223> OTHER INFORMATION: n is a, c, g, or t
<220> FEATURE:
<221> NAME/KEY: misc_feature
<222> LOCATION: (1169)..(1174)
<223> OTHER INFORMATION: n is a, c, g, or t
<220> FEATURE:
<221> NAME/KEY: misc_feature
<222> LOCATION: (1664)..(1668)
<223> OTHER INFORMATION: n is a, c, g, or t

<400> SEQUENCE: 1
gctagcgatt taggtgacac tatagaatag atctcgacnn ngtcacccct agagtcgagc      60
tgtgacggtc cttacaatga aatgcanctg ggttatcttc ttcctgatgg caggggttac     120
aggtaagggg ctcccaagtc ccaaacttga gggtccataa actctgtgac agtggcaatc     180
actttgcctt tctttctaca ggggtgaatt cggctttcac agagcattca ccgctgaccc     240
ctcaccgtcg ggacctctgt agccgctcta tctggctagc aaggaagatt cgttcagacc     300
ttgactgctc ttacggaatc ctatgtaagt tgcctatttt gctgttatct gttttccctt     360
catcttttt gatccagcaa cttaccatca cgcatcagct ccattaccaa ttgtgaaagc     420
tctaatcata tagtcattca tataggttat ttgacatggg cccttccctt gaggaaaccc     480
atgtgacttt attttcttcc tctgggctgt ttaggagatg aagttacttg aatgagaaaa     540
tatatatgga gttctagaaa ggattggttt atatgtcttg gaggctattt caaaatttat     600
ttggccatat attctgaata ctacctagaa cagattagcc atgggccctn tgggttnttc     660
ataagccatt gttctgaant ttttagctt tgtaaatgaa aggtttatgg ataggaaga     720
gtnctatgaa cgtgggagga atttgtaaat cctaccaatt tntnctatat agcattagcc     780
cccacctttt antattctgc atcaaaagta agattgtgtc taaagagaaa ggtnagctat     840
caaaaggact cctataanat tcnttggaaa cttntggaan tgtcaaattt ntttgagcta     900
attnttggag ttccaaantt tgtcttntna cagtnaaggg ggancccat tcanatttnc     960
cccctnnng anaatgcttg ggggaaaaaa cctnccaacc ccnttgtggg angaagtttt    1020
tttaannttt taaggctngn ngaaacnggn ttttaatttt ttgggncnan cgcctntccc    1080
cggtaccagg aaaatcagga cctntttttg gggnngngcn ccnacngggg ggnaaaangg    1140
gaaatttcnt canaaaaaat cttttccgnn nnnngtgaag catcagggcc tgaacaagaa    1200
catcaacctg gactctgcgg atgggatgcc agtggcaagc actgatcagt ggagtgagct    1260
gaccgaggca gagcgactcc aagagaacct tcaagcttat cgtaccttcc atgttttgtt    1320
ggccaggctc ttagaagacc agcaggtgca ttttacccca accgaaggtg acttccatca    1380
agctatacat acccttcttc tccaagtcgc tgcctttgca taccagatag aggagttaat    1440
gatactcctg gaatacaaga tcccccgcaa tgaggctgat gggatgccta ttaatgttgg    1500
agatggtggt ctctttgaga agaagctgtg gggcctaaag gtgctgcagg agcttttcaca    1560
gtggacagta aggtccatcc atgaccttcg tttcatttct tctcatcaga ctgggatccc    1620
agcacgtggg agccattata ttgctaacaa caagaaaatg tagnnnnngc ggcctgcgcc    1680
gtctttcccg acgttaaagg gatgaaacca caagacttac cttcgctcgg aagtaaaacg    1740
acaaacacac acagttttgc ccgttttcat gagaaatggg acgtctgcgc acgaaacgcg    1800
ccgtcgcttg aggaggactt gtacaaacac gatctatgca ggtttcccca actgacacaa    1860
```

```
accgtgcaac ttgaaactcc gcctggtctt tccaggtcta gagggggtaac attttgtact    1920 gtgtttgact ccacgctcga tccactagcg agtgttagta gcggtactgc tgtctcgtag    1980
cggagcatgt tggccgtggg aacacctcct tggtaacaag gacccacggg gccgaaagcc    2040
atgtcctaac ggacccaaca tgtgtgcaac cccagcacgg cagctttact gtgaaaccca    2100
cttcaaggtg acattgatac tggtactcaa acactggtga caggctaagg atgcccttca    2160
ggtaccccga ggtaacaagc gacactcggg atctgagaag gggactggga cttcttaaa    2220 gtgcccagtt taaaaagctt ctacgcctga ataggtgacc ggaggccggc acctttcctt    2280
ttataaccac tgaacacatg gaagacgcca aaaacataaa gaaaggcccg cgccattct    2340 atcctctaga ggatggaacc gctggagagc aactgcataa ggctatgaag agatacgccc    2400
tggttcctgg aacaattgct tttacagatg cacatatcga ggtgaacatc acgtacgcgg    2460
aatacttcga aatgtccgtt cggttggcag aagctatgaa acgatatggg ctgaatacaa    2520
atcacagaat cgtcgtatgc agtgaaaact ctcttcaatt ctttatgccg gtgttgggcg    2580
cgttatttat cggagttgca gttgcgcccg cgaacgacat ttataatgaa cgtgaattgc    2640
tcaacagtat gaacatttcg cagcctaccg tagtgtttgt ttccaaaaag gggttgcaaa    2700
aaattttgaa cgtgcaaaaa aaattaccaa taatccagaa aattattatc atggattcta    2760
aaacggatta ccagggattt cagtcgatgt acacgttcgt cacatctcat ctacctcccg    2820
gttttaatga atacgatttt gtaccagagt cctttgatcg tgacaaaaca attgcactga    2880
taatgaattc ctctggatct actgggttac ctaagggtgt ggcccttccg catagaactg    2940
cctgcgtcag attctcgcat gccagagatc ctattttgg caatcaaatc attccggata    3000
ctgcgatttt aagtgttgtt ccattccatc acggttttgg aatgtttact acactcggat    3060
atttgatatg tggatttcga gtcgtcttaa tgtatagatt tgaagaagag ctgtttttac    3120
gatcccttca ggattacaaa attcaaagtg cgttgctagt accaacccta ttttcattct    3180
tcgccaaaag cactctgatt gacaaatacg atttatctaa tttacacgaa attgcttctg    3240
ggggcgcacc tctttcgaaa gaagtcgggg aagcggttgc aaaacgcttc catcttccag    3300
ggatacgaca aggatatggg ctcactgaga ctacatcagc tattctgatt acacccgagg    3360
gggatgataa accgggcgcg gtcggtaaag ttgttccatt ttttgaagcg aaggttgtgg    3420
atctggatac cgggaaaacg ctgggcgtta atcagagagg cgaattatgt gtcagaggac    3480
ctatgattat gtccggttat gtaaacaatc cggaagcgac caacgccttg attgacaagg    3540
atggatggct acattctgga gacatagctt actgggacga agacgaacac ttcttcatag    3600
ttgaccgctt gaagtcttta attaaataca aaggatatca ggtggccccc gctgaattgg    3660
aatcgatatt gttacaacac cccaacatct tcgacgcggg cgtggcaggt cttcccgacg    3720
atgacgccgg tgaacttccc gccgccgttg ttgttttgga gcacggaaag acgatgacgg    3780
aaaaagagat cgtggattac gtcgccagtc aagtaacaac cgcgaaaaag ttgcgcggag    3840
gagttgtgtt tgtggacgaa gtaccgaaag gtcttaccgg aaaactcgac gcaagaaaaa    3900
tcagagagat cctcataaag gccaagaagg gcggaaagtc caaattgtaa aatgtaactg    3960
tattcagcga tgacgaaatt cttagctatt gtaatgactc tagaggatct tgtgaagga    4020 accttacttc tgtggtgtga cataattgga caaactacct acagagattt aaagctctaa    4080
ggtaaatata aaattttaa gtgtataatg tgttaaacta ctgattctaa ttgtttgtgt    4140
attttagatt ccaaccctatg gaactgatga atggagcag tggtggaatg cctttaatga    4200
ggaaaacctg ttttgctcag aagaaatgcc atctagtgat gatgaggcta ctgctgactc    4260
```

```
tcaacattct actcctccaa aaagaagag aaggtagaa gaccccaagg actttccttc    4320
agaattgcta agttttttga gtcatgctgt gtttagtaat agaactcttg cttgctttgc    4380
tatttacacc acaaggaaa aagctgcact gctatacaag aaaattatgg aaaaatattc    4440
tgtaaccttt ataagtaggc ataacagtta taatcataac atactgtttt ttcttactcc    4500
acacaggcat agagtgtctg ctattaataa ctatgctcaa aaattgtgta cctttagctt    4560
tttaatttgt aaaggggtta ataaggaata tttgatgtat agtgccttga ctagagatca    4620
taatcagcca taccacatt gtagaggttt tacttgcttt aaaaaacctc ccacacctcc    4680
ccctgaacct gaaacataaa atgaatgcaa ttgttgttgt taacttgttt attgcagctt    4740
ataatggtta caaataaagc aatagcatca caaatttcac aaataaagca ttttttttcac    4800 tgcattctag ttgtggtttg tccaaactca tcaatgtatc ttatcatgtc tggatccccg    4860
ggtccctata gtgagtcgta ttagcttggc gtaatcatgg tcatagctgt ttcctgtgtg    4920
aaattgttat ccgctcacaa ttccacacaa catacgagcc ggaagcataa agtgtaaagc    4980
ctggggtgcc taatgagtga gctaactcac attaattgcg ttgcgctcac tgcccgcttt    5040
ccagtcggga aacctgtcgt gccagctgca ttaatgaatc ggccaacgcg cggggagagg    5100
cggtttgcgt attgggcgct cttccgcttc ctcgctcact gactcgctgc gctcggtcgt    5160
tcggctgcgg cgagcggtat cagctcactc aaaggcggta atacggttat ccacagaatc    5220
aggggataac gcaggaaaga acatgtgagc aaaaggccag caaaaggcca ggaaccgtaa    5280
aaaggccgcg ttgctggcgt ttttccatag gctccgcccc cctgacgagc atcacaaaaa    5340
tcgacgctca agtcagaggt ggcgaaaccc gacaggacta taaagatacc aggcgtttcc    5400
ccctggaagc tccctcgtgc gctctcctgt tccgaccctg ccgcttaccg gatacctgtc    5460
cgcctttctc ccttcgggaa gcgtggcgct ttctcaatgc tcacgctgta ggtatctcag    5520
ttcggtgtag gtcgttcgct ccaagctggg ctgtgtgcac gaaccccccg ttcagcccga    5580
ccgctgcgcc ttatccggta actatcgtct tgagtccaac ccggtaagac acgacttatc    5640
gccactggca gcagccactg gtaacaggat tagcagagcg aggtatgtag gcggtgctac    5700
agagttcttg aagtggtggc ctaactacgg ctacactaga aggacagtat ttggtatctg    5760
cgctctgctg aagccagtta ccttcggaaa aagagttggt agctcttgat ccggcaaaca    5820
aaccaccgct ggtagcggtg gtttttttgt ttgcaagcag cagattacgc gcagaaaaaa    5880
aggatctcaa gaagatcctt tgatcttttc tacggggtct gacgctcagt ggaacgaaaa    5940
ctcacgttaa gggattttgg tcatgagatt atcaaaaagg atcttcacct agatcctttt    6000
aaattaaaaa tgaagtttta atcaatcta agtatatat gagtaaactt ggtctgacag    6060
ttaccaatgc ttaatcagtg aggcacctat ctcagcgatc tgtctatttc gttcatccat    6120
agttgcctga ctccccgtcg tgtagataac tacgatacgg gagggcttac catctggccc    6180
cagtgctgca atgataccgc gagacccacg ctcaccggct ccagatttat cagcaataaa    6240
ccagccagcc ggaagggccg agcgcagaag tggtcctgca actttatccg cctccatcca    6300
gtctattaat tgttgccggg aagctagagt aagtagttcg ccagttaata gtttgcgcaa    6360
cgttgttgcc attgctacag gcatcgtggt gtcacgctcg tcgtttggta tggcttcatt    6420
cagctccggt tcccaacgat caaggcgagt tacatgatcc cccatgttgt gcaaaaaagc    6480
ggttagctcc ttcggtcctc cgatcgttgt cagaagtaag ttggccgcag tgttatcact    6540
catggttatg gcagcactgc ataattctct tactgtcatg ccatccgtaa gatgcttttc    6600
```

-continued

```
tgtgactggt gagtactcaa ccaagtcatt ctgagaatag tgtatgcggc gaccgagttg    6660
ctcttgcccg gcgtcaatac gggataatac cgcgccacat agcagaactt taaaagtgct    6720
catcattgga aaacgttctt cggggcgaaa actctcaagg atcttaccgc tgttgagatc    6780
cagttcgatg taacccactc gtgcacccaa ctgatcttca gcatctttta ctttcaccag    6840
cgttctgggt gagcaaaaa caggaaggca aaatgccgca aaaagggaa taagggcgac     6900 acggaaatgt tgaatactca tactcttcct ttttcaatat tattgaagca tttatcaggg    6960
ttattgtctc atgagcggat acatatttga atgtatttag aaaaataaac aaatagggt     7020 tccgcgcaca tttccccgaa aagtgccacc tgacgtctaa gaaaccatta ttatcatgac    7080
attaacctat aaaaataggc gtatcacgag gcccttcgt ctcgcgcgtt cggtgatga      7140 cggtgaaaac ctctgacaca tgcagctccc ggagacggtc acagcttgtc tgtaagcgga    7200
tgccgggagc agacaagccc gtcagggcgc gtcagcgggt gttggcgggt gtcggggctg    7260
gcttaactat gcggcatcag agcagattgt actgagagtg caccatatgc ggtgtgaaat    7320
accgcacaga tgcgtaagga gaaaataccg catcaggcgc cattcgccat tcaggctgcg    7380
caactgttgg aagggcgat cggtgcggcc ctcttcgcta ttacgccagc tggcgaaagg      7440
gggatgtgct gcaaggcgat taagttgggt aacgccaggg ttttcccagt cacgacgttg    7500
taaaacgacg gccagtgaat tcgacctgc agtcgacaga agccttacgt gacagctggc     7560
gaagaaccat ggccagctgg tgacaagcca aaacagctct ggctcgcaaa acatgttccc    7620
ttggctgctt tccacttccc cttgtgcttt gtttacttgt gtcagctggt tggctccta      7680 ggtatgagct catgcttggc tggcagccat ccagttttag ccagctctgc tttgtttact    7740
tgtgtcagct ggttggctcc ctaggtatga gctcatgctt ggctggcagc catccagttt    7800
tagccagctc ctccctacct tccctttttt ttatatatac aggaggccga ggccgcctcc    7860
gcctccaagc ttactcagaa gtagtaaggg cgtggaggct ttttaggagg ccagggaaat    7920
tcccttgttt ttcccttttt tgcagtaatt ttttgctgca aaaagctaa                7969
```

<210> SEQ ID NO 2
<211> LENGTH: 6971
<212> TYPE: DNA
<213> ORGANISM: Artificial Sequence
<220> FEATURE:
<223> OTHER INFORMATION: Vector for transforming supporting cell with a
      foreign to express a gene product of interest

<400> SEQUENCE: 2

```
gctagcgatt taggtgacac tatagaatag atccccatga agttatggga tgtcgtggct      60
gtctgcctgg tgctgctcca caccgcgtcc gccttcccgc tgcccgccgg taagaggcct     120
cccgaggcgc ccgccgaaga ccgctccctc ggccgccgcc gcgcgcctt cgcgctgagc      180 agtgactcaa atatgccaga ggattatcct gatcagttcg atgatgtcat ggattttatt    240
caagccacca ttaaaagact gaaaaggtca ccagataaac aaatggcagt gcttcctaga    300
agagagcgga tcggcaggc tgcagctgcc aacccagaga attccagagg aaaaggtcgg    360
agaggccaga ggggcaaaaa ccggggttgt gtcttaactg caatacattt aaatgtcact    420
gacttgggtc tgggctatga aaccaaggag gaactgattt ttaggtactg cagcggctct    480
tgcgatgcag ctgagacaac gtacgacaaa atattgaaaa acttatccag aaatagaagg    540
ctggtgagtg acaaagtagg gcaggcatgt tgcagaccca tcgcctttga tgatgacctg    600
tcgtttttag atgataacct ggtttaccat attctaagaa agcattccgc taaaaggtgt    660
```

```
ggatgtatct gactggtgcg ccgtctttcc cgacgttaaa gggatgaaac cacaagactt      720
accttcgctc ggaagtaaaa cgacaaacac acacagtttt gcccgttttc atgagaaatg      780
ggacgtctgc gcacgaaacg cgccgtcgct tgaggaggac ttgtacaaac acgatctatg      840
caggtttccc caactgacac aaaccgtgca acttgaaact ccgcctggtc tttccaggtc      900
tagaggggta acattttgta ctgtgtttga ctccacgctc gatccactag cgagtgttag      960
tagcggtact gctgtctcgt agcggagcat gttggccgtg gaacacctc cttggtaaca     1020
aggacccacg gggccgaaag ccatgtccta acggacccaa catgtgtgca accccagcac     1080
ggcagcttta ctgtgaaacc cacttcaagg tgacattgat actggtactc aaacactggt     1140
gacaggctaa ggatgccctt caggtacccc gaggtaacaa gcgacactcg ggatctgaga     1200
aggggactgg gacttcttta aagtgcccag tttaaaaagc ttctacgcct gaataggtga     1260
ccggaggccg gcacctttcc ttttataacc actgaacaca tggaagacgc caaaaacata     1320
aagaaaggcc cggcgccatt ctatcctcta gaggatggaa ccgctggaga gcaactgcat     1380
aaggctatga agagatacgc cctggttcct ggaacaattg cttttacaga tgcacatatc     1440
gaggtgaaca tcacgtacgc ggaatacttc gaaatgtccg ttcggttggc agaagctatg     1500
aaacgatatg ggctgaatac aaatcacaga atcgtcgtat gcagtgaaaa ctctcttcaa     1560
ttctttatgc cggtgttggg cgcgttattt atcggagttg cagttgcgcc cgcgaacgac     1620
atttataatg aacgtgaatt gctcaacagt atgaacattt cgcagcctac cgtagtgttt     1680
gtttccaaaa aggggttgca aaaaattttg aacgtgcaaa aaaaattacc aataatccag     1740
aaaattatta tcatggattc taaaacggat taccagggat ttcagtcgat gtacacgttc     1800
gtcacatctc atctacctcc cggttttaat gaatacgatt ttgtaccaga gtcctttgat     1860
cgtgacaaaa caattgcact gataatgaat tcctctggat ctactgggtt acctaagggt     1920
gtggcccttc cgcatagaac tgcctgcgtc agattctcgc atgccagaga tcctattttt     1980
ggcaatcaaa tcattccgga tactgcgatt ttaagtgttg ttccattcca tcacggtttt     2040
ggaatgttta ctacactcgg atatttgata tgtggatttc gagtcgtctt aatgtataga     2100
tttgaagaag agctgttttt acgatccctt caggattaca aaattcaaag tgcgttgcta     2160
gtaccaaccc tattttcatt cttcgccaaa agcactctga ttgacaaata cgatttatct     2220
aatttacacg aaattgcttc tgggggcgca cctctttcga agaagtcgg ggaagcggtt     2280
gcaaaacgct tccatcttcc agggatacga caaggatatg ggctcactga gactacatca     2340
gctattctga ttacacccga ggggatgat aaaccgggcg cggtcggtaa agttgttcca     2400
ttttttgaag cgaaggttgt ggatctggat accgggaaaa cgctgggcgt taatcagaga     2460
ggcgaattat gtgtcagagg acctatgatt atgtccggtt atgtaaacaa tccggaagcg     2520
accaacgcct tgattgacaa ggatggatgg ctacattctg gagacatagc ttactgggac     2580
gaagacgaac acttcttcat agttgaccgc ttgaagtctt taattaaata caaggatat     2640
caggtggccc ccgctgaatt ggaatcgata ttgttacaac accccaacat cttcgacgcg     2700
ggcgtggcag gtcttcccga cgatgacgcc ggtgaacttc ccgccgccgt tgttgttttg     2760
gagcacggaa agacgatgac ggaaaaagag atcgtggatt acgtcgccag tcaagtaaca     2820
accgcgaaaa agttgcgcgg aggagttgtg tttgtgacg aagtaccgaa aggtcttacc     2880
ggaaaactcg acgcaagaaa aatcagagag atcctcataa aggccaagaa gggcggaaag     2940
tccaaattgt aaaatgtaac tgtattcagc gatgacgaaa ttcttagcta ttgtaatgac     3000
tctagaggat ctttgtgaag gaaccttact tctgtggtgt gacataattg gacaaactac     3060
```

-continued

```
ctacagagat ttaaagctct aaggtaaata taaaatttttt aagtgtataa tgtgttaaac   3120
tactgattct aattgtttgt gtattttaga ttccaaccta tggaactgat gaatgggagc   3180
agtggtggaa tgcctttaat gaggaaaacc tgttttgctc agaagaaatg ccatctagtg   3240
atgatgaggc tactgctgac tctcaacatt ctactcctcc aaaaaagaag agaaaggtag   3300
aagaccccaa ggactttcct tcagaattgc taagttttttt gagtcatgct gtgtttagta   3360
atagaactct tgcttgcttt gctatttaca ccacaaagga aaaagctgca ctgctataca   3420
agaaaattat ggaaaaatat tctgtaacct ttataagtag gcataacagt tataatcata   3480
acatactgtt ttttcttact ccacacaggc atagagtgtc tgctattaat aactatgctc   3540
aaaaattgtg tacctttagc ttttttaattt gtaaagggggt taataaggaa tatttgatgt   3600
atagtgcctt gactagagat cataatcagc cataccacat ttgtagaggt tttacttgct   3660
ttaaaaaacc tcccacacct cccctgaac ctgaaacata aaatgaatgc aattgttgtt   3720
gttaacttgt ttattgcagc ttataatggt tacaaataaa gcaatagcat cacaaatttc   3780
acaaataaag catttttttc actgcattct agttgtggtt tgtccaaact catcaatgta   3840
tcttatcatg tctggatccc cgggtcccta tagtgagtcg tattagcttg gcgtaatcat   3900
ggtcatagct gtttcctgtg tgaaattgtt atccgctcac aattccacac aacatacgag   3960
ccggaagcat aaagtgtaaa gcctggggtg cctaatgagt gagctaactc acattaattg   4020
cgttgcgctc actgcccgct ttccagtcgg gaaacctgtc gtgccagctg cattaatgaa   4080
tcggccaacg cgcggggaga ggcggtttgc gtattgggcg ctcttccgct tcctcgctca   4140
ctgactcgct gcgctcggtc gttcggctgc ggcgagcggt atcagctcac tcaaaggcgg   4200
taatacggtt atccacagaa tcaggggata acgcaggaaa gaacatgtga gcaaaaggcc   4260
agcaaaaggc caggaaccgt aaaaaggccg cgttgctggc gtttttccat aggctccgcc   4320
cccctgacga gcatcacaaa aatcgacgct caagtcagag gtggcgaaac ccgacaggac   4380
tataaagata ccaggcgttt ccccctggaa gctccctcgt gcgctctcct gttccgaccc   4440
tgccgcttac cggatacctg tccgcctttc tcccttcggg aagcgtggcg ctttctcaat   4500
gctcacgctg taggtatctc agttcggtgt aggtcgttcg ctccaagctg ggctgtgtgc   4560
acgaaccccc cgttcagccc gaccgctgcg ccttatccgg taactatcgt cttgagtcca   4620
acccggtaag acacgactta tcgccactgg cagcagccac tggtaacagg attagcagag   4680
cgaggtatgt aggcggtgct acagagttct tgaagtggtg gcctaactac ggctacacta   4740
gaaggacagt atttggtatc tgcgctctgc tgaagccagt taccttcgga aaaagagttg   4800
gtagctcttg atccggcaaa caaaccaccg ctggtagcgg tggttttttt gtttgcaagc   4860
agcagattac gcgcagaaaa aaaggatctc aagaagatcc tttgatcttt tctacggggt   4920
ctgacgctca gtggaacgaa aactcacgtt aagggatttt ggtcatgaga ttatcaaaaa   4980
ggatcttcac ctagatcctt ttaaattaaa aatgaagttt taaatcaatc taaagtatat   5040
atgagtaaac ttggtctgac agttaccaat gcttaatcag tgaggcacct atctcagcga   5100
tctgtctatt tcgttcatcc atagttgcct gactccccgt cgtgtagata actacgatac   5160
gggagggctt accatctggc cccagtgctg caatgatacc gcgagaccca cgctcaccgg   5220
ctccagattt atcagcaata aaccagccag ccggaagggc cgagcgcaga agtggtcctg   5280
caactttatc cgcctccatc cagtctatta attgttgccg ggaagctaga gtaagtagtt   5340
cgccagttaa tagtttgcgc aacgttgttg ccattgctac aggcatcgtg gtgtcacgct   5400
```

```
cgtcgtttgg tatggcttca ttcagctccg gttcccaacg atcaaggcga gttacatgat    5460 ccccccatgtt gtgcaaaaaa gcggttagct ccttcggtcc tccgatcgtt gtcagaagta    5520
agttggccgc agtgttatca ctcatggtta tggcagcact gcataattct cttactgtca    5580
tgccatccgt aagatgcttt tctgtgactg gtgagtactc aaccaagtca ttctgagaat    5640
agtgtatgcg gcgaccgagt tgctcttgcc cggcgtcaat acgggataat accgcgccac    5700
atagcagaac tttaaaagtg ctcatcattg gaaaacgttc ttcggggcga aaactctcaa    5760
ggatcttacc gctgttgaga tccagttcga tgtaacccac tcgtgcaccc aactgatctt    5820
cagcatcttt tactttcacc agcgtttctg ggtgagcaaa aacaggaagg caaaatgccg    5880
caaaaaaggg aataagggcg acacggaaat gttgaatact catactcttc ctttttcaat    5940
attattgaag catttatcag ggttattgtc tcatgagcgg atacatattt gaatgtattt    6000
agaaaaataa acaaataggg gttccgcgca catttccccg aaaagtgcca cctgacgtct    6060
aagaaaccat tattatcatg acattaacct ataaaaatag gcgtatcacg aggccctttc    6120
gtctcgcgcg tttcggtgat gacggtgaaa acctctgaca catgcagctc ccggagacgg    6180
tcacagcttg tctgtaagcg gatgccggga gcagacaagc ccgtcagggc gcgtcagcgg    6240
gtgttggcgg gtgtcggggc tggcttaact atgcggcatc agagcagatt gtactgagag    6300
tgcaccatat gcggtgtgaa ataccgcaca gatgcgtaag gagaaaatac cgcatcaggc    6360
gccattcgcc attcaggctg cgcaactgtt gggaagggcg atcggtgcgg gcctcttcgc    6420
tattacgcca gctggcgaaa gggggatgtg ctgcaaggcg attaagttgg gtaacgccag    6480
ggttttccca gtcacgacgt tgtaaaacga cggccagtga atttcgacct gcagtcgaca    6540
gaagccttac gtgacagctg gcgaagaacc atggccagct ggtgacaagc caaaacagct    6600
ctggctcgca aaacatgttc ccttggctgc tttccacttc cccttgtgct tgtttacatt    6660
gtgtcagctg gttggctccc taggtatgag ctcatgcttg gctggcagcc atccagttt    6720 agccagctct gctttgttta cttgtgtcag ctggttggct ccctaggtat gagctcatgc    6780
ttggctggca gccatccagt tttagccagc tcctccctac cttcccttt ttttatatat    6840 acaggaggcc gaggccgcct ccgcctccaa gcttactcag aagtagtaag ggcgtggagg    6900
ctttttagga ggccagggaa attcccttgt ttttcccttt tttgcagtaa ttttttgctg    6960
caaaaagcta a                                                         6971
```

<210> SEQ ID NO 3
<211> LENGTH: 7558
<212> TYPE: DNA
<213> ORGANISM: Artificial Sequence
<220> FEATURE:
<223> OTHER INFORMATION: Vector for transforming supporting cell with a foreign to express a gene product of interest
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:

-continued

```
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (853)..(853)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (899)..(899)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (922)..(922)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (962)..(964)
<223> OTHER INFORMATION: n is a, c, g, or t
```

```
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1007)..(1007)
<223> OTHER INFORMATION: n is a, c, g, or t
<220> FEATURE:
<221> NAME/KEY: misc_feature
<222> LOCATION: (1021)..(1022)
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1035)..(1036)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1045)..(1045)
<223> OTHER INFORMATION: n is a, c, g, or t
<220> FEATURE:
<221> NAME/KEY: misc_feature
<222> LOCATION: (1061)..(1061)
<223> OTHER INFORMATION: n is a, c, g, or t
<220> FEATURE:
<221> NAME/KEY: misc_feature
<222> LOCATION: (1063)..(1063)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1099)..(1099)
<223> OTHER INFORMATION: n is a, c, g, or t
<220> FEATURE:
<221> NAME/KEY: misc_feature
<222> LOCATION: (1109)..(1110)
<223> OTHER INFORMATION: n is a, c, g, or t
<220> FEATURE:
<221> NAME/KEY: misc_feature
<222> LOCATION: (1112)..(1112)
<223> OTHER INFORMATION: n is a, c, g, or t
<220> FEATURE:
<221> NAME/KEY: misc_feature
<222> LOCATION: (1115)..(1115)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1121)..(1121)
<223> OTHER INFORMATION: n is a, c, g, or t
<220> FEATURE:
<221> NAME/KEY: misc_feature
<222> LOCATION: (1128)..(1128)
```

```
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t
<220> FEATURE:
<221> NAME/KEY: misc_feature
<222> LOCATION: (1144)..(1144)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1164)..(1169)
<223> OTHER INFORMATION: n is a, c, g, or t
<220> FEATURE:
<221> NAME/KEY: misc_feature
<222> LOCATION: (1659)..(1663)
<223> OTHER INFORMATION: n is a, c, g, or t

<400> SEQUENCE: 3
gctagcgatt taggtgacac tatagaatct cgacnngtca ccccctagagt cgagctgtga      60 cggtccttac aatgaaatgc anctgggtta tcttcttcct gatggcaggg gttacaggta     120
aggggctccc aagtcccaaa cttgagggtc cataaactct gtgacagtgg caatcacttt     180
gcctttcttt ctacaggggt gaattcggct ttcaccgagc attcaccgct gaccctcac      240 cgtcgggacc tctgtagccg ctctatctgg ctagcaagga agattcgttc agaccttgac     300
tgctcttacg gaatcctatg taagttgcct attttgctgt tatctgtttt cccttcatct     360 ttttttgatcc agcaacttac catcacgcat cagctccatt accaattgtg aaagctctaa     420
tcatatagtc attcatatag gttatttgac atgggccctt ccttgagga aacccatgtg      480 actttatttt cttcctctgg gctgtttagg agatgaagtt acttgaatga gaaaatatat     540
atggagttct agaaaggatt ggtttatatg tcttggaggc tatttcaaaa tttatttggc     600
catatattct gaatactacc tagaacagat tagccatggg ccctntgggt tnttcataag     660
ccattgttct gaantttttt agctttgtaa atgaaaggtt tatgggatag gaagagtnct     720
atgaacgtgg gaggaatttg taaatcctac caattntntnc tatatagcat tagcccccac     780
cttttantat tctgcatcaa aagtaagatt gtgtctaaag agaaaggtna gctatcaaaa     840
ggactcctat aanattcntt ggaaacttnt ggaantgtca aattntnttttg agctaatttnt    900 tggagttcca aanttttgtct tntnacagtn aaggggganc cccattcana tttnccccc      960 tnnnganaat gcttggggga aaaaacctnc caaccccntt gtgggangaa gttttttttaa    1020 nnttttaagg ctngnngaaa cnggnttttta attttttggg ncnancgcct ntccccggta    1080
ccaggaaaat caggacctnt ttttggggnn gngcnccnac nggggggnaa aangggaaat    1140
ttcntcanaa aaaatcttttt ccgnnnnnng tgaagcatca gggcctgaac aagaacatca    1200
acctggactc tgcggatggg atgccagtgg caagcactga tcagtggagt gagctgaccg    1260
aggcagagcg actccaagag aaccttcaag cttatcgtac cttccatgtt ttgttggcca    1320
ggctcttaga agaccagcag gtgcatttta ccccaaccga aggtgacttc catcaagcta    1380
tacataccct tcttctccaa gtcgctgcct ttgcatacca gatagaggag ttaatgatac    1440
tcctggaata caagatcccc cgcaatgagg ctgatgggat gcctattaat gttggagatg    1500
gtggtctctt tgagaagaag ctgtggggcc taaaggtgct gcaggagctt tcacagtgga    1560
cagtaaggtc catccatgac cttcgtttca tttcttctca tcagactggg atcccagcac    1620
gtgggagcca ttatattgct aacaacaaga aaatgtagnn nnngcggcct gcgccgtctt    1680
```

```
tcccgacgtt aaagggatga aaccacaaga cttaccttcg ctcggaagta aaacgacaaa    1740
cacacacagt tttgcccgtt ttcatgagaa atgggacgtc tgcgcacgaa acgcgccgtc    1800
gcttgaggag gacttgtaca aacacgatct atgcaggttt ccccaactga cacaaaccgt    1860
gcaacttgaa actccgcctg gtcttccag gtctagaggg gtaacatttt gtactgtgtt    1920
tgactccacg ctcgatccac tagcgagtgt tagtagcggt actgctgtct cgtagcggag    1980
catgttggcc gtgggaacac ctccttggta acaaggaccc acggggccga aagccatgtc    2040
ctaacggacc caacatgtgt gcaacccag cacggcagct ttactgtgaa acccacttca    2100
aggtgacatt gatactggta ctcaaacact ggtgacaggc taaggatgcc cttcaggtac    2160
cccgaggtaa caagcgacac tcgggatctg agaaggggac tgggacttct ttaaagtgcc    2220
cagtttaaaa agcttctacg cctgaatagg tgaccggagg ccggcacctt tccttttata    2280
accactgaac acatggaaga cgccaaaaac ataaagaaag gcccggcgcc attctatcct    2340
ctagaggatg gaaccgctgg agagcaactg cataaggcta tgaagagata cgccctggtt    2400
cctggaacaa ttgcttttac agatgcacat atcgaggtga acatcacgta cgcggaatac    2460
ttcgaaatgt ccgttcggtt ggcagaagct atgaaacgat atgggctgaa tacaaatcac    2520
agaatcgtcg tatgcagtga aaactctctt caattcttta tgccggtgtt gggcgcgtta    2580
tttatcggag ttgcagttgc gcccgcgaac gacatttata atgaacgtga attgctcaac    2640
agtatgaaca tttcgcagcc taccgtagtg tttgtttcca aaaggggtt gcaaaaaatt    2700
ttgaacgtgc aaaaaaaatt accaataatc cagaaaatta ttatcatgga ttctaaaacg    2760
gattaccagg gatttcagtc gatgtacacg ttcgtcacat ctcatctacc tcccggtttt    2820
aatgaatacg attttgtacc agagtccttt gatcgtgaca aaacaattgc actgataatg    2880
aattcctctg gatctactgg gttacctaag ggtgtggccc ttccgcatag aactgcctgc    2940
gtcagattct cgcatgccag agatcctatt tttggcaatc aaatcattcc ggatactgcg    3000
attttaagtg ttgttccatt ccatcacggt tttggaatgt ttactacact cggatatttg    3060
atatgtggat ttcgagtcgt cttaatgtat agatttgaag aagagctgtt tttacgatcc    3120
cttcaggatt acaaaattca aagtgcgttg ctagtaccaa ccctattttc attcttcgcc    3180
aaaagcactc tgattgacaa atacgattta tctaatttac acgaaattgc ttctggggc    3240
gcacctcttt cgaaagaagt cggggaagcg gttgcaaaac gcttccatct tccagggata    3300
cgacaaggat atgggctcac tgagactaca tcagctattc tgattacacc cgaggggat    3360
gataaaccgg gcgcggtcgg taaagttgtt ccatttttg aagcgaaggt tgtggatctg    3420
gataccggga aaacgctggg cgttaatcag agaggcgaat tatgtgtcag aggacctatg    3480
attatgtccg gttatgtaaa caatccggaa gcgaccaacg ccttgattga caaggatgga    3540
tggctacatt ctggagacat agcttactgg gacgaagacg aacacttctt catagttgac    3600
cgcttgaagt ctttaattaa atacaaagga tatcaggtgg ccccgctga attggaatcg    3660
atattgttac aacaccccaa catcttcgac gcgggcgtgg caggtcttcc cgacgatgac    3720
gccggtgaac ttcccgccgc cgttgttgtt ttggagcacg aaagacgat gacggaaaaa    3780
gagatcgtgg attacgtcgc cagtcaagta acaaccgcga aaaagttgcg cggaggagtt    3840
gtgtttgtgg acgaagtacc gaaaggtctt accggaaaac tcgacgcaag aaaaatcaga    3900
gagatcctca taaaggccaa gaagggcgga aagtccaaat tgtaaaatgt aactgtattc    3960
agcgatgacg aaattcttag ctattgtaat gactctagag gatctttgtg aaggaacctt    4020
```

```
acttctgtgg tgtgacataa ttggacaaac tacctacaga gatttaaagc tctaaggtaa    4080
atataaaatt tttaagtgta taatgtgtta aactactgat tctaattgtt tgtgtatttt    4140
agattccaac ctatggaact gatgaatggg agcagtggtg gaatgccttt aatgaggaaa    4200
acctgttttg ctcagaagaa atgccatcta gtgatgatga ggctactgct gactctcaac    4260
attctactcc tccaaaaaag aagagaaagg tagaagaccc caaggacttt ccttcagaat    4320
tgctaagttt tttgagtcat gctgtgttta gtaatagaac tcttgcttgc tttgctattt    4380
acaccacaaa ggaaaaagct gcactgctat acaagaaaat tatggaaaaa tattctgtaa    4440
cctttataag taggcataac agttataatc ataacatact gttttttctt actccacaca    4500
ggcatagagt gtctgctatt aataactatg ctcaaaaatt gtgtaccttt agcttttttaa   4560 tttgtaaagg ggttaataag gaatatttga tgtatagtgc cttgactaga gatcataatc    4620
agccatacca catttgtaga ggttttactt gcttttaaaaa acctcccaca cctcccctg    4680 aacctgaaac ataaaatgaa tgcaattgtt gttgttaact tgtttattgc agcttataat    4740
ggttacaaat aaagcaatag catcacaaat ttcacaaata aagcatttt ttcactgcat    4800 tctagttgtg gtttgtccaa actcatcaat gtatcttatc atgtctggat ccccgggtcc    4860
ctatagtgag tcgtattagc ttggcgtaat catggtcata gctgtttcct gtgtgaaatt    4920
gttatccgct cacaattcca cacaacatac gagccggaag cataaagtgt aaagcctggg    4980
gtgcctaatg agtgagctaa ctcacattaa ttgcgttgcg ctcactgccc gctttccagt    5040
cgggaaacct gtcgtgccag ctgcattaat gaatcggcca acgcgcgggg agaggcggtt    5100
tgcgtattgg gcgctcttcc gcttcctcgc tcactgactc gctgcgctcg tcgttcggc    5160 tgcggcgagc ggtatcagct cactcaaagg cggtaatacg gttatccaca gaatcagggg    5220
ataacgcagg aaagaacatg tgagcaaaag gccagcaaaa ggccaggaac cgtaaaaagg    5280
ccgcgttgct ggcgtttttc cataggctcc gcccccctga cgagcatcac aaaaatcgac    5340
gctcaagtca gaggtggcga aacccgacag gactataaag ataccaggcg tttccccctg    5400
gaagctccct cgtgcgctct cctgttccga cctgccgct taccggatac ctgtccgcct    5460
ttctcccttc gggaagcgtg gcgctttctc aatgctcacg ctgtaggtat ctcagttcgg    5520
tgtaggtcgt tcgctccaag ctgggctgtg tgcacgaacc ccccgttcag cccgaccgct    5580
gcgccttatc cggtaactat cgtcttgagt ccaacccggt aagacacgac ttatcgccac    5640
tggcagcagc cactggtaac aggattagca gagcgaggta tgtaggcggt gctacagagt    5700
tcttgaagtg gtgcctaac tacggctaca ctagaaggac agtatttggt atctgcgctc    5760
tgctgaagcc agttaccttc ggaaaaagag ttggtagctc ttgatccggc aaacaaacca    5820
ccgctggtag cggtggtttt tttgtttgca agcagcagat tacgcgcaga aaaaaggat    5880 ctcaagaaga tcctttgatc ttttctacgg ggtctgacgc tcagtggaac gaaaactcac    5940
gttaagggat tttggtcatg agattatcaa aaaggatctt cacctagatc cttttaaatt    6000
aaaaatgaag ttttaaatca atctaaagta tatatgagta aacttggtct gacagttacc    6060
aatgcttaat cagtgaggca cctatctcag cgatctgtct atttcgttca tccatagttg    6120
cctgactccc cgtcgtgtag ataactacga tacgggaggg cttaccatct ggccccagtg    6180
ctgcaatgat accgcgagac ccacgctcac cggctccaga tttatcagca ataaccagc    6240 cagccggaag ggccgagcgc agaagtggtc ctgcaacttt atccgcctcc atccagtcta    6300
ttaattgttg ccgggaagct agagtaagta gttcgccagt taatagtttg cgcaacgttg    6360
ttgccattgc tacaggcatc gtggtgtcac gctcgtcgtt tggtatggct tcattcagct    6420
```

```
ccggttccca acgatcaagg cgagttacat gatcccccat gttgtgcaaa aaagcggtta    6480
gctccttcgg tcctccgatc gttgtcagaa gtaagttggc cgcagtgtta tcactcatgg    6540
ttatggcagc actgcataat tctcttactg tcatgccatc cgtaagatgc ttttctgtga    6600
ctggtgagta ctcaaccaag tcattctgag aatagtgtat gcggcgaccg agttgctctt    6660
gcccggcgtc aatacgggat aataccgcgc cacatagcag aactttaaaa gtgctcatca    6720
ttggaaaacg ttcttcgggg cgaaaactct caaggatctt accgctgttg agatccagtt    6780
cgatgtaacc cactcgtgca cccaactgat cttcagcatc ttttactttc accagcgttt    6840
ctgggtgagc aaaaacagga aggcaaaatg ccgcaaaaaa gggaataagg gcgacacgga    6900
aatgttgaat actcatactc ttcctttttc aatattattg aagcatttat cagggttatt    6960
gtctcatgag cggatacata tttgaatgta tttagaaaaa taaacaaata ggggttccgc    7020
gcacatttcc ccgaaaagtg ccacctgacg tctaagaaac cattattatc atgacattaa    7080
cctataaaaa taggcgtatc acgaggccct ttcgtctcgc gcgtttcggt gatgacggtg    7140
aaaacctctg acacatgcag ctcccggaga cggtcacagc ttgtctgtaa gcggatgccg    7200
ggagcagaca agcccgtcag ggcgcgtcag cgggtgttgg cgggtgtcgg ggctggctta    7260
actatgcggc atcagagcag attgtactga gagtgcacca tatgcggtgt gaaataccgc    7320
acagatgcgt aaggagaaaa taccgcatca ggcgccattc gccattcagg ctgcgcaact    7380
gttgggaagg gcgatcggtg cgggcctctt cgctattacg ccagctggcg aaagggggat    7440
gtgctgcaag gcgattaagt tgggtaacgc caggttttc ccagtcacga cgttgtaaaa    7500
cgacggccag tgaatttcga cctgcagtcg acttttttta tatatacagg aggccgag     7558

<210> SEQ ID NO 4
<211> LENGTH: 6565
<212> TYPE: DNA
<213> ORGANISM: Artificial Sequence
<220> FEATURE:
<223> OTHER INFORMATION: Vector for transforming supporting cell with a
      foreign to express a gene product of interest

<400> SEQUENCE: 4
gctagcgatt taggtgacac tatagaatag atccccatga agttatggga tgtcgtggct      60
gtctgcctgg tgctgctcca caccgcgtcc gccttcccgc tgcccgccgg taagaggcct     120
cccgaggcgc ccgccgaaga ccgctccctc ggccgccgcc gcgcgcccc cgcgctgagc     180 agtgactcaa atatgccaga ggattatcct gatcagttcg atgatgtcat ggatttatt     240 caagccacca ttaaaagact gaaaaggtca ccagataaac aaatggcagt gcttcctaga     300
agagagcgga atcggcaggc tgcagctgcc aacccagaga attccagagg aaaaggtcgg     360
agaggccaga ggggcaaaaa ccgggggttgt gtcttaactg caatacattt aaatgtcact     420
gacttgggtc tgggctatga aaccaaggag gaactgattt taggtactg cagcggctct     480 tgcgatgcag ctgagacaac gtacgacaaa atattgaaaa acttatccag aaatagaagg     540
ctggtgagtc acaaagtagg gcaggcatgt tgcagaccca tcgcctttga tgatgacctg     600 tcgttttag atgataacct ggtttaccat attctaagaa agcattccgc taaaaggtgt     660
ggatgtatct gactggtgcg ccgtcttccc gacgttaaa gggatgaaac acaagactt     720 accttcgctc ggaagtaaaa cgacaaacac acacagtttt gcccgttttc atgagaaatg     780
ggacgtctgc gcacgaaacg cgccgtcgct tgaggaggac ttgtacaaac acgatctatg     840
caggtttccc caactgacac aaaccgtgca acttgaaact ccgcctggtc tttccaggtc     900
```

| | |
|---|---|
| tagagggta acattttgta ctgtgtttga ctccacgctc gatccactag cgagtgttag | 960 |
| tagcggtact gctgtctcgt agcggagcat gttggccgtg ggaacacctc cttggtaaca | 1020 |
| aggacccacg gggccgaaag ccatgtccta acggacccaa catgtgtgca accccagcac | 1080 |
| ggcagcttta ctgtgaaacc cacttcaagg tgacattgat actggtactc aaacactggt | 1140 |
| gacaggctaa ggatgcccct caggtacccc gaggtaacaa gcgacactcg ggatctgaga | 1200 |
| aggggactgg gacttcttta aagtgcccag tttaaaaagc ttctacgcct gaataggtga | 1260 |
| ccggaggccg gcacctttcc ttttataacc actgaacaca tggaagacgc caaaaacata | 1320 |
| aagaaaggcc cggcgccatt ctatcctcta gaggatggaa ccgctggaga gcaactgcat | 1380 |
| aaggctatga agagatacgc cctggttcct ggaacaattg cttttacaga tgcacatatc | 1440 |
| gaggtgaaca tcacgtacgc ggaatacttc gaaatgtccg ttcggttggc agaagctatg | 1500 |
| aaacgatatg gctgaatac aaatcacaga atcgtcgtat gcagtgaaaa ctctcttcaa | 1560 |
| ttctttatgc cggtgttggg cgcgttattt atcggagttg cagttgcgcc cgcgaacgac | 1620 |
| atttataatg aacgtgaatt gctcaacagt atgaacattt cgcagcctac cgtagtgttt | 1680 |
| gtttccaaaa agggggttgca aaaaattttg aacgtgcaaa aaaaattacc aataatccag | 1740 |
| aaaattatta tcatggattc taaaacggat taccagggat ttcagtcgat gtacacgttc | 1800 |
| gtcacatctc atctacctcc cggttttaat gaatacgatt ttgtaccaga gtcctttgat | 1860 |
| cgtgacaaaa caattgcact gataatgaat tcctctggat ctactgggtt acctaagggt | 1920 |
| gtggccctc cgcatagaac tgcctgcgtc agattctcgc atgccagaga tcctattttt | 1980 |
| ggcaatcaaa tcattccgga tactgcgatt ttaagtgttg ttccattcca tcacggtttt | 2040 |
| ggaatgttta ctacactcgg atatttgata tgtggatttc gagtcgtctt aatgtataga | 2100 |
| tttgaagaag agctgttttt acgatcccct caggattaca aaattcaaag tgcgttgcta | 2160 |
| gtaccaaccc tattttcatt cttcgccaaa agcactctga ttgacaaata cgatttatct | 2220 |
| aatttacacg aaattgcttc tggggggcgca cctctttcga agaagtcgg ggaagcggtt | 2280 |
| gcaaaacgct tccatcttcc agggatacga caaggatatg ggctcactga gactacatca | 2340 |
| gctattctga ttacacccga gggggatgat aaaccgggcg cggtcggtaa agttgttcca | 2400 |
| ttttttgaag cgaaggttgt ggatctggat accgggaaaa cgctgggcgt taatcagaga | 2460 |
| ggcgaattat gtgtcagagg acctatgatt atgtccggtt atgtaaacaa tccggaagcg | 2520 |
| accaacgcct tgattgacaa ggatggatgg ctacattctg gagacatagc ttactgggac | 2580 |
| gaagacgaac acttcttcat agttgaccgc ttgaagtctt taattaaata caaaggatat | 2640 |
| caggtggccc ccgctgaatt ggaatcgata ttgttacaac accccaacat cttcgacgcg | 2700 |
| ggcgtggcag gtcttcccga cgatgacgcc ggtgaacttc ccgccgccgt tgttgttttg | 2760 |
| gagcacggaa agacgatgac ggaaaaagag atcgtggatt acgtcgccag tcaagtaaca | 2820 |
| accgcgaaaa agttgcgcgg aggagttgtg tttgtggacg aagtaccgaa aggtcttacc | 2880 |
| ggaaaactcg acgcaagaaa aatcagagag atcctcataa aggccaagaa gggcggaaag | 2940 |
| tccaaattgt aaaatgtaac tgtattcagc gatgacgaaa ttcttagcta ttgtaatgac | 3000 |
| tctagaggat ctttgtgaag gaaccttact tctgtggtgt gacataattg gacaaactac | 3060 |
| ctacagagat ttaaagctct aaggtaaata taaaattttt aagtgtataa tgtgttaaac | 3120 |
| tactgattct aattgtttgt gtattttaga ttccaaccta tggaactgat gaatgggagc | 3180 |
| agtggtggaa tgcctttaat gaggaaaacc tgttttgctc agaagaaatg ccatctagtg | 3240 |

```
atgatgaggc tactgctgac tctcaacatt ctactcctcc aaaaaagaag agaaaggtag   3300
aagaccccaa ggactttcct tcagaattgc taagttttt gagtcatgct gtgtttagta   3360
atagaactct tgcttgcttt gctatttaca ccacaaagga aaaagctgca ctgctataca   3420
agaaaattat ggaaaatat tctgtaacct ttataagtag gcataacagt tataatcata   3480
acatactgtt ttttcttact ccacacaggc atagagtgtc tgctattaat aactatgctc   3540
aaaaattgtg tacctttagc ttttaattt gtaaaggggt taataaggaa tatttgatgt   3600
atagtgcctt gactagagat cataatcagc ataccacat tgtagaggt tttacttgct     3660 ttaaaaaacc tcccacacct cccctgaac ctgaaacata aaatgaatgc aattgttgtt    3720
gttaacttgt ttattgcagc ttataatggt tacaaataaa gcaatagcat cacaaatttc   3780
acaaataaag cattttttc actgcattct agttgtggtt tgtccaaact catcaatgta   3840
tcttatcatg tctggatccc cgggtcccta tagtgagtcg tattagcttg gcgtaatcat   3900
ggtcatagct gtttcctgtg tgaaattgtt atccgctcac aattccacac aacatacgag   3960
ccggaagcat aaagtgtaaa gcctggggtg cctaatgagt gagctaactc acattaattg   4020
cgttgcgctc actgcccgct ttccagtcgg gaaacctgtc gtgccagctg cattaatgaa   4080
tcggccaacg cgcggggaga ggcggtttgc gtattgggcg ctcttccgct tcctcgctca   4140
ctgactcgct gcgctcggtc gttcggctgc ggcgagcgg atcagctcac tcaaaggcgg    4200
taatacggtt atccacagaa tcaggggata acgcaggaaa gaacatgtga gcaaaaggcc   4260
agcaaaaggc caggaaccgt aaaaaggccg cgttgctggc gtttttccat aggctccgcc   4320
cccctgacga gcatcacaaa aatcgacgct caagtcagag gtggcgaaac ccgacaggac   4380
tataaagata ccaggcgttt ccccctggaa gctccctcgt gcgctctcct gttccgaccc   4440
tgccgcttac cggatacctg tccgcctttc tcccttcggg aagcgtggcg ctttctcaat   4500
gctcacgctg taggtatctc agttcggtgt aggtcgttcg ctccaagctg ggctgtgtgc   4560
acgaaccccc cgttcagccc gaccgctgcg ccttatccgg taactatcgt cttgagtcca   4620
acccggtaag acacgactta tcgccactgg cagcagccac tggtaacagg attagcagag   4680
cgaggtatgt aggcggtgct acagagttct tgaagtggtg cctaactac ggctacacta    4740 gaaggacagt atttggtatc tgcgctctgc tgaagccagt taccttcgga aaaagagttg   4800
gtagctcttg atccggcaaa caaccaccg ctggtagcgg tggttttttt gtttgcaagc    4860
agcagattac gcgcagaaaa aaggatctc aagaagatcc tttgatcttt tctacggggt    4920
ctgacgctca gtggaacgaa aactcacgtt aagggatttt ggtcatgaga ttatcaaaaa   4980
ggatcttcac ctagatcctt ttaaattaaa aatgaagttt taaatcaatc taagtatat    5040 atgagtaaac ttggtctgac agttaccaat gcttaatcag tgaggcacct atctcagcga   5100
tctgtctatt tcgttcatcc atagttgcct gactccccgt cgtgtagata actacgatac   5160
gggagggctt accatctggc cccagtgctg caatgatacc gcgagaccca cgctcaccgg   5220
ctccagattt atcagcaata aaccagccag ccggaagggc cgagcgcaga agtggtcctg   5280
caactttatc cgcctccatc cagtctatta attgttgccg ggaagctaga gtaagtagtt   5340
cgccagttaa tagtttgcgc aacgttgttg ccattgctac aggcatcgtg gtgtcacgct   5400
cgtcgtttgg tatggcttca ttcagctccg gttcccaacg atcaaggcga ttacatgat    5460 ccccatgtt gtgcaaaaaa gcggttagct ccttcggtcc tccgatcgtt gtcagaagta    5520
agttggccgc agtgttatca ctcatggtta tggcagcact gcataattct cttactgtca   5580
tgccatccgt aagatgcttt tctgtgactg gtgagtactc aaccaagtca ttctgagaat   5640
```

```
agtgtatgcg gcgaccgagt tgctcttgcc cggcgtcaat acgggataat accgcgccac    5700
atagcagaac tttaaaagtg ctcatcattg gaaaacgttc ttcggggcga aaactctcaa    5760
ggatcttacc gctgttgaga tccagttcga tgtaacccac tcgtgcaccc aactgatctt    5820
cagcatcttt tactttcacc agcgtttctg ggtgagcaaa aacaggaagg caaaatgccg    5880
caaaaaaggg aataagggcg acacggaaat gttgaatact catactcttc cttttcaat    5940 attattgaag catttatcag ggttattgtc tcatgagcgg atacatattt gaatgtattt    6000
agaaaaataa acaatagggg gttccgcgca catttccccg aaaagtgcca cctgacgtct    6060
aagaaaccat tattatcatg acattaacct ataaaaatag gcgtatcacg aggcccttc    6120 gtctcgcgcg tttcggtgat gacggtgaaa acctctgaca catgcagctc ccggagacgg    6180
tcacagcttg tctgtaagcg gatgccggga gcagacaagc ccgtcagggc gcgtcagcgg    6240
gtgttggcgg gtgtcggggc tggcttaact atgcggcatc agagcagatt gtactgagag    6300
tgcaccatat gcggtgtgaa ataccgcaca gatgcgtaag gagaaaatac cgcatcaggc    6360
gccattcgcc attcaggctg cgcaactgtt gggaagggcg atcggtgcgg gcctcttcgc    6420
tattacgcca gctggcgaaa ggggggatgtg ctgcaaggcg attaagttgg gtaacgccag    6480
ggttttccca gtcacgacgt tgtaaaacga cggccagtga atttcgacct gcagtcgact    6540 tttttatat atacaggagg ccgag                                           6565

<210> SEQ ID NO 5
<211> LENGTH: 7840
<212> TYPE: DNA
<213> ORGANISM: Artificial Sequence
<220> FEATURE:
<223> OTHER INFORMATION: Vector for transforming supporting cell with a
      foreign to express a gene product of interest

<400> SEQUENCE: 5
tcgagtttac cactccctat cagtgataga gaaaagtgaa agtcgagttt accactccct      60
atcagtgata gagaaaagtg aaagtcgagt ttaccactcc ctatcagtga tagagaaagt     120
gaaagtcgag tttaccactc cctatcagtg atagagaaaa gtgaaagtcg agtttaccac     180
tccctatcag tgatagagaa aagtgaaagt cgagtttacc actccctatc agtgatagag     240
aaaagtgaag tcgagtttac cactccctat cagtgataga gaaaagtgaa agtcgagctc     300
ggtacccggg tcgagtaggc gtgtacggtg ggaggcctat ataagcagag ctcgtttagt     360
gaaccgtcag atcgcctgga gacgccatcc acgctgtttt gacctccata gaagacaccg     420
ggaccgatcc agcctgcggc cgcagatcta attcaccggt tagtataaaa gcagacattt     480
tatgcaccaa aagagaactg caatgtttca ggacccacag gagcgaccca gaaagttacc     540
acagttatgc acagagctgc aaacaactat acatgatata atattagaat gtgtgtactg     600
caagcaacag ttactgcgac gtgaggtata tgactttgct tttcgggatt tatgcatagt     660
atatagagat gggaatccat atgctgtatg tgataaatgt ttaaagtttt attctaaaat     720
tagtgagtat agacattatt gttatagttt gtatggaaca acattagaac agcaatacaa     780
caaaccgttg tgtgatttgt taattaggtg tattaactgt caaaagccac tgtgtcctga     840
agaaaagcaa agacatctgg acaaaaagca aagattccat aatataaggg gtcggtggac     900
cggtcgatgt atgtcttgtt gcagatcatc aagaacacgt agagaaaccc agctgtaatc     960
atgcatggag atacacctac attgcatgaa tatatgttag atttgcaacc agagacaact    1020
gatctctact gttatgagca attaaatgac agctcagagg aggaggatga aatagatggt    1080
```

```
ccagctggac aagcagaacc ggacagagcc cattacaata ttgtaacctt ttgttgcaag   1140
tgtgactcta cgcttcggtt gtgcgtacaa agcacacacg tagacattcg tactttggaa   1200
gacctgttaa tgggcacact aggaattgtg tgccccatct gttctcagaa accataatct   1260
accatggctg atcctgcagg atcccccggg aacaacaaca attgcattca ttttatgttt   1320
caggttcagg gggaggtgtg ggaggttttt taaagcaagt aaaacctcta caaatgtggt   1380
atggctgatt atgatcctgc aagcctcgtc gtctggccgg accacgctat ctgtgcaagg   1440
tccccgacg cgcgctccat gagcagagcg tcgcgccccc tacccaccgt actcgtcaat   1500
tccaagggca tcggtaaaca gagcgccgta gggggcggag tcgtgggggg taaatcccgg   1560
acccggggaa tccccgtccc ccaacatgtc cagatcgaaa tcgtctagcg cgtcggcatg   1620
cgccatcgcc acgtcctcgc cgtataagtg gagctcgtcc cccaggctga catcggtcgg   1680
gggggccgtc gacagtctgc gcgtgtgtcc gcggggagaa aggacaggcg cggagccgcc   1740
agccccgcct cttcggggc gtcgtcgtcc gggagatcga gcaggccctc gatggtagac   1800
ccgtaattgt ttttcgtacg cgcgcggctg tacgcggacc cactttcaca tttaagttgt   1860
ttttctaatc cgcatatgat caattcaagg ccgaataaga aggctggctc tgcaccttgg   1920
tgatcaaata attcgatagc ttgtcgtaat aatggcggca tactatcagt agtaggtgtt   1980
tcccttctt ctttagcgac ttgatgctct tgatcttcca atacgcaacc taagtaaaa   2040
tgccccacag cgctgagtgc atataatgca ttctctagtg aaaaaccttg ttggcataaa   2100
aaggctaatt gattttcgag agtttcatac tgtttttctg taggccgtgt acctaaatgt   2160
acttttgctc catcgcgatg acttagtaaa gcacatctaa aactttttagc gttattacgt   2220
aaaaaatctt gccagctttc cccttctaaa gggcaaaagt gagtatggtg cctatctaac   2280
atctcaatgg ctaaggcgtc gagcaaagcc cgcttatttt ttacatgcca atacaatgta   2340
ggctgctcta cacctagctt ctgggcgagt ttacgggttg ttaaaccttc gattccgacc   2400
tcattaagca gctctaatgc gctgttaatc actttacttt tatctaatct agacatggtg   2460
gaagcttttt gcaaaagcct aggcctccaa aaaagcctcc tcactacttc tggaatagct   2520
cagaggccga ggcggcctcg gcctctgcat aaataaaaaa aattagtcag ccatggggcg   2580
gagaatgggc ggaactgggc ggagttaggg gcgggatggg cggagttagg ggcgggacta   2640
tggttgctga ctaattgaga tgcatgcttt gcatacttct gcctgctggg gagcctgggg   2700
actttccaca cctggttgct gactaattga gatgcatgct ttgcatactt ctgcctgctg   2760
gggagcctgg ggactttcca caccctaact gacacacatt ccacaggtcg actagatcga   2820
attctcaatt gttttacgcg gcccgatgca tgggtcgtg cgctcctttc ggtcgggcgc   2880
tgcgggtcgt ggggcgggcg tcaggcaccg ggcttgcggg tcatgcacca ggtcgcgcgg   2940
tccttcgggc actcgacgtc ggcggtgacg gtgaagccga ccgctcgta aaggggagg    3000
ttgcggggcg cggaggtctc caggaaggcg ggcaccccgg cgcgctcggc cgcctccact   3060
ccggggagca cgacggcgct gcccagaccc ttgccctggt ggtcgggcga gacgccgacg   3120
gtggccagga accacgcggg ctccttgggc cggtgcggcg ccaggaggcc ttccatctgt   3180
tgctgcgcgg ccagccggga accgctcaac tcggccatgc gcgggccgat ctcgcgaac    3240
accgccccg cttcgacgct ctccggcgtg gtccagaccg ccaccgcggc gccgtcgtcc   3300
gcgacccaca ccttgccgat gtcgagcccg acgcgcgtga ggaagagttc ttgcagctcg   3360
gtgacccgct cgatgtggcg gtccggatcg acggtgtggc gcgtggcggg gtagtcggcg   3420
```

```
aacgcggcgg cgagggtgcg tacggccctg gggacgtcgt cgcgggtggc gaggcgcacc    3480
gtgggcttgt actcggtcat ggtaagctga tccggccggc gcctagagaa ggagtgaggg    3540
ctggataaag ggaggattga ggcggggtcg aaagaggagg ttcaaggggg agagacggcg    3600
cggatggaag aagaggaggc ggaggcttag ggtgtacaaa gggcttgacc cagggagggg    3660
ggtcaaaagc caaggcttcc caggtcacga tgtaggggac ctggtctggg tgtccatgcg    3720
ggccaggtga aaagaccttg atcttaacct gggtgatgag gtctcggtta aaggtgccgt    3780
ctcgcggcca tccgacgtta aaggttggcc attctgcaga gcagaaggta acccaacgtc    3840
tcttcttgac atctaccgac tggttgtgag cgagccgctc gacatctttc cagtgatcta    3900
aggtcaaact aagggagtg gtaacagtct ggccctaatt ttcagacaaa tacagaaaca    3960
cagtcagaca gagacaacac agaacgatgc tgcagcagaa aagacgcgcg gcttcggttc    4020
caaaccgaaa gcaaaaattc agacggaggc gggaactgtt ttaggttctc gtctcctacc    4080
agaaccacat atcctgacgg ggtcggattc cacatcgact cccttcctca ggtcgggcca    4140
caaaaacggc ccccaaagtc cctgggacgt ctcccagggt tgcggccggg tgttcagaac    4200
tcgtcagttc caccacgggt ccgccagata cagagctagt tagctaacta gtaccgacgc    4260
aggcgcataa aatcagtcat agacactaga caatcggaca gacacagata agttgctggc    4320
cagcttacct cccggtggtg ggtcggtggt ccctgggcag gggtctcccg atcccggacg    4380
agcccccaaa tgaaagaccc ccgctgacgg gtagtcaatc actcagagga gaccctccca    4440
aggaacagcg agaccacaag tcggatgcaa ctgcaagagg gtttattgga tacacgggta    4500
cccgggcgac tcagtcaatc ggaggactgg cgccccgagt gaggggttgt gggctctttt    4560
attgagctcg gggagcagaa gcgcgcgaac agaagcgaga agcgaactga ttggttagtt    4620
caaataaggc acagggtcat ttcaggtcct tggggcaccc tggaaacatc tgatggttct    4680
ctagaaactg ctgagggctg gaccgcatct ggggaccatc tgttcttggc cctgagccgg    4740
ggcaggaact gcttaccaca gatatcctgt ttggcccata ttcagctgtt ccatctgttc    4800 ttggcccctga gccggggcag gaactgctta ccacagatat cctgtttggc ccatattcag    4860
gctgcaggtg gcacttttcg gggaaatgtg cgcggaaccc ctatttgttt attttctaa    4920 atacattcaa atatgtatcc gctcatgaga caataaccct gataaatgct tcaataatat    4980 tgaaaagga agagtatgag tattcaacat ttccgtgtcg cccttattcc cttttttgcg    5040 gcatttttgcc ttcctgtttt tgctcaccca gaaacgctgg tgaaagtaaa agatgctgaa    5100
gatcagttgg gtgcacgagt gggttacatc gaactggatc tcaacagcgg taagatcctt    5160
gagagttttc gccccgaaga acgttttcca atgatgagca cttttaaagt tctgctatgt    5220
ggcgcggtat tatcccgtgt tgacgccggg caagagcaac tcggtcgccg catacactat    5280
tctcagaatg acttggttga gtactcacca gtcacagaaa agcatcttac ggatggcatg    5340
acagtaagag aattatgcag tgctgccata accatgagtg ataacactgc ggccaactta    5400
cttctgacaa cgatcggagg accgaaggag ctaaccgctt ttttgcacaa catgggggat    5460
catgtaactc gccttgatcg ttgggaaccg gagctgaatg aagccatacc aaacgacgag    5520
cgtgacacca cgatgcctgt agcaatggca acaacgttgc gcaaactatt aactggcgaa    5580
ctacttactc tagcttcccg gcaacaatta atagactgga tggaggcgga taaagttgca    5640
ggaccacttc tgcgctcggc ccttccggct ggctggttta ttgctgataa atctggagcc    5700
ggtgagcgtg ggtctcgcgg tatcattgca gcactgggc cagatggtaa gccctcccgt    5760
atcgtagtta tctacacgac ggggagtcag gcaactatgg atgaacgaaa tagacagatc    5820
```

```
gctgagatag gtgcctcact gattaagcat tggtaactgt cagaccaagt ttactcatat    5880
atactttaga ttgatttgcg gccggccgca aacttcattt ttaatttaaa aggatctagg    5940
tgaagatcct ttttgataat ctcatgacca aaatcccctta acgtgagttt tcgttccact    6000
gagcgtcaga cccgtagaa aagatcaaag gatcttcttg agatcctttt tttctgcgcg    6060
taatctgctg cttgcaaaca aaaaaaccac cgctaccagc ggtggtttgt ttgccggatc    6120
aagagctacc aactcttttt ccgaaggtaa ctggcttcag cagagcgcag ataccaaata    6180
ctgtccttct agtgtagccg tagttaggcc accacttcaa gaactctgta gcaccgccta    6240
catacctcgc tctgctaatc ctgttaccag tggctgctgc cagtggcgat aagtcgtgtc    6300
ttaccgggtt ggactcaaga cgatagttac cggataaggc gcagcggtcg ggctgaacgg    6360
ggggttcgtg cacacagccc agcttggagc gaacgaccta caccgaactg agatacctac    6420
agcgtgagct atgagaaagc gccacgcttc ccgaagggag aaaggcggac aggtatccgg    6480
taagcggcag ggtcggaaca ggagagcgca cgagggagct tccaggggga aacgcctggt    6540
atctttatag tcctgtcggg tttcgccacc tctgacttga gcgtcgattt ttgtgatgct    6600
cgtcaggggg gcggagccta tggaaaaacg ccagcaacgc ggccttttta cggttcctgg    6660
ccttttgctg gccttttgct cacatgttct ttcctgcgtt atcccctgat tctgtggata    6720
accgtattac cgcctttgag tgagctgata ccgctcgccg cagccgaacg accgagcgca    6780
gcgagtcagt gagcgaggaa gcggaagagc gcccaatacgc aaaccgcctc tccccgcgcg    6840
ttggccgatt cattaatgca actatggcca tttaatgtaa atacttaaga aaaaaaacca    6900
aattaatttt gatacatgct gcatgtgaag accccgctg acgggtagtc aatcactcag    6960
aggagaccct cccaaggcag cgagaccaca agtcggaaat gaaagacccc cgctgacggg    7020
tagtcaatca ctcagaggag accctcccaa ggaacagcga gaccacaagt cggatgcaac    7080
tgcaagaggg tttattggat acacgggtac ccgggcgact cagtcaatcg gaggactggc    7140
gccccgagtg aggggttgtg ggctctttta ttgagctcgg ggagcagaag cgcgcgaaca    7200
gaagcgagaa gcgaactgat tggttagttc aaataaggca cagggtcatt tcaggtcctt    7260
ggggcaccct ggaaacatct gatggttctc tagaaactgc tgagggctgg accgcatctg    7320
gggaccatct gttcttggcc ctgagccggg gcaggaactg cttaccacag atatcctgtt    7380
tggcccatat tcagctgttc catctgttct tggccctgag ccggggcagg aactgcttac    7440
cacagatatc ctgtttggcc catattcagc tgttccatct gttcctgacc ttgatctgaa    7500
cttctctatt ctcagttatg tattttccca tgccttgcaa aatggcgtta cttaagctag    7560
cagatctgct agcttgccaa acctacaggt ggggtctttc attcccccct ttttctggag    7620
actaaataaa atctttttatt ttatgcgcac atttccccga aaagtgccac ctgacgtcta    7680
agaaaccatt attatcatga cattaaccta taaaaatagg cgtatcacga ggccctttcg    7740 tcctgcacatt tccccgaaaa gtgccacctg acgtctaaga accattatt atcatgacat    7800 taacctataa aataggcgt atcacgaggc cctttcgtcc                            7840
```

<210> SEQ ID NO 6
<211> LENGTH: 8852
<212> TYPE: DNA
<213> ORGANISM: Plasmid pUHD10.3-hflt3-Ligand-exon 6
<220> FEATURE:
<221> NAME/KEY: misc_feature
<222> LOCATION: (466)..(476)
<223> OTHER INFORMATION: n is a, c, g, or t
<220> FEATURE:

```
<221> NAME/KEY: misc_feature
<222> LOCATION: (2280)..(2290)
<223> OTHER INFORMATION: n is a, c, g, or t

<400> SEQUENCE: 6
tcgagtttac cactccctat cagtgataga gaaaagtgaa agtcgagttt accactccct      60
atcagtgata gagaaaagtg aaagtcgagt ttaccactcc ctatcagtga tagagaaagt     120
gaaagtcgag tttaccactc cctatcagtg atagagaaaa gtgaaagtcg agtttaccac     180
tccctatcag tgatagagaa aagtgaaagt cgagtttacc actccctatc agtgatagag     240
aaaagtgaag tcgagtttac cactccctat cagtgataga gaaagtgaa agtcgagctc      300 ggtacccggg tcgagtaggc gtgtacggtg ggaggcctat ataagcagag ctcgtttagt     360
gaaccgtcag atcgcctgga gacgccatcc acgctgtttt gacctccata agagacaccg     420
ggaccgatcc agcctgcggc cgcttaatta gtttaaacg gatccnnnnn nnnnnnatgc      480
catctagtga tgatgaggct actgctgact ctcaacattc tactcctcca aaaagaaga     540 gaaaggtaga agaccccaag gactttcctt cagaattgct aagttttttg agtcatgctg     600
tgtttagtaa tagaactctt gcttgctttg ctatttacac cacaaaggaa aaagctgcac     660
tgctatacaa gaaaattatg gaaaaatatt ctgtaacctt tataagtagg cataacagtt     720
ataatcataa catactgttt tttcttactc cacacaggca tagagtgtct gctattaata     780
actatgctca aaaattgtgt acctttagct ttttaatttg taagggggtt aataaggaat     840
atttgatgta tagtgccttg actagagatc catttttctgt tattgaggaa agtttgccag    900
gtgggttaaa ggagcatgat tttaatccag aagaagcaga ggaaactaaa caagtgtcct     960
ggaagcttgt aacagagtat gcaatggaaa caaaatgtga tgatgtgttg ttattgcttg    1020
ggatgtactt ggaatttcag tacagttttg aaatgtgttt aaaatgtatt aaaaaagaac    1080
agcccagcca ctataagtac catgaaaagc attatgcaaa tgctgctata tttgctgaca    1140
gcaaaaacca aaaaaccata tgccaacagg ctgttgatac tgttttagct aaaaagcggg    1200
ttgatagcct acaattaact agagaacaaa tgttaacaaa cagatttaat gatcttttgg    1260
ataggatgga tataatgttt ggttctacag gctctgctga catagaagaa tggatggctg    1320
gagttgcttg gctacactgt tgttgccca aatggattc agtggtgtat gacttttaa       1380 aatgcatggt gtacaacatt cctaaaaaaa gatactggct gtttaaagga ccaattgata    1440
gtggtaaaac tacattagca gctgctttgc ttgaattatg tgggggggaaa gctttaaatg    1500 ttaatttgcc cttggacagg ctgaactttg agctaggagt agctattgac cagtttttag    1560
tagtttttga ggatgtaaag ggcactggag gggagtccag agatttgcct tcaggtcagg    1620
gaattaataa cctggacaat ttaagggatt atttggatgg cagtgttaag gtaaacttag    1680
aaaagaaaca cctaaataaa gaactcaaa tatttccccc tggaatagtc accatgaatg     1740
agtacagtgt gcctaaaaca ctgcaggcca gatttgtaaa acaaatagat ttaggccca     1800 aagattattt aaagcattgc ctggaacgca gtgagttttt gttagaaaag agaataattc    1860
aaagtggcat tgctttgctt cttatgttaa tttggtacag acctgtggct gagtttgctc    1920
aaagtattca gagcagaatt gtggagtgga agagagatt ggacaaagag tttagtttgt     1980
cagtgtatca aaaaatgaag tttaatgtgg ctatgggaat tggagtttta gattggctaa    2040
gaaacagtga tgatgatgat gaagacagcc aggaaaatgc tgataaaaat gaagatggtg    2100
gggagaagaa catggaagac tcagggcatg aaacaggcat tgattcacag tcccaaggct    2160
catttcaggc ccctcagtcc tcacagtctg ttcatgatca taatcagcca taccacattt    2220
```

```
gtagaggttt tacttgcttt aaaaaacctc ccacacctcc ccctgaacct gaaacataan   2280
nnnnnnnnnn ggatcccccg ggaacaacaa caattgcatt cattttatgt ttcaggttca   2340
gggggaggtg tgggaggttt tttaaagcaa gtaaaacctc tacaaatgtg gtatggctga   2400
ttatgatcct gcaagcctcg tcgtctggcc ggaccacgct atctgtgcaa ggtccccgga   2460
cgcgcgctcc atgagcagag cgtcgcgccc cctacccacc gtactcgtca attccaaggg   2520
catcggtaaa cagagcgccg taggggggcgg agtcgtgggg ggtaaatccc ggacccgggg   2580
aatccccgtc ccccaacatg tccagatcga aatcgtctag cgcgtcggca tgcgccatcg   2640
ccacgtcctc gccgtataag tggagctcgt cccccaggct gacatcggtc ggggggggccg   2700 tcgacagtct gcgcgtgtgt ccgcggggag aaaggacagg cgcggagccg ccagcccgc    2760 ctcttcgggg gcgtcgtcgt ccgggagatc gagcaggccc tcgatggtag acccgtaatt   2820
gtttttcgta cgcgcgcggc tgtacgcgga cccactttca catttaagtt gtttttctaa   2880
tccgcatatg atcaattcaa ggccgaataa gaaggctggc tctgcacctt ggtgatcaaa   2940
taattcgata gcttgtcgta ataatggcgg catactatca gtagtaggtg tttcccttc    3000 ttctttagcg acttgatgct cttgatcttc caatacgcaa cctaaagtaa aatgccccac   3060
agcgctgagt gcatataatg cattctctag tgaaaaacct tgttggcata aaaaggctaa   3120
ttgattttcg agagtttcat actgttttc tgtaggccgt gtacctaaat gtacttttgc   3180
tccatcgcga tgacttagta aagcacatct aaaactttta gcgttattac gtaaaaaatc   3240
ttgccagctt tccccttcta aagggcaaaa gtgagtatgg tgcctatcta acatctcaat   3300
ggctaaggcg tcgagcaaag cccgcttatt ttttacatgc caatacaatg taggctgctc   3360
tacacctagc ttctgggcga gtttacgggt tgttaaacct tcgattccga cctcattaag   3420
cagctctaat gcgctgttaa tcactttact tttatctaat ctagacatgg tggaagcttt   3480
ttgcaaaagc ctaggcctcc aaaaaagcct cctcactact tctggaatag ctcagaggcc   3540
gaggcggcct cggcctctgc ataaataaaa aaaattagtc agccatgggg cggagaatgg   3600
gcggaactgg gcggagttag gggcgggatg ggcggagtta ggggcgggac tatggttgct   3660
gactaattga gatgcatgct ttgcatactt ctgcctgctg gggagcctgg ggactttcca   3720
cacctggttg ctgactaatt gagatgcatg ctttgcatac ttctgcctgc tggggagcct   3780
ggggactttc cacaccctaa ctgacacaca ttccacaggt cgactagatc gaattctcaa   3840
ttgttttacg cggcccgatg catgggggtcg tgcgctcctt tcggtcgggc gctgcgggtc   3900
gtggggcggg cgtcaggcac cgggcttgcg ggtcatgcac caggtcgcgc ggtccttcgg   3960
gcactcgacg tcgcggtga cggtgaagcc gagccgctcg tagaagggga ggttgcgggg   4020
cgcggaggtc tccaggaagg cgggcacccc ggcgcgctcg gccgcctcca ctccggggag   4080
cacgacggcg ctgcccagac ccttgccctg gtggtcgggc gagacgccga cggtggccag   4140
gaaccacgcg ggctccttgg gccggtgcgg cgccaggagg ccttccatct gttgctgcgc   4200
ggccagccgg gaaccgctca actcggccat gcgcgggccg atctcggcga acaccgcccc   4260
cgcttcgacg ctctccggcg tggtccagac cgccaccgcg gcgccgtcgt ccgcgaccca   4320
caccttgccg atgtcgagcc cgacgcgcgt gaggaagagt tcttgcagct cggtgacccg   4380
ctcgatgtgg cggtccggat cgacggtgtg gcgcgtggcc gggtagtcgg cgaacgcggc   4440
ggcgagggtg cgtacggccc tgggggacgtc gtcgcgggtg gcgaggcgca ccgtgggctt   4500
gtactcggtc atggtaagct gatccggccg gcgcctagag aaggagtgag ggctggataa   4560
```

```
agggaggatt gaggcggggt cgaaagagga ggttcaaggg ggagagacgg cgcggatgga   4620
agaagaggag gcggaggctt agggtgtaca aagggcttga cccagggagg ggggtcaaaa   4680
gccaaggctt cccaggtcac gatgtagggg acctggtctg ggtgtccatg cgggccaggt   4740
gaaaagacct tgatcttaac ctgggtgatg aggtctcggt taaaggtgcc gtctcgcggc   4800
catccgacgt taaaggttgg ccattctgca gagcagaagg taacccaacg tctcttcttg   4860
acatctaccg actggttgtg agcgagccgc tcgacatctt ccagtgatc taaggtcaaa   4920
cttaagggag tggtaacagt ctggccctaa ttttcagaca aatacagaaa cacagtcaga   4980
cagagacaac acagaacgat gctgcagcag acaagacgcg cggcttcggt tccaaaccga   5040
aagcaaaaat tcagacggag gcgggaactg ttttaggttc tcgtctccta ccagaaccac   5100
atatcctgac ggggtcggat tccacatcga ctcccttcct caggtcgggc cacaaaaacg   5160
gcccccaaag tccctgggac gtctcccagg gttgcggccg ggtgttcaga actcgtcagt   5220
tccaccacgg gtccgccaga tacagagcta gttagctaac tagtaccgac gcaggcgcat   5280
aaaatcagtc atagacacta gacaatcgga cagacacaga taagttgctg gccagcttac   5340
ctcccggtgg tgggtcggtg gtccctgggc aggggtctcc cgatcccgga cgagcccca   5400
aatgaaagac ccccgctgac gggtagtcaa tcactcagag gagaccctcc caaggaacag   5460
cgagaccaca agtcggatgc aactgcaaga gggtttattg gatacacggg tacccgggcg   5520
actcagtcaa tcggaggact ggcgccccga gtgagggggtt gtgggctctt ttattgagct   5580
cggggagcag aagcgcgcga acagaagcga gaagcgaact gattggttag ttcaaataag   5640
gcacagggtc atttcaggtc cttggggcac cctggaaaca tctgatggtt ctctagaaac   5700
tgctgagggc tggaccgcat ctggggacca tctgttcttg gccctgagcc ggggcaggaa   5760
ctgcttacca cagatatcct gtttggccca tattcagctg ttccatctgt tcttggccct   5820
gagccggggc aggaactgct taccacagat atcctgtttg gcccatattc aggctgcagg   5880
tggcactttt cggggaaatg tgcgcggaac ccctatttgt ttatttttct aaatacattc   5940
aaatatgtat ccgctcatga gacaataacc ctgataaatg cttcaataat attgaaaaag   6000
gaagagtatg agtattcaac atttccgtgt cgcccttatt cccttttttg cggcattttg   6060
ccttcctgtt tttgctcacc cagaaacgct ggtgaaagta aaagatgctg aagatcagtt   6120
gggtgcacga gtgggttaca tcgaactgga tctcaacagc ggtaagatcc ttgagagttt   6180
tcgccccgaa gaacgttttc caatgatgag cacttttaaa gttctgctat gtggcgcggt   6240
attatcccgt gttgacgccg ggcaagagca actcggtcgc cgcatacact attctcagaa   6300
tgacttggtt gagtactcac cagtcacaga aaagcatctt acggatggca tgacagtaag   6360
agaattatgc agtgctgcca taaccatgag tgataacact gcggccaact tacttctgac   6420
aacgatcgga ggaccgaagg agctaaccgc ttttttgcac aacatggggg atcatgtaac   6480
tcgccttgat cgttgggaac cggagctgaa tgaagccata ccaaacgacg agcgtgacac   6540
cacgatgcct gtagcaatgg caacaacgtt gcgcaaacta ttaactggcg aactacttac   6600
tctagcttcc cggcaacaat taatagactg gatggaggcg gataaagttg caggaccact   6660
tctgcgctcg gcccttccgg ctggctggtt tattgctgat aaatctggag ccggtgagcg   6720
tgggtctcgc ggtatcattg cagcactggg gccagatggt aagccctccc gtatcgtagt   6780
tatctacacg acggggagtc aggcaactat ggatgaacga atagacaga tcgctgagat   6840
aggtgcctca ctgattaagc attggtaact gtcagaccaa gtttactcat atatacttta   6900
gattgatttg cggccggccg caaacttcat ttttaattta aaaggatcta ggtgaagatc   6960
```

```
cttttttgata atctcatgac caaaatccct taacgtgagt tttcgttcca ctgagcgtca   7020
gaccccgtag aaaagatcaa aggatcttct tgagatcctt tttttctgcg cgtaatctgc   7080
tgcttgcaaa caaaaaaacc accgctacca gcggtggttt gtttgccgga tcaagagcta   7140
ccaactcttt ttccgaaggt aactggcttc agcagagcgc agataccaaa tactgtcctt   7200
ctagtgtagc cgtagttagg ccaccacttc aagaactctg tagcaccgcc tacatacctc   7260
gctctgctaa tcctgttacc agtggctgct gccagtggcg ataagtcgtg tcttaccggg   7320
ttggactcaa gacgatagtt accggataag gcgcagcggt cgggctgaac ggggggttcg   7380
tgcacacagc ccagcttgga gcgaacgacc tacaccgaac tgagatacct acagcgtgag   7440
ctatgagaaa gcgccacgct tcccgaaggg agaaaggcgg acaggtatcc ggtaagcggc   7500
agggtcggaa caggagagcg cacgagggag cttccagggg gaaacgcctg gtatctttat   7560
agtcctgtcg ggtttcgcca cctctgactt gagcgtcgat ttttgtgatg ctcgtcaggg   7620
gggcggagcc tatggaaaaa cgccagcaac gcggccttt tacggttcct ggccttttgc    7680
tggccttttg ctcacatgtt ctttcctgcg ttatccctg attctgtgga taaccgtatt     7740
accgcctttg agtgagctga taccgctcgc cgcagccgaa cgaccgagcg cagcgagtca   7800
gtgagcgagg aagcggaaga gcgcccaatac gcaaaccgcc tctccccgcg cgttggccga   7860
ttcattaatg caactatggc catttaatgt aaatacttaa gaaaaaaaac caaattaatt   7920
ttgatacatg ctgcatgtga agaccccgc tgacgggtag tcaatcactc agaggagacc    7980
ctcccaaggc agcgagacca caagtcggaa atgaaagacc cccgctgacg ggtagtcaat   8040
cactcagagg agaccctccc aaggaacagc gagaccacaa gtcggatgca actgcaagag   8100
ggtttattgg atacacgggt acccgggcga ctcagtcaat cggaggactg gcgccccgag   8160
tgaggggttg tgggctcttt tattgagctc ggggagcaga agcgcgcgaa cagaagcgag   8220
aagcgaactg attggttagt tcaaataagg cacagggtca tttcaggtcc ttggggcacc   8280
ctggaaacat ctgatggttc tctagaaact gctgagggct ggaccgcatc tgggaccat    8340 ctgttcttgg ccctgagccg gggcaggaac tgcttaccac agatatcctg tttgcccat    8400 attcagctgt tccatctgtt cttggccctg agccggggca ggaactgctt accacagata   8460
tcctgtttgg cccatattca gctgttccat ctgttcctga ccttgatctg aacttctcta   8520
ttctcagtta tgtattttc catgccttgc aaaatggcgt tacttaagct agcagatctg    8580
ctagcttgcc aaacctacag gtggggtctt tcattccccc cttttctgg agactaaata     8640 aaatctttta ttttatgcgc acatttcccc gaaaagtgcc acctgacgtc taagaaacca   8700
ttattatcat gacattaacc tataaaaata ggcgtatcac gaggccctt cgtccgcaca     8760 tttccccgaa aagtgccacc tgacgtctaa gaaaccatta ttatcatgac attaacctat    8820
aaaaataggc gtatcacgag gccctttcgt cc                                   8852
```

<210> SEQ ID NO 7  
<211> LENGTH: 3621  
<212> TYPE: DNA  
<213> ORGANISM: Artificial Sequence  
<220> FEATURE:  
<223> OTHER INFORMATION: Vector for transforming supporting cell with a foreign to express a gene product of interest

<400> SEQUENCE: 7

```
ctcgagttta ccactcccta tcagtgatag agaaaagtga agtcgagtt taccactccc      60 tatcagtgat agagaaaagt gaaagtcgag tttaccactc cctatcagtg atagagaaaa    120
```

```
gtgaaagtcg agtttaccac tccctatcag tgatagagaa aagtgaaagt cgagtttacc      180
actccctatc agtgatagag aaaagtgaaa gtcgagttta ccactcccta tcagtgatag      240
agaaaagtga agtcgagtt taccactccc tatcagtgat agagaaagt gaaagtcgag       300 ctcggtaccc gggtcgagta ggcgtgtacg gtgggaggcc tatataagca gagctcgttt      360
agtgaaccgt cagatcgcct ggagacgcca tccacgctgt tttgacctcc atagaagaca      420
ccgggaccga tccagcctcc gcggccccga attaaacagt cgagctacgt caacgaaaaa      480
taaaatccaa acatgagccg cctgcccgtc ctgctcctgc tccaactcct ggtccgcccc      540
ggactccaag ctcccatgac ccagacaacg tccttgaaga caagctgggt taactgctct      600
aacatgatcg atgaaattat aacacactta agcagccac ctttgccttt gctggacttc        660
aacaacctca atggggaaga ccaagacatt ctgatggaaa ataaccttcg aaggccaaac      720
ctggaggcat tcaacagggc tgtcaagagt ttacagaacg catcagcaat tgagagcatt      780
cttaaaaatc tcctgccatg tctgccctg gccacggccg cacccacgcg acatccaatc       840
catatcaagg acggtgactg gaatgaattc cggaggaaac tgacgttcta tctgaaaacc      900
cttgagaatg cgcaggctca acagacgact ttgagcctcg cgatctttta gaactcgact      960
ctagacatga taagatacat tgatgagttt ggacaaacca caactagaat gcagtgaaaa     1020
aaatgcttta tttgtgaaat ttgtgatgct attgctttat ttgtaaccat tataagctgc     1080
aataaacaag ttaacaacaa caattgcatt cattttatgt ttcaggttca ggggaggtg      1140 tgggaggttt tttaaagcaa gtaaaacctc tacaaatgtg gtatggctga ttatgatcct     1200
gcaagcctcg tcgtctggcc ggaccacgct atctgtgcaa ggtccccgga cgcgcgctcc     1260
atgagcagag cgcccgccgc cgaggcaaga ctcgggcggc gccctgcccg tcccaccagg     1320
tcaacaggcg gtaaccggcc tcttcatcgg gaatgcgcgc gaccttcagc atcgccggca     1380
tgtcccctgg cggacgggaa gtatcagctc gaccaagctt ggcgagattt tcaggagcta     1440
aggaagctaa aatggagaaa aaaatcactg gatataccac cgttgatata tcccaatggc     1500
atcgtaaaga acattttgag gcatttcagt cagttgctca atgtacctat aaccagaccg     1560
ttcagctgca ttaatgaatc ggccaacgcg cggggagagg cggtttgcgt attgggcgct     1620
cttccgcttc ctcgctcact gactcgctgc gctcggtcgt tcggctgcgg cgagcggtat     1680
cagctcactc aaagtcggta atacggttat ccacagaatc aggggataac gcaggaaaga     1740
acatgtgagc aaaaggccag caaaaggcca ggaaccgtaa aaaggccgcg ttgctggcgt     1800
ttttccatag gctccgcccc cctgacgagc atcacaaaaa tcgacgctca agtcagaggt     1860
ggcgaaaccc gacaggacta taaagatacc aggcgtttcc ccctggaagc tccctcgtgc     1920
gctctcctgt tccgaccctg ccgcttaccg gatacctgtc cgcctttctc ccttcgggaa     1980
gcgtggcgct ttctcaatgc tcacgctgta ggtatctcag ttcggtgtag tcgttcgct      2040 ccaagctggg ctgtgtgcac gaaccccccg ttcagcccga ccgctgcgcc ttatccggta     2100
actatcgtct tgagtccaac ccggtaagac acgacttatc gccactggaa gcagccactg     2160
gtaacaggat tagcagagcg aggtatgtag gcggtgctac agagttcttg aagtggtggc     2220
ctaactacgg ctacactaga aggacagtat ttggtatctg cgctctgctg aagccagtta     2280
ccttcggaaa aagagttggt agctcttgat ccggcaaaca aaccaccgct ggtagcggtg     2340
gtttttttgt ttgcaagcag cagattacgc gcagaaaaaa aggatctcaa gaagatcctt     2400
tgatcttttc tacggggtct gacgctcagt ggaacgaaaa ctcacgttaa gggattttgg     2460
```

```
tcatgagatt atcaaaaagg atcttcacct agatccttt  aaattaaaaa tgaagtttta    2520
aatcaatcta aagtatatat gagtaaactt ggtctgacag ttaccaatgc ttaatcagtg    2580
aggcacctat ctcagcgatc tgtctatttc gttcatccat agttgcctga ctccccgtcg    2640
tgtagataac tacgatacgg gagggcttac catctggccc cagtgctgca atgataccgc    2700
gagacccacg ctcaccggct ccagatttat cagcaataaa ccagccagcc ggaagggccg    2760
agcgcagaag tggtcctgca actttatccg cctccatcca gtctattaat tgttgccggg    2820
aagctagagt aagtagttcg ccagttaata gtttgcgcaa cgttgttgcc attgctacag    2880
gcatcgtgtg gtcacgctcg tcgtttggta tggcttcatt cagctccggt tcccaacgat    2940
caaggcgagt tacatgatcc cccatgttgt gcaaaaaagc ggttagctcc ttcggtcctc    3000
cgatcgttgt cagaagtaag ttggccgcag tgttatcact catggttatg gcagcactgc    3060
ataattctct tactgtcatg ccatccgtaa gatgcttttc tgtgactggt gagtactcaa    3120
ccaagtcatt ctgagaatag tgtatgcggc gaccgagttg ctcttgcccg tcgtcaatac    3180
gggataatac cgcgccacat agcagaactt taaaagtgct catcattgga aaacgttctt    3240
cggggcgaaa actctcaagg atcttaccgc tgttgagatc cagttcgatg taacccactc    3300
gtgcacccaa ctgatcttca gcatctttta ctttcaccag cgtttctggg tgagcaaaaa    3360
caggaaggca aaatgccgca aaaaagggaa taagggcgac acggaaatgt tgaatactca    3420
tactcttcct ttttcaatat tattgaagca tttatcaggg ttattgtctc atgagcggat    3480
acatatttga atgtatttag aaaaataaac aaataggggt tccgcgcaca tttccccgaa    3540
aagtgccacc tgacgtctaa gaaaccatta ttatcatgac attaacctat aaaaataggc    3600
gtatcacgag gcccttcgt c                                               3621

<210> SEQ ID NO 8
<211> LENGTH: 3752
<212> TYPE: DNA
<213> ORGANISM: Artificial Sequence
<220> FEATURE:
<223> OTHER INFORMATION: Vector for transforming supporting cell with a
      foreign to express a gene product of interest

<400> SEQUENCE: 8
ctcgagttta ccactcccta tcagtgatag agaaaagtga agtcgagtt taccactccc      60 tatcagtgat agagaaaagt gaaagtcgag tttaccactc cctatcagtg atagagaaaa    120
gtgaaagtcg agtttaccac tccctatcag tgatagagaa aagtgaaagt cgagtttacc    180
actccctatc agtgatagag aaaagtgaaa gtcgagttta ccactcccta tcagtgatag    240
agaaaagtga agtcgagtt taccactccc tatcagtgat agagaaaagt gaaagtcgag    300
ctcggtaccc gggtcgagta ggcgtgtacg gtgggaggcc tatataagca gagctcgttt    360
agtgaaccgt cagatcgcct ggagacgcca tccacgctgt tttgacctcc atagaagaca    420
ccgggaccga tccagcctcc gcggtggcgg ccgctctaga actagtggat cccccagctt    480
acctgccatg ccagtacccc caggagaaga ttccaaagat gtagccgccc cacacagaca    540
gccactcacc tcttcagaac gaattgacaa acaaattcgg tacatcctcg acggcatctc    600
agccctgaga aaggagacat gtaacaagag taacatgtgt gaaagcagca agaggcact    660 ggcagaaaac aacctgaacc ttccaaagat ggctgaaaaa gatggatgct ccaatctgg    720 attcaatgag gagacttgcc tggtgaaaat catcactggt cttttggagt ttgaggtata    780
cctagagtac ctccagaaca gatttgagag tagtgaggaa caagccagag ctgtccagat    840
```

```
gagtacaaaa gtcctgatcc agttcctgca gaaaaaggca aagaatctag atgcaataac    900
cacccctgac ccaaccacaa atgccagcct gctgacgaag ctgcaggcac agaaccagtg    960
gctgcaggac atgacaactc atctcattct gcgcagcttt aaggagttcc tgcagtccag   1020
cctgagggct cttcggcaaa tgtagtaagg atccgaattc gagctcggta cccggggatc   1080
ctctagagga tccagacatg ataagataca ttgatgagtt tggacaaacc acaactagaa   1140
tgcagtgaaa aaaatgcttt atttgtgaaa tttgtgatgc tattgcttta tttgtaacca   1200
ttataagctg caataaacaa gttaacaaca acaattgcat tcattttatg tttcaggttc   1260
aggggggaggt gtgggaggtt ttttaaagca agtaaaacct ctacaaatgt ggtatggctg   1320
attatgatcc tgcaagcctc gtcgtctggc cggaccacgc tatctgtgca aggtccccgg   1380
acgcgcgctc catgagcaga gcgcccgccg ccgaggcaag actcgggcgg cgccctgccc   1440
gtcccaccag gtcaacaggc ggtaaccggc ctcttcatcg ggaatgcgcg cgaccttcag   1500
catcgccggc atgtcccctg gcggacggga agtatcagct cgaccaagct ggcgagatt   1560
ttcaggagct aaggaagcta aaatggagaa aaaaatcact ggatatacca ccgttgatat   1620
atcccaatgg catcgtaaag aacattttga ggcatttcag tcagttgctc aatgtaccta   1680
taaccagacc gttcagctgc attaatgaat cggccaacgc gcgggagag gcggtttgcg   1740
tattgggcgc tcttccgctt cctcgctcac tgactcgctg cgctcggtcg ttcggctgcg   1800
gcgagcggta tcagctcact caaagtcggt aatacggtta tccacagaat cagggataa   1860
cgcaggaaag aacatgtgag caaaaggcca gcaaaaggcc aggaaccgta aaaaggccgc   1920
gttgctggcg ttttccata ggctccgccc ccctgacgag catcacaaaa atcgacgctc   1980
aagtcagagg tggcgaaacc cgacaggact ataaagatac caggcgtttc ccctggaag   2040
ctccctcgtg cgctctcctg ttccgaccct gccgcttacc ggatacctgt ccgcctttct   2100
cccttcggga agcgtggcgc tttctcaatg ctcacgctgt aggtatctca gttcggtgta   2160
ggtcgttcgc tccaagctgg gctgtgtgca cgaacccccc gttcagcccg accgctgcgc   2220
cttatccggt aactatcgtc ttgagtccaa cccggtaaga cacgacttat cgccactgga   2280
agcagccact ggtaacagga ttagcagagc gaggtatgta ggcggtgcta cagagttctt   2340
gaagtggtgg cctaactacg gctacactag aaggacagta tttggtatct gcgctctgct   2400
gaagccagtt accttcggaa aaagagttgg tagctcttga tccggcaaac aaaccaccgc   2460
tggtagcggt ggtttttttg tttgcaagca gcagattacg cgcagaaaaa aaggatctca   2520
agaagatcct ttgatctttt ctacggggtc tgacgctcag tggaacgaaa actcacgtta   2580
agggattttg gtcatgagat tatcaaaaag gatcttcacc tagatccttt taaattaaaa   2640
atgaagtttt aaatcaatct aaagtatata tgagtaaact tggtctgaca gttaccaatg   2700
cttaatcagt gaggcaccta tctcagcgat ctgtctattt cgttcatcca tagttgcctg   2760
actccccgtc gtgtagataa ctacgatacg ggagggctta ccatctggcc ccagtgctgc   2820
aatgataccg cgagacccac gctcaccggc tccagattta tcagcaataa accagccagc   2880
cggaagggcc gagcgcagaa gtggtcctgc aactttatcc gcctccatcc agtctattaa   2940
ttgttgccgg gaagctagag taagtagttc gccagttaat agtttgcgca acgttgttgc   3000
cattgctaca ggcatcgtgt ggtcacgctc gtcgtttggt atggcttcat tcagctccgg   3060
ttcccaacga tcaaggcgag ttacatgatc ccccatgttg tgcaaaaaag cggttagctc   3120
cttcggtcct ccgatcgttg tcagaagtaa gttggccgca gtgttatcac tcatggttat   3180
ggcagcactg cataattctc ttactgtcat gccatccgta agatgctttt ctgtgactgg   3240
```

```
tgagtactca accaagtcat tctgagaata gtgtatgcgg cgaccgagtt gctcttgccc    3300
gtcgtcaata cgggataata ccgcgccaca tagcagaact ttaaaagtgc tcatcattgg    3360
aaaacgttct cgggggcgaa aactctcaag gatcttaccg ctgttgagat ccagttcgat    3420
gtaacccact cgtgcaccca actgatcttc agcatctttt actttcacca gcgtttctgg    3480
gtgagcaaaa acaggaaggc aaaatgccgc aaaaaaggga ataagggcga cacggaaatg    3540
ttgaatactc atactcttcc tttttcaata ttattgaagc atttatcagg gttattgtct    3600
catgagcgga tacatatttg aatgtattta gaaaaataaa caaataggg ttccgcgcac     3660 atttccccga aaagtgccac ctgacgtcta agaaaccatt attatcatga cattaaccta    3720
taaaaatagg cgtatcacga ggccctttcg tc                                  3752

<210> SEQ ID NO 9
<211> LENGTH: 4382
<212> TYPE: DNA
<213> ORGANISM: Artificial Sequence
<220> FEATURE:
<223> OTHER INFORMATION: Vector for transforming supporting cell with a
      foreign to express a gene product of interest

<400> SEQUENCE: 9
ctcgagttta ccactcccta tcagtgatag agaaaagtga agtcgagtt taccactccc      60 tatcagtgat agagaaaagt gaaagtcgag tttaccactc cctatcagtg atagagaaaa    120
gtgaaagtcg agtttaccac tccctatcag tgatagagaa aagtgaaagt cgagtttacc    180
actccctatc agtgatagag aaaagtgaaa gtcgagttta ccactcccta tcagtgatag    240
agaaaagtga agtcgagtt taccactccc tatcagtgat agagaaaagt gaaagtcgag    300
ctcggtaccc gggtcgagta ggcgtgtacg gtgggaggcc tatataagca gagctcgttt    360
agtgaaccgt cagatcgcct ggagacgcca tccacgctgt tttgacctcc atagaagaca    420
ccgggaccga tccagcctcc gcggccccga attcctgcag cccatgcact tgcaaagggc    480
tctggtagtc ctggccctgc tgaacttggc cacaatcagc ctctctctgt ccacttgcac    540
cacgttggac ttcggccaca tcaagaagaa gagggtggaa gccattaggg gacagatctt    600
gagcaagctc aggctcacca gccccccctga gccatcggtg atgacccacg tcccctatca    660
ggtcctggca ctttacaaca gcacccggga gttgctggaa gagatgcacg gggagaggga    720
ggaaggctgc actcaggaga cctcggagtc tgagtactat gccaaagaga tccataaatt    780
cgacatgatc cagggactgg cggagcacaa tgaactggcc gtctgcccca aggaattac     840 ctctaaggtt tttcgtttca atgtgtcctc agtggagaaa aatggaacca atctgttccg    900
ggcagagttc cgggtcttgc gggtgcccaa ccccagctcc aagcgcacag agcagagaat    960
tgagctcttc cagatacttc gaccggatga gcacatagcc aagcagcgct acatagtg   1020 caagaatctg cccacaaggg gcaccgctga atggctgtct ttcgatgtca ctgacactgt   1080
gcgcgagtgg ctgttgagga gagagtccaa cttgggtctg gaaatcagca tccactgtcc   1140
atgtcacacc tttcagccca atggagacat actggaaaat gttcatgagg tgatggaaat   1200
caaattcaaa ggagtggaca atgaagatga ccatggccgt ggagacctgg ggcgtctcaa   1260
gaagcaaaag gatcaccaca acccacacct gatcctcatg atgatccccc cacaccgact   1320
ggacagccca ggccagggca gtcagaggaa gaagagggcc ctggacacca attactgctt   1380
ccgcaacctg gaggagaact gctgtgtacg cccccttat attgacttcc ggcaggatct   1440
aggctggaaa tgggtccacg aacctaaggg ttactatgcc aacttctgct caggcccttg   1500
```

```
cccatacctc cgcagcgcag acacaaccca tagcacggtg cttggactat acaacaccct   1560
gaacccagag gcgtctgcct cgccatgctg cgtcccccag gacctggagc ccctgaccat   1620
cttgtactat gtgggcagaa cccccaaggt ggagcagctg tccaacatgg tggtgaagtc   1680
gtgtaagtgc agctgagggg gatccactag ttctagagga tccagacatg ataagataca   1740
ttgatgagtt tggacaaacc acaactagaa tgcagtgaaa aaaatgcttt atttgtgaaa   1800
tttgtgatgc tattgctttta tttgtaacca ttataagctg caataaacaa gttaacaaca   1860
acaattgcat tcattttatg tttcaggttc aggggaggt gtgggaggtt ttttaaagca   1920
agtaaaacct ctacaaatgt ggtatggctg attatgatcc tgcaagcctc gtcgtctggc   1980
cggaccacgc tatctgtgca aggtccccgg acgcgcgctc catgagcaga gcgcccgccg   2040
ccgaggcaag actcggcgg cgccctgccc gtcccaccag gtcaacaggc ggtaaccggc   2100
ctcttcatcg ggaatgcgcg cgaccttcag catcgccggc atgtcccctg gcggacggga   2160
agtatcagct cgaccaagct tggcgagatt tcaggagct aaggaagcta aaatggagaa   2220
aaaaatcact ggatatacca ccgttgatat atcccaatgg catcgtaaag aacattttga   2280
ggcatttcag tcagttgctc aatgtaccta taaccagacc gttcagctgc attaatgaat   2340
cggccaacgc gcggggagag gcggtttgcg tattgggcgc tcttccgctt cctcgctcac   2400
tgactcgctg cgctcggtcg ttcggctgcg gcgagcggta tcagctcact caaagtcggt   2460
aatacggtta tccacagaat caggggataa cgcaggaaag aacatgtgag caaaaggcca   2520
gcaaaaggcc aggaaccgta aaaaggccgc gttgctggcg ttttccata ggctccgccc   2580 ccctgacgag catcacaaaa atcgacgctc aagtcagagg tggcgaaacc cgacaggact   2640
ataaagatac caggcgtttc cccctggaag ctccctcgtg cgctctcctg ttccgaccct   2700
gccgcttacc ggatacctgt ccgcctttct cccttcggga agcgtggcgc tttctcaatg   2760
ctcacgctgt aggtatctca gttcggtgta ggtcgttcgc tccaagctgg gctgtgtgca   2820 cgaaccccc gttcagcccg accgctgcgc cttatccggt aactatcgtc ttgagtccaa   2880
cccggtaaga cacgacttat cgccactgga agcagccact ggtaacagga ttagcagagc   2940
gaggtatgta ggcggtgcta cagagttctt gaagtggtgg cctaactacg gctacactag   3000
aaggacagta tttggtatct gcgctctgct gaagccagtt accttcggaa aaagagttgg   3060
tagctcttga tccggcaaac aaaccaccgc tggtagcggt ggtttttttg tttgcaagca   3120
gcagattacg cgcagaaaaa aaggatctca agaagatcct ttgatctttt ctacggggtc   3180
tgacgctcag tggaacgaaa actcacgtta agggattttg gtcatgagat tatcaaaaag   3240
gatcttcacc tagatccttt taaattaaaa atgaagtttt aaatcaatct aaagtatata   3300
tgagtaaact tggtctgaca gttaccaatg cttaatcagt gaggcaccta tctcagcgat   3360
ctgtctattt cgttcatcca tagttgcctg actccccgtc gtgtagataa ctacgatacg   3420
ggagggctta ccatctggcc ccagtgctgc aatgataccg cgagacccac gctcaccggc   3480
tccagattta tcagcaataa accagccagc cggaagggcc gagcgcagaa gtggtcctgc   3540
aactttatcc gcctccatcc agtctattaa ttgttgccgg gaagctagag taagtagttc   3600
gccagttaat agtttgcgca acgttgttgc cattgctaca ggcatcgtgt ggtcacgctc   3660
gtcgtttggt atggcttcat tcagctccgg ttcccaacga tcaaggcgag ttacatgatc   3720
ccccatgttg tgcaaaaaag cggttagctc cttcggtcct ccgatcgttg tcagaagtaa   3780
gttggccgca gtgttatcac tcatggttat ggcagcactg cataattctc ttactgtcat   3840
```

-continued

```
gccatccgta agatgctttt ctgtgactgg tgagtactca accaagtcat tctgagaata    3900
gtgtatgcgg cgaccgagtt gctcttgccc gtcgtcaata cgggataata ccgcgccaca    3960
tagcagaact ttaaaagtgc tcatcattgg aaaacgttct cggggcgaaa actctcaag    4020
gatcttaccg ctgttgagat ccagttcgat gtaacccact cgtgcaccca actgatcttc    4080
agcatctttt actttcacca gcgtttctgg gtgagcaaaa acaggaaggc aaaatgccgc    4140
aaaaaaggga ataagggcga cacggaaatg ttgaatactc atactcttcc ttttcaata    4200
ttattgaagc atttatcagg gttattgtct catgagcgga tacatatttg aatgtattta    4260
gaaaaataaa caataggggt tccgcgcac atttccccga aaagtgccac ctgacgtcta    4320
agaaaccatt attatcatga cattaaccta taaaaatagg cgtatcacga ggcccttcg    4380
tc                                                                  4382
```

<210> SEQ ID NO 10
<211> LENGTH: 4224
<212> TYPE: DNA
<213> ORGANISM: Plasmid pUHD10.3-hflt3-Ligand-exon 6

<400> SEQUENCE: 10

```
ctcgagttta ccactcccta tcagtgatag agaaaagtga agtcgagtt taccactccc     60
tatcagtgat agagaaaagt gaaagtcgag tttaccactc cctatcagtg atagagaaaa    120
gtgaaagtcg agtttaccac tccctatcag tgatagagaa aagtgaaagt cgagtttacc    180
actccctatc agtgatagag aaaagtgaaa gtcgagttta ccactcccta tcagtgatag    240
agaaaagtga agtcgagtt taccactccc tatcagtgat agagaaaagt gaaagtcgag    300
ctcggtaccc gggtcgagta ggcgtgtacg gtgggaggcc tatataagca gagctcgttt    360
agtgaaccgt cagatcgcct ggagacgcca tccacgctgt tttgacctcc atagaagaca    420
ccgggaccga tccagcctcc gcggccccga attccgggc cccggccga atgacagtg      480
ctggcgccag cctggagccc aacaacctat ctcctcctgc tgctgctgct gagctcggga    540
ctcagtggga cccaggactg ctccttccaa cacagcccca tctcctccga cttcgctgtc    600
aaaatccgtg agctgtctga ctacctgctt caagattacc cagtcaccgt ggcctccaac    660
ctgcaggacg aggagctctg cggggggcctc tggcggctgg tcctggcaca gcgctggatg    720
gagcggctca agactgtcgc tgggtccaag atgcaaggct tgctggagcg cgtgaacacg    780
gagatacact ttgtcaccaa atgtgccttt cagccccccc ccagctgtct tcgcttcgtc    840
cagaccaaca tctcccgcct cctgcaggag acctccgagc agctggtggc gctgaagccc    900
tggatcactc gccagaactt ctcccggtgc ctggagctgc agtgtcagcc cgtagagacg    960
gtgtttcacc gtgtcagcca ggatggtctc gatctcctga cctcgtgatc tgcccgcctc   1020
ggcctcccaa agtgctagga ttacagatac tcctcaaccc tgccacccc atggagtccc   1080
cggcccctgg aggccacagc cccgacagcc cgcagcccc tctgctcct ctactgctg     1140
ctgcccgtgg gcctcctgct gctggccgct gcctggtgcc tgcactggca gaggacgcgg   1200
cggaggacac cccgccctgg ggagcaggtg ccccccgtcc cagtcccca ggacctgctg    1260
cttgtggagc actgacctgg ccaaggcctc atcctgcgga gccttaaaca acgcagtgag   1320
acagacatct atcatcccat tttacagggg aggatactga ggcacacaga ggggagtcac   1380
cagccagagg atgtatagcc tggacacaga ggaagttggc tagaggccgg tcccttcctt   1440
gggcccctct cattccctcc ccagaatgga ggcaacgcca gaatccagca ccggcccat   1500
ttacccaact ctgaacaaag cccccggaat tcgagctcgg tacccgggga tcctctagag   1560
```

```
gatccagaca tgataagata cattgatgag tttggacaaa ccacaactag aatgcagtga   1620
aaaaaatgct ttatttgtga aatttgtgat gctattgctt tatttgtaac cattataagc   1680
tgcaataaac aagttaacaa caacaattgc attcatttta tgtttcaggt tcagggggag   1740
gtgtgggagg ttttttaaag caagtaaaac ctctacaaat gtggtatggc tgattatgat   1800
cctgcaagcc tcgtcgtctg gccggaccac gctatctgtg caaggtcccc ggacgcgcgc   1860
tccatgagca gagcgcccgc cgccgaggca agactcgggc ggcgccctgc ccgtcccacc   1920
aggtcaacag gcggtaaccg gcctcttcat cgggaatgcg cgcgaccttc agcatcgccg   1980
gcatgtcccc tggcggacgg gaagtatcag ctcgaccaag cttggcgaga ttttcaggag   2040
ctaaggaagc taaaatggag aaaaaaatca ctggatatac caccgttgat atatcccaat   2100
ggcatcgtaa agaacatttt gaggcatttc agtcagttgc tcaatgtacc tataaccaga   2160
ccgttcagct gcattaatga atcggccaac gcgcggggag aggcggtttg cgtattgggc   2220
gctcttccgc ttcctcgctc actgactcgc tgcgctcggt cgttcggctg cggcgagcgg   2280
tatcagctca ctcaaaggcg gtaatacggt tatccacaga atcaggggat aacgcaggaa   2340
agaacatgtg agcaaaaggc cagcaaaagg ccaggaaccg taaaaaggcc gcgttgctgg   2400
cgttttccca taggctccgc cccctgacg agcatcacaa aaatcgacgc tcaagtcaga   2460
ggtggcgaaa cccgacagga ctataaagat accaggcgtt tccccctgga agctccctcg   2520
tgcgctctcc tgttccgacc ctgccgctta ccggatacct gtccgccttt ctcccttcgg   2580
gaagcgtggc gctttctcaa tgctcacgct gtaggtatct cagttcggtg taggtcgttc   2640
gctccaagct gggctgtgtg cacgaacccc ccgttcagcc cgaccgctgc gccttatccg   2700
gtaactatcg tcttgagtcc aacccggtaa gacacgactt atcgccactg gcagcagcca   2760
ctggtaacag gattagcaga gcgaggtatg taggcggtgc tacagagttc ttgaagtggt   2820
ggcctaacta cggctacact agaaggacag tatttggtat ctgcgctctg ctgaagccag   2880
ttaccttcgg aaaaagagtt ggtagctctt gatccggcaa acaaaccacc gctggtagcg   2940
gtggtttttt tgtttgcaag cagcagatta cgcgcagaaa aaaaggatct caagaagatc   3000
ctttgatctt ttctacgggg tctgacgctc agtggaacga aaactcacgt taagggattt   3060
tggtcatgag attatcaaaa aggatcttca cctagatcct tttaaattaa aaatgaagtt   3120
ttaaatcaat ctaaagtata tatgagtaaa cttggtctga cagttaccaa tgcttaatca   3180
gtgaggcacc tatctcagcg atctgtctat ttcgttcatc catagttgcc tgactccccg   3240
tcgtgtagat aactacgata cgggagggct taccatctgg ccccagtgct gcaatgatac   3300
cgcgagaccc acgctcaccg gctccagatt tatcagcaat aaaccagcca gccgaaggg    3360 ccgagcgcag aagtggtcct gcaactttat ccgcctccat ccagtctatt aattgttgcc   3420
gggaagctag agtaagtagt tcgccagtta atagtttgcg caacgttgtt gccattgcta   3480
caggcatcgt ggtgtcacgc tcgtcgtttg gtatggcttc attcagctcc ggttcccaac   3540
gatcaaggcg agttacatga tcccccatgt tgtgcaaaaa agcggttagc tccttcggtc   3600
ctccgatcgt tgtcagaagt aagttggccg cagtgttatc actcatggtt atggcagcac   3660
tgcataattc tcttactgtc atgccatccg taagatgctt ttctgtgact ggtgagtact   3720
caaccaagtc attctgagaa tagtgtatgc ggcgaccgag ttgctcttgc ccggcgtcaa   3780
tacgggataa taccgcgcca catagcagaa ctttaaaagt gctcatcatt ggaaaacgtt   3840
cttcggggcg aaaactctca aggatcttac cgctgttgag atccagttcg atgtaaccca   3900
```

-continued

```
ctcgtgcacc caactgatct tcagcatctt ttactttcac cagcgtttct gggtgagcaa    3960
aaacaggaag gcaaaatgcc gcaaaaaagg gaataagggc gacacggaaa tgttgaatac    4020
tcatactctt cctttttcaa tattattgaa gcatttatca gggttattgt ctcatgagcg    4080
gatacatatt tgaatgtatt tagaaaaata aacaaatagg ggttccgcgc acatttcccc    4140
gaaaagtgcc acctgacgtc taagaaacca ttattatcat gacattaacc tataaaaata    4200
ggcgtatcac gaggcccttt cgtc                                           4224
```

METHOD FOR GROWING STEM CELLS ON GENETICALLY MODIFIED SUPPORTER CELLS

This application is a continuation of Ser. No. 09/957,458, filed Sep. 21, 2001, now abandoned which is a continuation-in-part of PCT/EP00/08247, filed Aug. 24, 2000.

This is a continuation-in-part of PCT/EP00/08247 filed Aug. 24, 2000, the disclosure of which is incorporated herein by reference.

The present invention is related to a method for growing stem cells.

Stem cells are commonly defined as cells which exist for the lifetime of an organism and are able to undergo symmetric and/or asymmetric divisions, to give rise to further stem cells (for preservation of the stem cell pool) and to more differentiated cells with defined life-time (for organ-specific functions). Due to this unique property they are ideal vehicles for somatic gene therapy. They would maintain the transgene for the life-time of the tissue and the organism, and would carry the transgene expression into the differentiated cells. Stem cells may be totipotent (e.g. embryonic stem cells), pluripotent (e.g. hematopoietic stem cells, neural glial stem cells, hepatocyte stem cells, chondrocytic stem cells) or unipotent (e.g. keratinocytic stem cells, muscle precursor cells, tracheal epithelial precursor cells).

Stem cells are plastic, can become trans-lineaged and/or reprogrammed in different microenvironments formed by supporting cells. Both stem cells and supporting cells can be genetically processed by way of molecular breeding and/or cellular breeding, i.e. cell fusion after genetic manipulation.

Cellular breeding is defined as cell fusion after molecular manipulation. This Cellular Breeding process (Trade Mark-to-be) can be speeded up by combining the cell fusion of cell-cell with Molecular Breeding™ process (Maxi-gene Incl. Redwood city, Calif.).

EP-A-0753 574 discloses a method and a composition of a culture medium are provided for obtaining ex vivo human progenitor cell expansion. The culture medium comprises human progenitor and/or stem cells, stromal cells and growth factors. The culture medium is replaced substantially continuously at a rate sufficient to maintain an effective growth environment for expansion of progenitor cells, and at least one portion of the stromal cells are transformed fibroblast cells capable of excreting at least one growth factor which directs the proliferation and/or differentiation of said human progenitor and/or stem cells.

M. Gossen et al. disclose a tight control of gene expression in mammalian cells by tetracycline-responsive promoters (PNAS, USA Vol. 89, 5547-5551, 1992).

Although being the aim of many research projects, it has until now being very difficult to grow stem cells, especially lineage-committed stem cells, thereby controlling expansion and differentiation of the stem cells.

The present invention provides a method for growing stem cells comprising the steps of providing stem cells with supporters said supporters being genetically modified in order to provide externally regulatable interactions between the supporters and the stem cells;

applying an external signal for starting or stopping the interactions.

According to the present invention, stem cells are co-incubated with supporters. These supporters are genetically modified to allow a regulatable interaction with the stem cells. Supporters and stem cells are interchangeable upon genetic modification, processing, and interaction. These interactions between the supporters and the stem cells are externally regulatable. "Externally regulatable" means that the interaction between the supporters and the stem cells is regulated from outside of the supporters.

Preferably, the interactions are based on the secretion or display of substances. These substances, which are secreted or displayed by the supporters control the development of the stem cells. The expansion or differentiation of the stem cells is indirectly controlled by the regulatable interactions of the supporters.

Preferably as external signals may serve the addition or removal of substances, heat, light, sound, odor, taste, touch (mechanics), and/or electromagnetic waves. The only requirement is that these external signals are able to regulate the interactions between the supporters and the stem cells.

Preferably, the supporters are cells. They may be stem cells or non-stem cells. In a preferred embodiment these supporters are forming a micro-environment.

The supporting cells can be further transformed with foreign genes to express a gene product of interest e.g. a protein of the clotting cascade, insulin, enzymes, antibodies, growth factors or the like. The supporting cells can be further mutated, processed, and/or molecular, cellular bred in order to express (a) gene product(s) of interests.

It is believed that the supporters form a micro-environment thus providing cytokines and adhesion molecules as well as direct contact between the stem cells and the supporters. Suitable supporters are skin cells, tracheal and lung cells, bone marrow stroma cells, hepatic stroma cells, glial cells or tissue cells or "spore"-like stem cells.

"Spore"-Like Stem Cells:

Somatic stem cells so far described in the literature have well published criteria using specific markers, morphology, size, biological function, etc. Besides this known kind of cells, there is another new type of somatic stem cells— "spore"-like stem cells. They exist in every tissues examined, and also in the embryonic bodies differentiated in vitro from embryonic stem (ES) cells.

They are smaller than erythrocytes, 5 µm and less in diameter, DAPI positive. They are quiescent, i.e., non-proliferating, and they do not possess any histocompatibility antigen at this stage. They migrate in the body freely since they are small (cf. FIGS. 16 and 17).

In vivo, they can be triggered into proliferation and differentiation in situ in all tissues when microenvironment allows.

In vitro, when cultured tissue cells are centrifuged using conventional cell centrifugation condition, i.e., at 1200-1500 rpm (250-350×g) for 5 minutes using a cell centrifuge, conventional cells are in the pellet fraction. The "spore" like cells remain in the supernatant. When the supernatant is seeded in a petric-dish and incubated in a $CO_2$ incubator at the body temperature and under low oxygen condition, they will be triggered to expand and to adherent to the petric dish, becoming visible like any conventional cells under the microscope. The low oxygen condition can be achieved either by lightening a candle in the $CO_2$ incubator and closing the door, or by circulating the air in the incubator with high nitrogen concentration. Upon triggering of such spore-like stem cells to landings the further expansion of stem cells needs appropriated micro-environment with growth factors, feeder cells, as described in the text.

Suitable secreted or displayed substances are cell based growth factors, protein growth factors, interleukines.

In particular, the supporters are genetically modified with a vector, and/or a set of vectors, and/or mutation and processing, molecular and cellular breeding, comprising a gene for the substances, e.g. interleukines, protooncogenes, oncogenes, cell cycle control genes, signal transduction genes, and/or cell based growth factors and a regulatable expression system.

A preferred regulatable expression system is the regulatable tetracycline expression system.

Preferred vectors for the transformation of the supporters are the vectors selected from the group consisting of pRetro-tet-off-E6/E7, pRetro-tet-off-(tTA deleted) E6/E7, pRetro-tet-off-U19-tsA58, pRetro-tet-off-SV40Tag, pRetro-tet-off-T2, pRetro-tet-off-BCL2, pUHD15.1-β-gal-NeoR, pUHD10.3-TGFβ3, pUHD10.3-hIL3, pUHD10.3-hIL6, pUHD10.3-hFlt3-ligand, pUHD10.3-hNGF, pUHD10.3-long CNTF, pUHD 10.3-long GDNF, pUHD 10.3-hIL2, pUHD 10.3-hIL7, pUHD 10.3-hIL4, pUHD 10.3-GMCSF, pD12YCVJC-long-CNTF, pD12YCVJC-long-GDNF, pD12YCVJC-short-CNTF and pD12YCVJC-short-GDNF, as well as pRetro-tet-on-(including pRetro-tet-ART)-derivatives, other pRetro-tet-off-(including pLP-TRE2 and pLP-RevTRE)-derivatives, adenoviral-derivatives, and lentiviral-derivatives.

Details on these vectors can be found in the examples and the figures (FIG. 18-28).

Cell lines obtainable by cellular modification, and molecular and cellular breeding of cell with the vectors of the present invention are subject of the invention. Cell lines further modified using mutation, genetic processing, cellular and molecular breedings, are also subject of the present invention.

The present invention further provides a method of curing diseases by gene therapy and/or cell therapy in combination with tissue engineering when the functional expression of stem cells is helped with the engineered architecture of the tissue, which diseases are related to insufficient, lack or disorder of stem cells, by administering to patients in need thereof, supporters being genetically modified in order to provide externally regulatable interactions between the supporters and the stem cells. Furthermore, any disease related to insufficient expression or activity of a protein or enzyme can be treated by administering supporters and/or stem cells after expansion in particular ex vivo. But it is also possible that a transformation can be performed in vivo.

Figure 3:
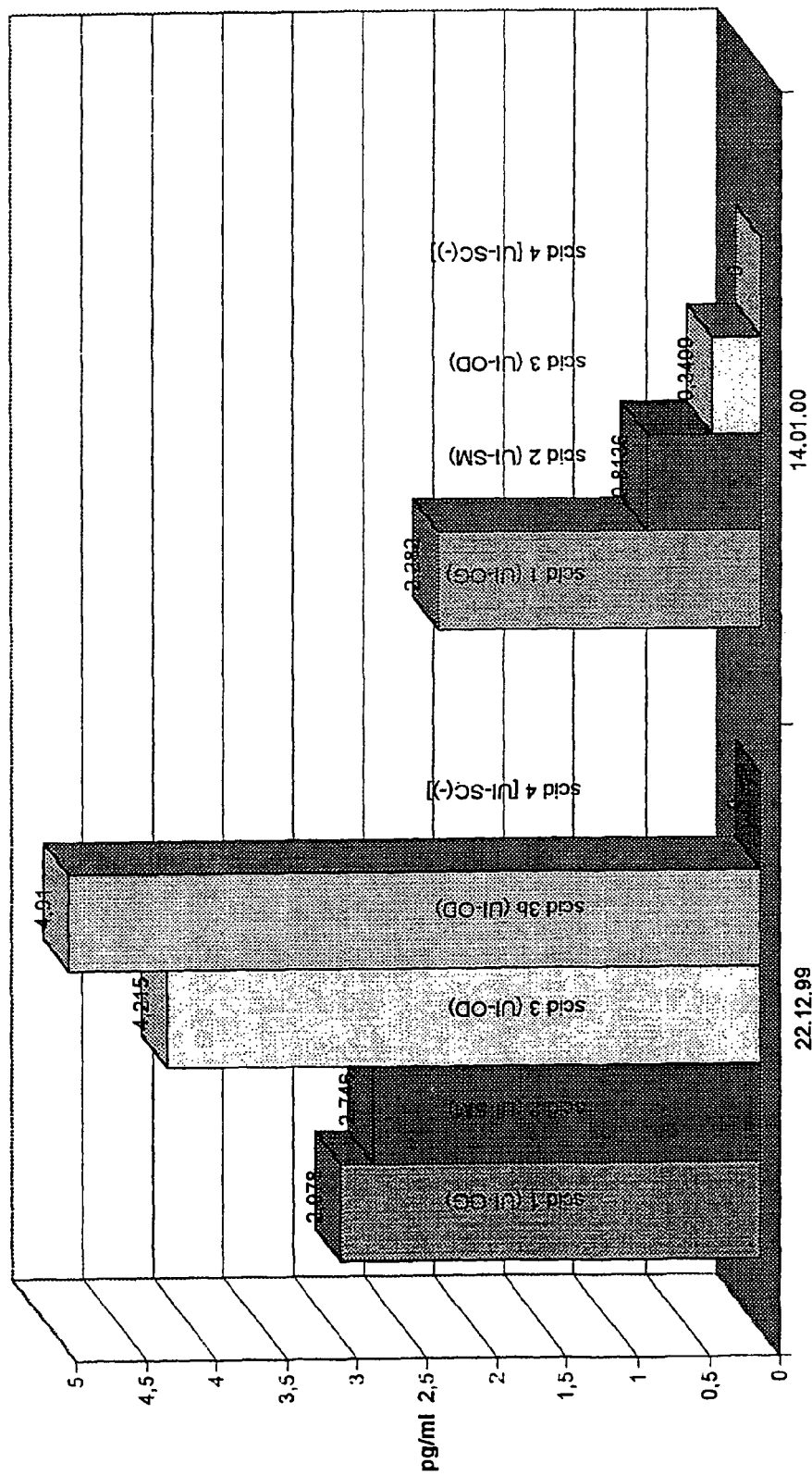
FIG. 3 shows the appearance of hIL-6 in scid-NOD mice.
Figure 3A:
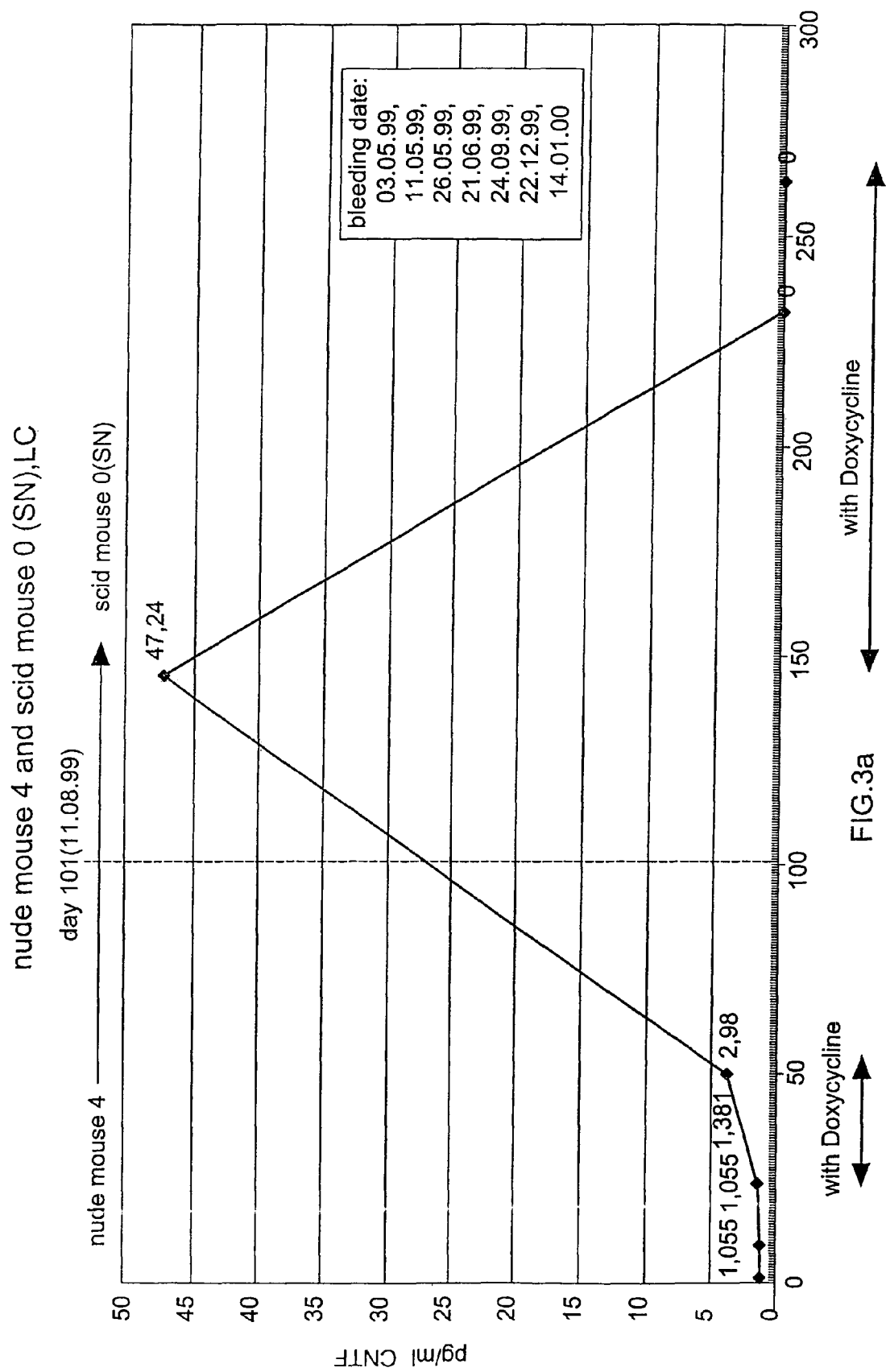
Figure 3B:
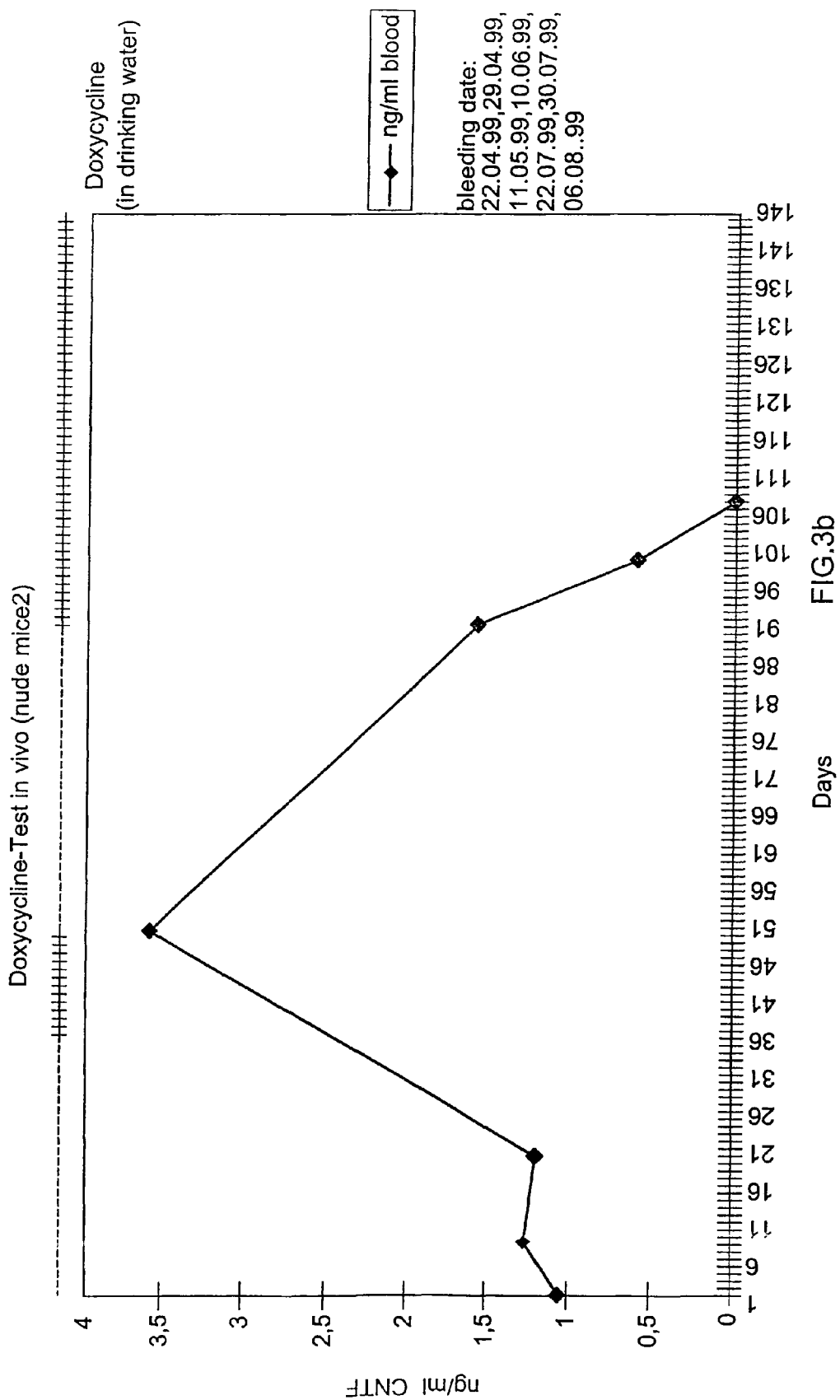

FIG. 3 *a* shows the appearance of CTNF depending on the addition/removal of doxycycline in vivo (nude mice).

FIG. 3 *b* shows the appearance of CNTF depending on the addition/removal of doxycycline in vivo (nude and scid NOD mice).

FIG. 4 shows the cloning of growth factor genes.

FIG. 5 to 15 show photographs of various cell cultures.

Figure 16:
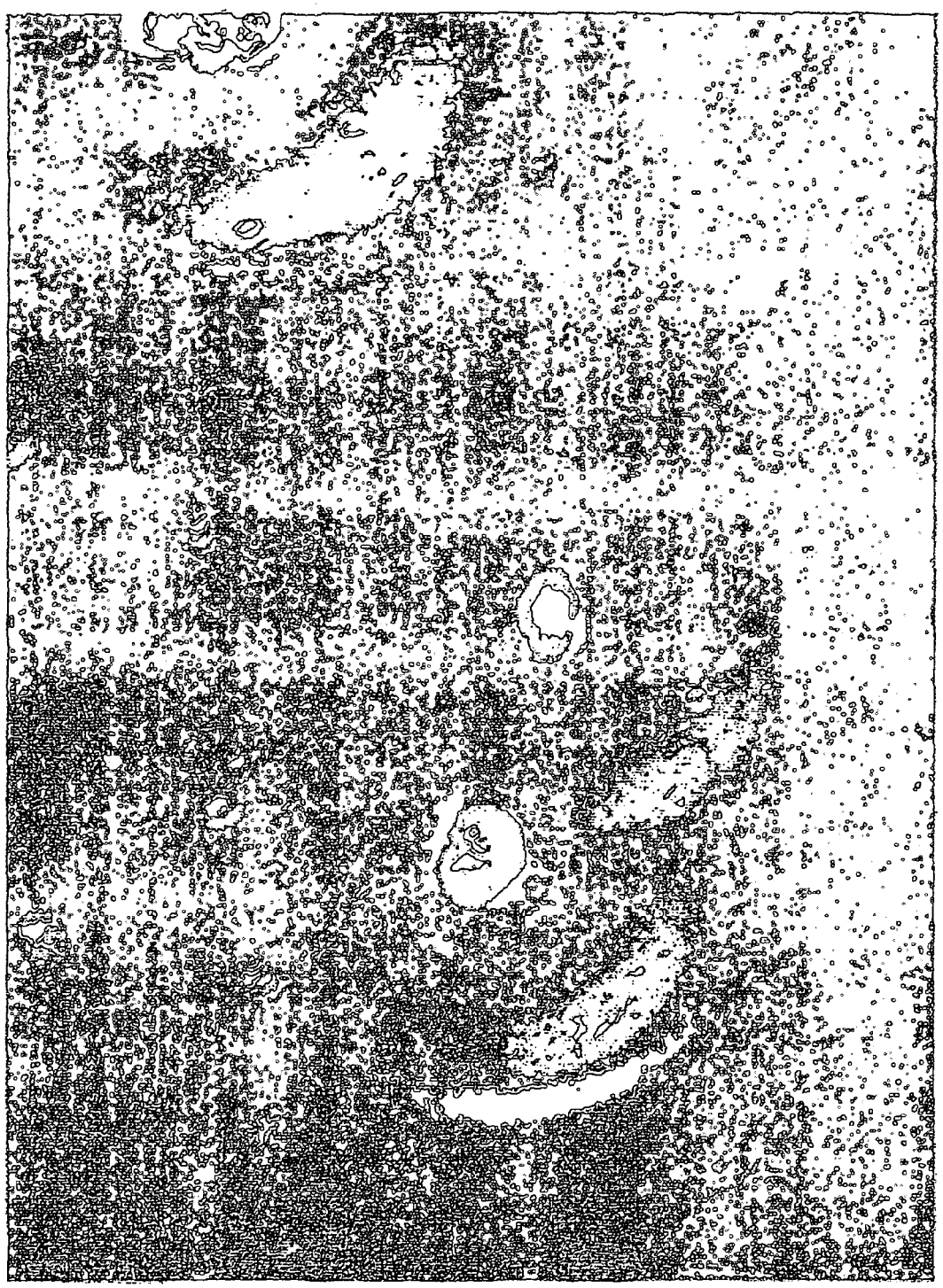
Figure 17:
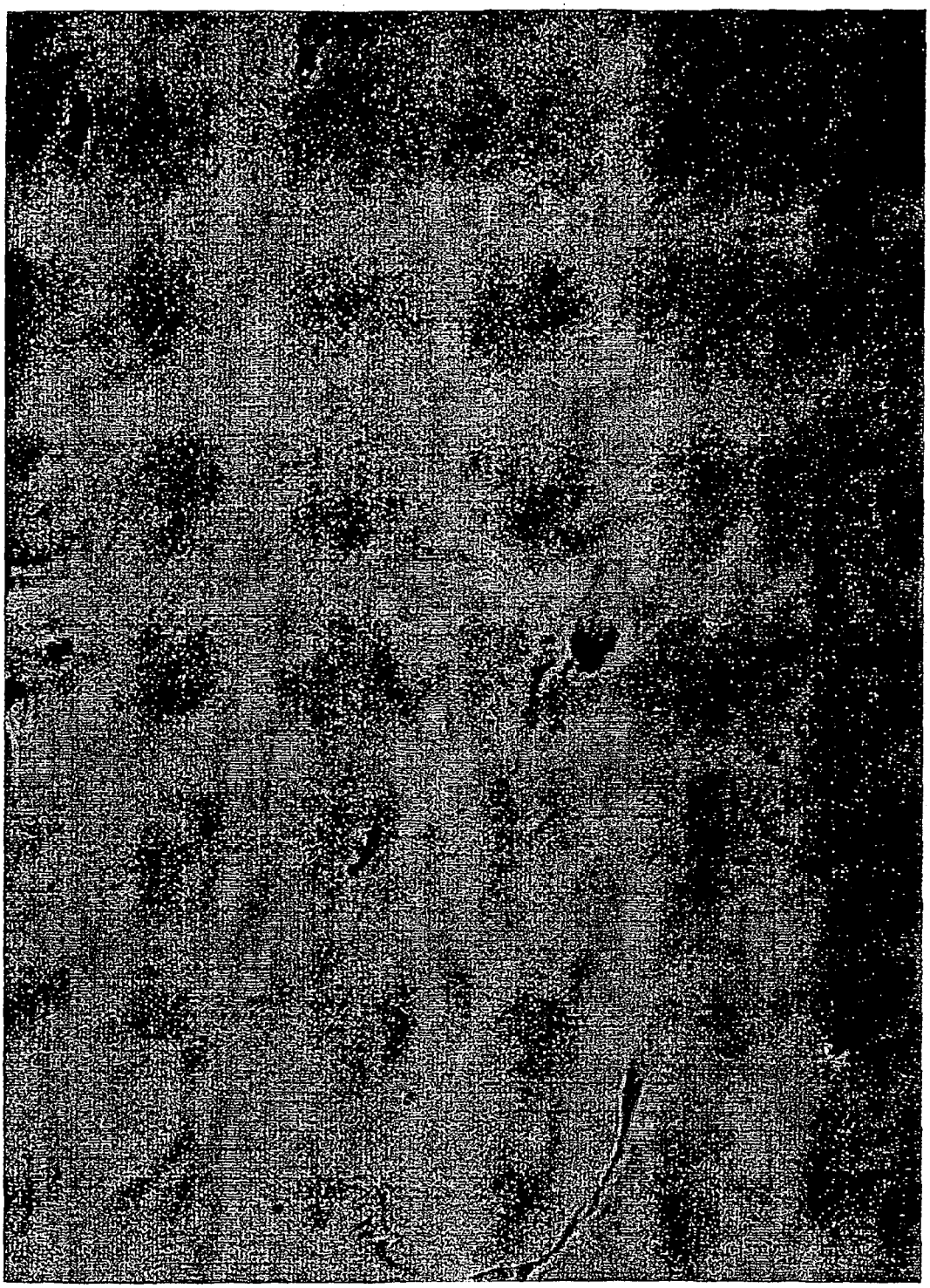

FIGS. 16 and 17 show "spore"-like stem cells.

FIG. 16 shows "spore"-like stem cells stained with DAPI and photographed through (a) DAPI-filter and (b) for phase contrast. The picture was obtained by superimposing (a) and (b).

FIG. 17 shows "spore"-like cells cultured under low $O_2$-condition to trigger them to adhere to the bottom of the petric-dish in order to become visible in phase-contrast microscopy.

Figure 21:
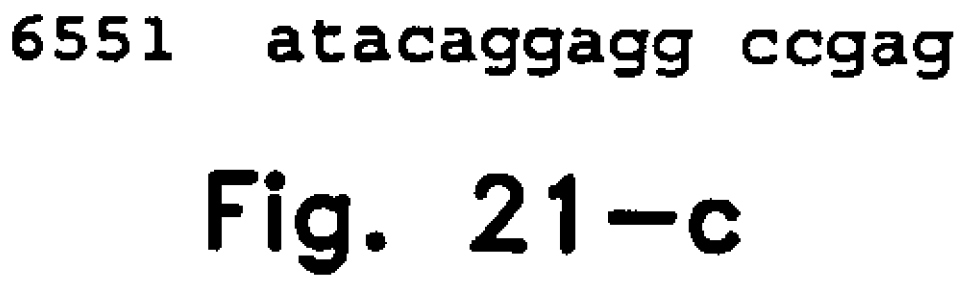

FIG. 18 to 26 show the sequences of vectors.

Figure 28:
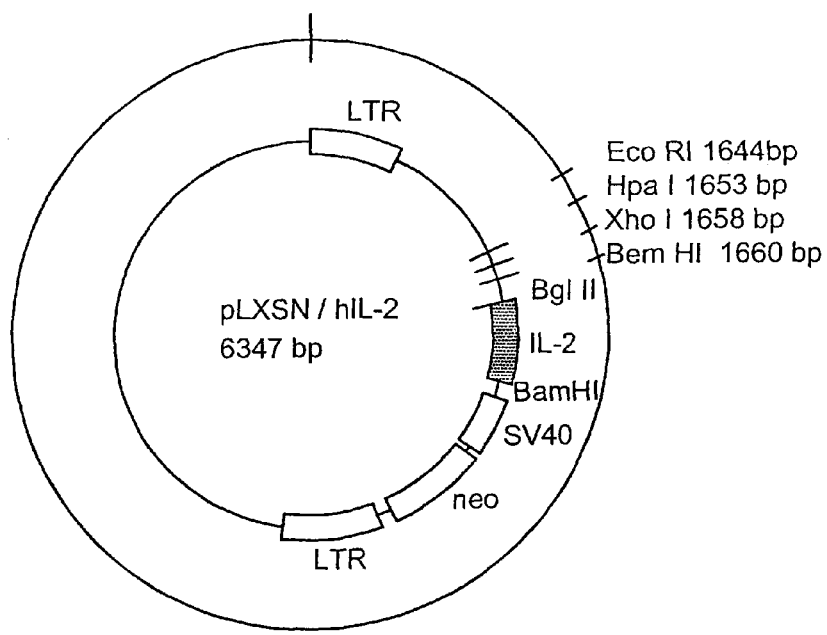

FIGS. 27 and 28 show the construction of a vector.

The method of the present invention is further explained by the following examples:

EXAMPLE 1 hIL6 Containing Transgenic-Keratinocytic Stem Cells Support the Growth of (Sister) Keratinocytic Stem Cells in Culture In these sets of experiments, ELISA assays were performed with supernates obtained from one hIL6 of construct teto-hIL6 containing keratinocytic stem cell clone derived from a CMV-tTA×teto-SV40 T antigen transgenic mouse, either cultured alone, or with doxycycline included in the culture for 0-12 h, 25-50 h. This experiment is to test whether the secretion of cytokines affects by doxycycline in culture.

hIL6 promotes the growth of CMV-tTA×teto-SV40 Tag transgenic keratinocytic stem cell line drastically by increasing cell numbers. At the presence of hIL6, the growth arrest at G1 compartment is abolished, and cells continue to grow in the presence of doxycycline.

The level of hIL6 in the supernates was slightly inhibited at time point of 12 h, and increase again at 50 h, up to the level of the control cells, i.e., without doxycycline. Thus, hIL6-containing clone continued to secrete hIL6 despite of the fact that doxycycline was included in the culture.

The data are interpreted as follow: Engineered stem cells support the growth of sister stem cells (internally or externally) in vitro by the combination of the following two mechanisms:

(1) The hIL6 engineered keratinocytic stem cells secrete hIL6 into supernate, target and promote the growth of sister keratinocytic stem cells—an external/heterocrine mechanism.

(2) The gene product of hIL6 engineered keratinocytic stem cells, acts intra-cytoplasmically, and promotes the growth of itself—an internal/autocrine mechanism.

In both events, hIL6 is able to maintain skin in the keratinocytic stem cells compartment, upon the withdraw of doxycycline.

EXAMPLE 2

Doxycycline-Regulatable Keratinocytic Stem Cells Promote the Differentiation of Keratinocytic Stem/Precursor Cells, while Doxycycline-Regulatable Keratinocytic Stem Cells Transgenic with hIL6 Inhibits the Differentiation of Keratinocytic Stem Cells Keratinocyte stem cells (possessing the markers of beta-integrin 1 high, involucrin negative) from CMV-tTA-teto-SV40Tag double transgenic mice (designated H3) and keratinocytic stem/precursor cells (possessing the markers of beta-integrin 1 low, involucrin positive) isolated from inbred mice (designated MK, provided by S. Broad) are co-cultured. MK cells are induced to differentiate to mature keratinocytes by expression of mature markers and cell morphology. MK cells become sheets of striated, long cells with darken color, while H3 cells maintain the stem cell morphology.

When keratinocytic stem cells transgenic with teto-hIL6 (designated H3hIL6) and MK are co-cultured, MK cells differentiate less, and H3hIL6 cells maintain in the stem cell compartment. The effect can be maintained up to 6 weeks in culture. The origin of cell types in the mixing population is identified using GFP (green fluorescent protein) inserted into H3, H3hIL6.

Figure 5:
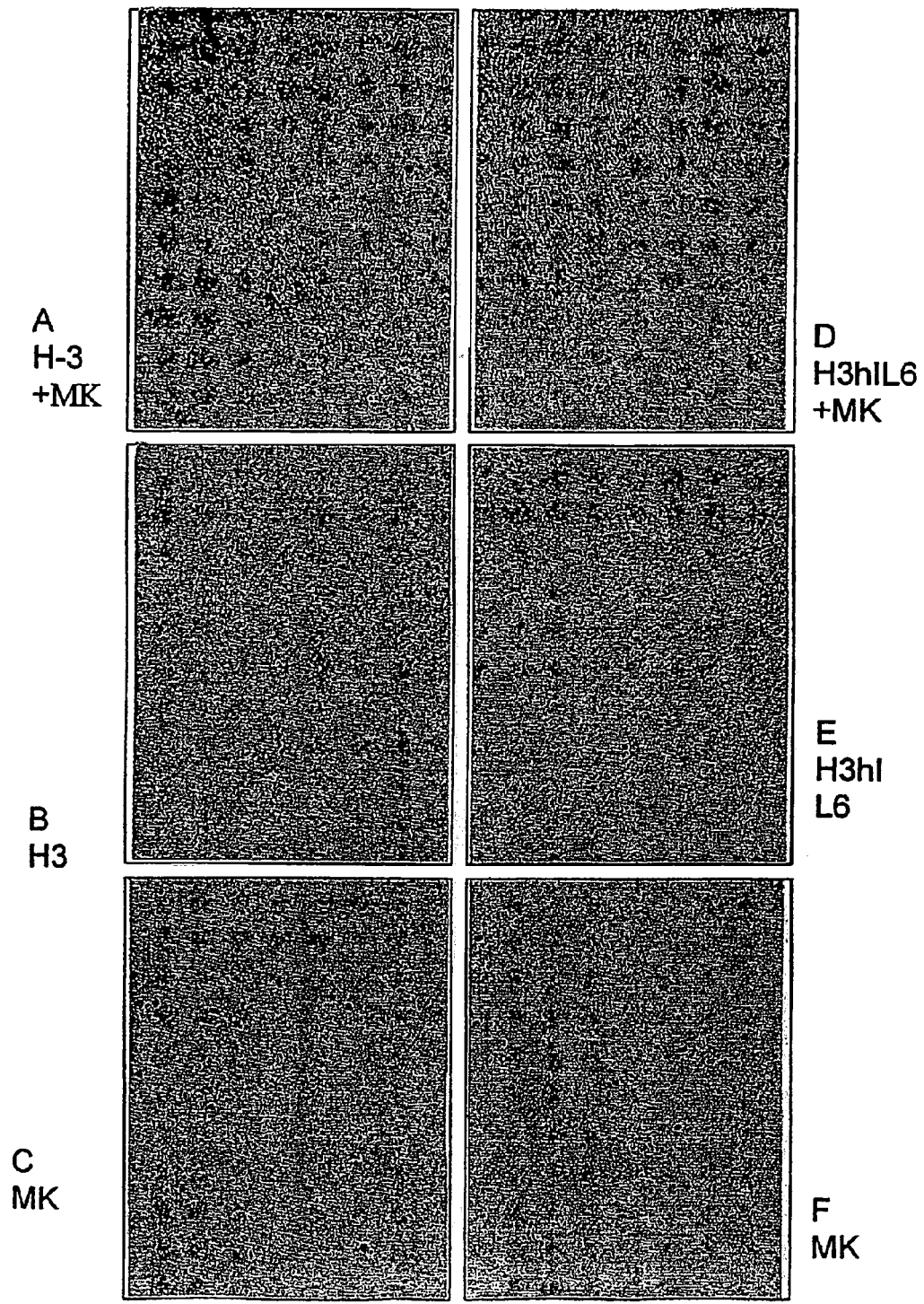

These experiments of morphological appearance by co-culture are shown in FIG. 5: panel A H3+MK, panel B H3 alone, panel C MK alone, panel D H3hIL6+MK, panel E H3hIL6 alone, panel F MK alone. Comparing panel D and panel A, it is shown that co-culture of H3hIL6+MK cells prevent the differentiation of MK cells (appearance of parental cell morphology), while co-culture of H3+MK cells induces the differentiation of MK cells (appearance of new cell morphology).

EXAMPLE 3

Figure 6:
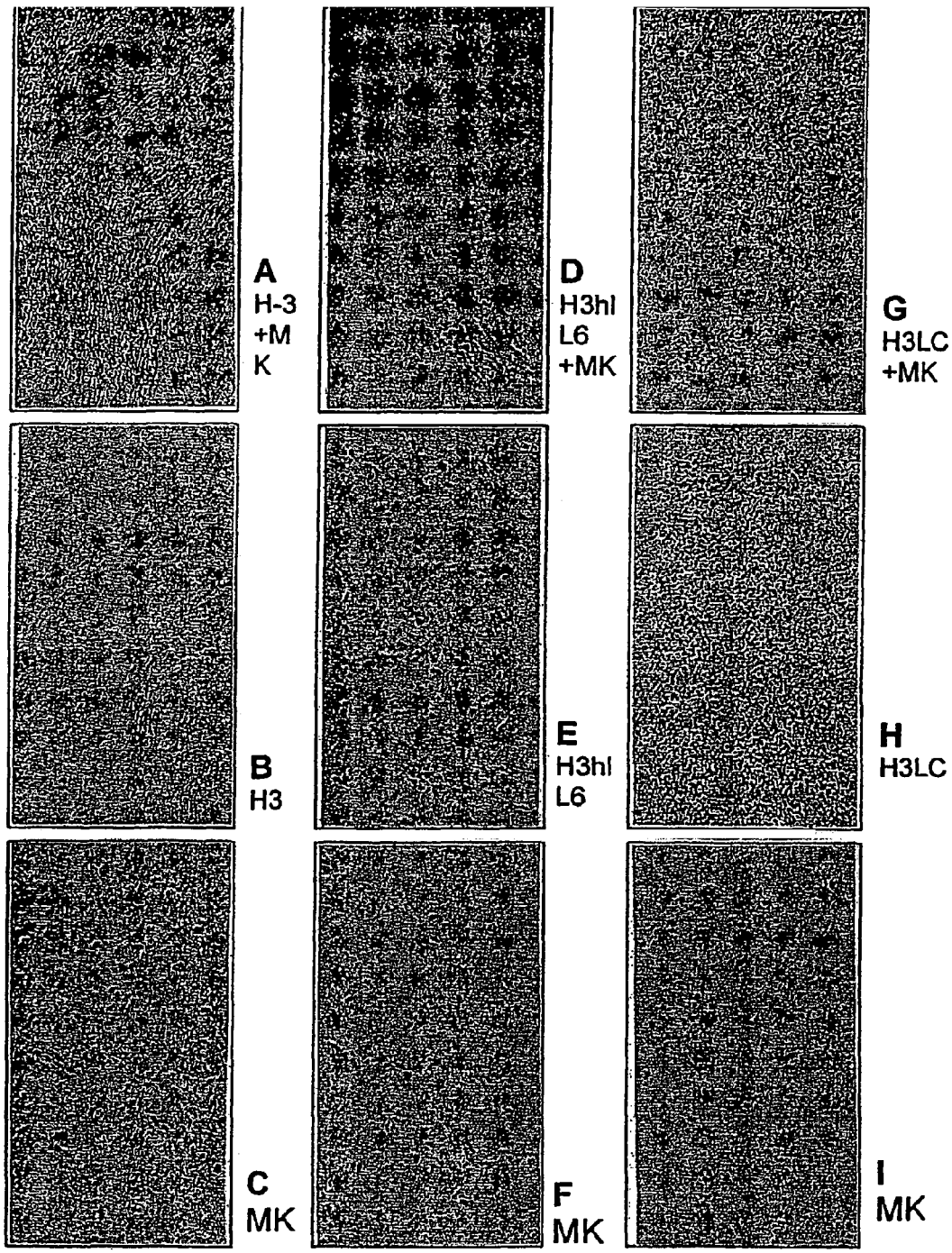

Doxycycline-Regulatable Keratinocytic Stem Cells Induce the Differentiation of Keratinocytic Stem Cells, while Doxycycline-Regulatable Keratinocytic Stem Cells Transgenic with hCNTF Promote the Growth of Stem Cells and Inhibit the Differentiation of Keratinocytic Stem/Precursor Cells The experiment is performed with keratinocytic stem cells transgenic with long JCVp-hCNTF (designated H3LC). Co-culture of H3+MK induces the differentiation of MK cells. However, co-culture of H3LC+MK prevents the differentiation of MK cells. Cell numbers of both populations are increased drastically and die quickly when depleted of nutrition and space. Thus, unlike hIL6, which promotes the survival of H3hIL6+MK cells, hCNTF promotes rapid cell division of H3LC+MK cells. The morphological appearance of cells is shown in FIG. 6, panel A H3+MK, panel B H3 alone, panel C MK alone, panel D H3hIL6+MK, panel E H3hIL6 alone, panel F MK alone, panel G H3LC+MK, panel H H3LC alone, panel I MK alone.

EXAMPLE 4

Cytokine-Secreting, Doxycycline-Regulatable Keratinocytic Stem Cells Influence the Differentiation of Keratinocytic Stem/Precursor Cells: it is a Cell-Mediated Event Soluble cytokine such as hIL6, hCNTF, or hIL3, was included in medium of the culture dish of MK+H3 cells, no obvious morphological change could be observed due to cytokines, i.e., MK+H3 showed the differentiation pattern. It is either the cytokine molecules are short-life or the anti-differentiation effect requires direct cell cell contact.

In order to distinguish these possibilities, we performed the following experiments: Cells were seeded on separated glass coverslips. Two coverslips of different cell type were placed in the same petric dishes with distance to prevent direct contact between two coverslips. As controls, coverslips of each cell type were cultured alone. After 3 weeks, the morphological appearance of cells was evaluated. The results are shown in FIG. 7: panel A MK coverslip of MK+H3-GFP coculture, panel B H3-GFP coverslip of MK+H3-GFP coculture, panel C MK coverslip of MK alone, and panel D H3-GFP coverslip of H3-GFP. Comparing panel A and panel C, panel B and panel D, it is shown that co-culture of two coverslip cells in the same tissue culture dish induces the differentiation of MK cells (appearance of new cell morphology with thin long dark cells), promotes the growth, but not the differentiation of H3-GFP.

Similar experiment was performed when hIL6-secreting H3 cells are included in the culture. The results are shown in FIG. 8:

panel A MK coverslip of MK+H3-GFP-hIL6 coculture, panel B H3-GFP-hIL6 coverslip of MK+H3-GFP-hIL6 coculture, panel C MK coverslip of MK alone, and panel D H3-GFP-hIL6 coverslip of H3-GFP alone. Comparing panel A and panel C, panel B and panel D of this figure, and panels A of FIGS. 7 and 8, it is shown that hIL6 secreted from H3 prevents the differentiation of MK cells (no appearance of new cell morphology). It has no obvious differentiation effect on H3.

Experiment was performed when hCNTF-secreting H3 are included in the culture as shown in FIG. 9:

panel A MK coverslip of MK+H3-LC coculture, panel B H3-LC coverslip of MK+H3-LC coculture, panel C MK coverslip of MK alone, and panel D H3-LC coverslip of H3-LC alone. Comparing panel A and panel C, panel B and panel D of this figure, and panels A of FIGS. 7 and 8 and 9, it is shown that hCNTF secreting H3 does not prevent the differentiation of MK cells (appearance of new cell morphology). It promotes the growth, but not the differentiation of H3.

Thus, the influence of cytokines on the fate of keratinocytic stem cells, i.e., growth promoting vs. survival, proliferation vs. differentiation, is cell-mediated.

EXAMPLE 5

Cytokine-Secreting, Doxycycline-Regulatable Mouse Keratinocytic Stem Cells Influences the Differentiation of Human Keratinocytes Besides mouse MK cells, human keratinocytes (designated Sk) were tested similarly in collaboration with B. Peault in Paris. The Sk was obtained from a legal abortion with the written consent. The results are shown in FIGS. 10-12.

FIG. 10 shows:

panel A Sk coverslip of Sk+H3-GFP coculture, panel B H3-GFP coverslip of Sk+H3-GFP coculture, panel C Sk coverslip of Sk alone, and panel D H3-GFP coverslip of H3-GFP. Comparing panel A and panel C, panel B and panel D, it is shown that co-culture of two coverslip cells in the same tissue culture dish induces the differentiation of Sk cells (appearance of new cell morphology with thin long dark cells). It promotes the growth, but not the differentiation of H3-GFP.

The experiment was performed when hIL6 secreting H3 are included in the culture as shown in FIG. 11:

panel A Sk coverslip of Sk+H3-GFP-hIL6 coculture, panel B H3-GFP-hIL6 coverslip of Sk+H3-GFP-hIL6 coculture, panel C Sk coverslip of Sk alone, and panel D H3-GFP-hIL6 coverslip of H3-GFP alone. Comparing panel A and panel C, panel B and panel D of this figure, and panels A of FIGS. 11 and 10, it is shown that hIL6 secreting H3 cells prevent the differentiation of Sk cells (no appearance of new cell morphology), and provide no obvious effect on self.

The experiment was also performed when hCNTF-secreting H3 cells are included in the culture as shown in FIG. 12:

panel A Sk coverslip of Sk+H3-LC coculture, panel B H3-LC coverslip of Sk+H3-LC coculture, panel C Sk coverslip of Sk alone, and panel D H3-LC coverslip of H3-LC alone. Comparing panel A and panel C, panel B and panel D of this figure, and panels A of FIGS. 10-12, it is shown that hCNTF secreting H3 cells do not prevent the differentiation of Sk cells (appearance of new cell morphology). They promote their own growth and apoptosis.

In addition, a control experiment was performed to test the specific effect of doxycycline-regulatable keratinocytic stem cells by replacing them with MK cells. The results are shown in FIG. 13:

panel A Sk coverslip of Sk+MK coculture, panel B MK coverslip of Sk+MK coculture, panel C Sk coverslip of Sk alone, and panel D MK coverslip of MK alone. Comparing panel A and panel C, panel B and panel D of this figure, it is shown that co-culture of two coverslips containing MK cells, Sk cells, respectively, in the same tissue culture dish does not have any effect on either cell types.

The data are interpreted as follow: Cytokine-engineered stem cells affect, specifically, the behaviour of self and keratinocytic stem/precursor cells of mouse and human origins, in vitro, by the combination of the following mechanisms: growth promoting, survival, and/or differentiation mechanisms.

(1) From therapeutical point of view, during the skin injuring or wound healing process, the application of keratinocytic stem cells (H3) in situ can induce the native stem/precursor cells (such as MK, Sk) of the host (sister, external) to differentiate into mature keratinocytes. hIL6 secreting-keratinocytic stem cells (H3hIL6) can induce the proliferation and survival of such native stem/precursor cells (such as MK, Sk) of the host (sister, external) and prevent the differentiation of such cells of the host. Thus it can contribute to the wound healing process.

(2) hCNTF secreting-keratinocytic stem cells (H3LC) can induce the rapid cell division of self and native stem/precursor cells (such as MK, Sk) of the host (sister, external). However, it induces also apoptosis.

EXAMPLE 6

Doxycycline Regulatable Tracheal Epithelial Stem/Precursor Cells can Induce Cell Fusion when Co-Culturing The co-culture experiment is performed using MK cells and tracheal epithelial stem/precursor cells (CFTR positive, surfactant [SFII] weak positive, ciliar negative, designated L14), and tracheal stem/precursor cells transgenic with cytokine, such as L14hIL3, L14LC. With different combinations, the coculture of L14 hIL3+X-cells causes cell fusion, as demonstrated by membrane fusion forming pancake-like clusters. It is due to the fact that L14hIL3 cells produce surfactants, a group of phospholipid substances. Similarly substance for cell fusion are commercially available, i.e., lipofectamin (Life Science, Gibco), PEI, or transfection reagents from Qiagen.

EXAMPLE 7 hIL3-Secreting, Doxycycline-Regulatable Mouse Tracheal Epithelial Stem Cells Inhibits the Differentiation of Human Lung Cells An experiment to test the effect of mouse tracheal epithelial stem cells on human lung cells (designated Lg) was performed in collaboration with B. Peault in Paris. The Lg was obtained from a legal abortion with the written consent. Lg, L14, L14hIL3 were seeded onto coverslips separately and two types of cells were co-cultured in the same petric dish for 3 weeks. The results are shown in FIGS. 14-15.

Figure 14:
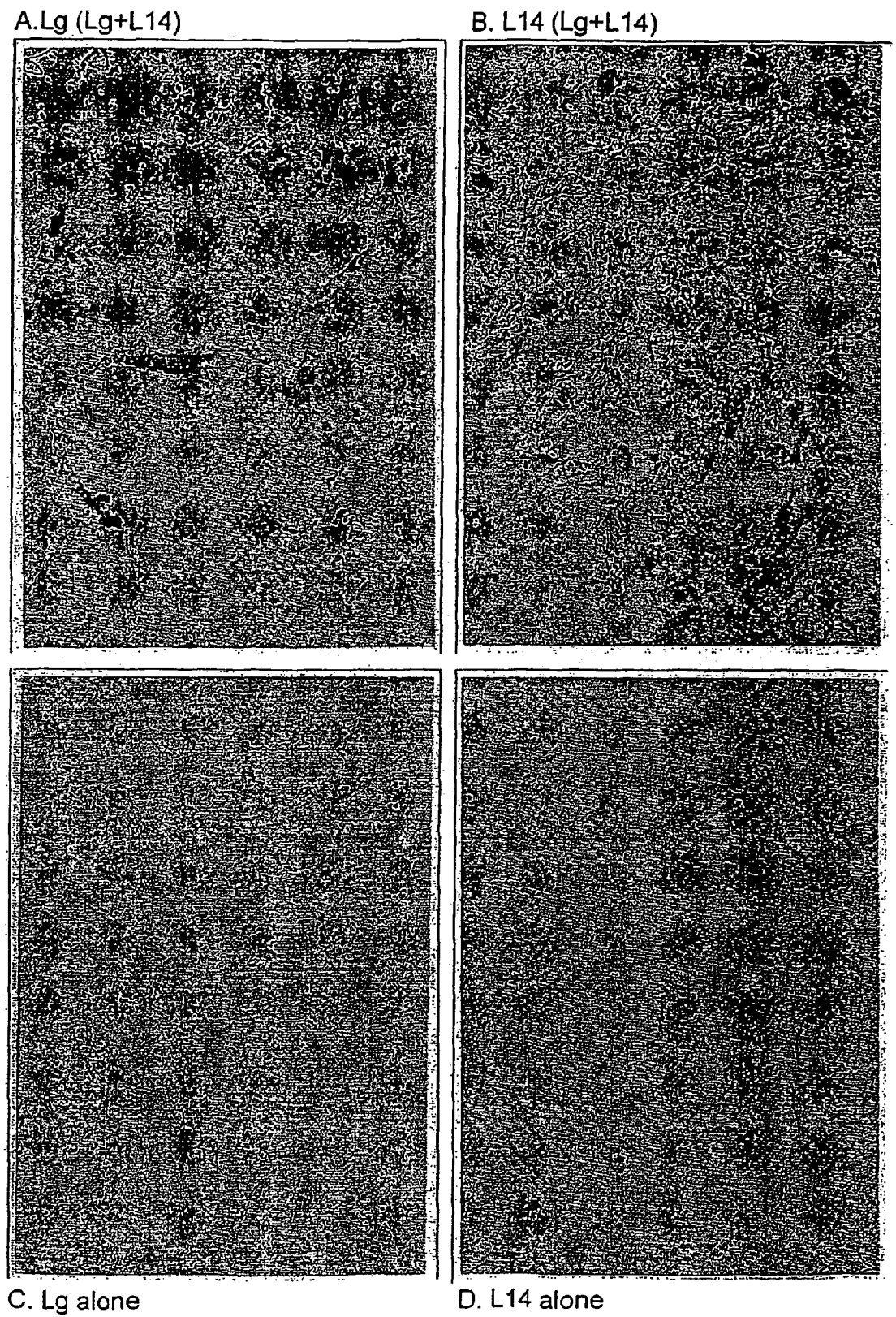

In FIG. 14, it shows panel A Lg coverslip of Lg+L14 coculture, panel B L14 coverslip of Lg+L14 coculture, panel C Lg coverslip of Lg alone, and panel D L14 coverslip of L14 alone. Comparing panel A and panel C, panel B and panel D, it is shown that co-culture of two coverslip in the same tissue culture dish induces the differentiation of Sk cells and L14 cells (appearance of new cell morphology).

The experiment was also performed when hIL3 secreting L14 cells were included in the culture as shown in FIG. 15:

panel A Lg coverslip of Lg+L14-hIL3 coculture, panel B L14-hIL3 coverslip of Lg+L14-hIL3 coculture, panel C Lg coverslip of Lg alone, and panel D L14-hIL3 coverslip of L14-hIL3 alone. Comparing panel A and panel C, panel B and panel D of this figure, and panels A, B of FIGS. 14 and 15, it is shown that hIL3 secreting L14 cells prevent the differentiation of Lg and L14-hIL3 cells (no appearance of new morphology).

The application of tracheal epithelial stem/precursor cells will be to use these cells as a tool to change the specificities of existing conditional immortalized stem cells (to make it better) in events such as trans-lineage (airway to neuron, skin, muscle, liver, etc) commitment, trans-species commitment (mouse to human), specific somatic modification such as tet-off (doxycycline turn off) to tet-on (doxycycline turn on) using either classical genetic manipulation methods, molecular or cellular breeding. The application of the direct end-differentiation products of airway stem cells (surfactant) can be for treatment of lung injury, fighting against infection such as pseudomonas infection, or film of phospholipids for industrial purposes.

The further application of doxycycline regulatable airway stem cells is to be used as feeder cells to promote or to inhibit the growth of primary human airway or nasal epithelial cells from the biopsy of Cystic Fibrosis (CF) patients. Conventionally, collagen sheet culture is used to grow such primary human cells for measuring chloride channels of the CFTR. However, insufficient quantity of cells is a handicap to such a diagnostic test. Doxycycline regulatable airway epithelial stem cells can promote such cell growing to sufficient amount allowing accurate diagnosis and to screen potential therapeutic drugs for CF patients.

EXAMPLE 8

Cytokine-Containing Keratinocytic Stem Cells and Tracheal Epithelial Stem Cells Secrete Cytokines Known to Support the Growth of Hematopoietic Stem Cells (HSC)

Using hIL3, hIL6, flk2/flt3Ligand to support the growth of HSC for several weeks in culture, and in comparing to that of stroma cell lines in supporting HSC, has been performed. In the literature there are many published data showing that hIL3, hIL6, flk2/flt3Ligand are essential to support the growth of HSC. These data show that these cytokines are essential in maintaining HSC in culture, and in increasing the transduction efficiency of retroviruses into HSC in the two chamber culture system where the experiments were performed and described in the literature.

Keratinocytic stem cell lines and tracheal epithelial stem cell lines were established from CMV-tTAxtetoCMVm-SV40Tag double transgenic mice (from H. Bujard and S. Efrat). Glial stem cell lines were established from tk-rtTAx tetoCMVm-SV40Tag double transgenic mice (from H. Bujard and S. Efrat).

EXAMPLE 9

Stem Cells are Supported by Cytokine-Containing Transgenic Stem Cells: in Vivo Using Immunoincompetent Mice (Nu/Nu Mice or Scid-NOD Mice)

It is for the purpose of somatic delivery of growth factors essential for maintenance of human hematopoietic stem cells (HSC) in recipient hosts. The cytokines constructed shown to be functional for HSC are hIL3, hIL6, and flk2/flt3Ligand, and thus are used further for in vivo experiments (below).

Teto-hIL6, teto-hIL3 containing transgenic keratinocytic and tracheal epithelial stem cells derived from CMV-tTA×teto-CMVm-SV40Tag double transgenic mice were pre-cultured on DED (denuded dermis from human cosmetic operation) or DET (denuded trachea) and implanted subcutaneously (flip-in) into immunoincompetent mice (nude mice or scid-NOD mice).

Figure 1:
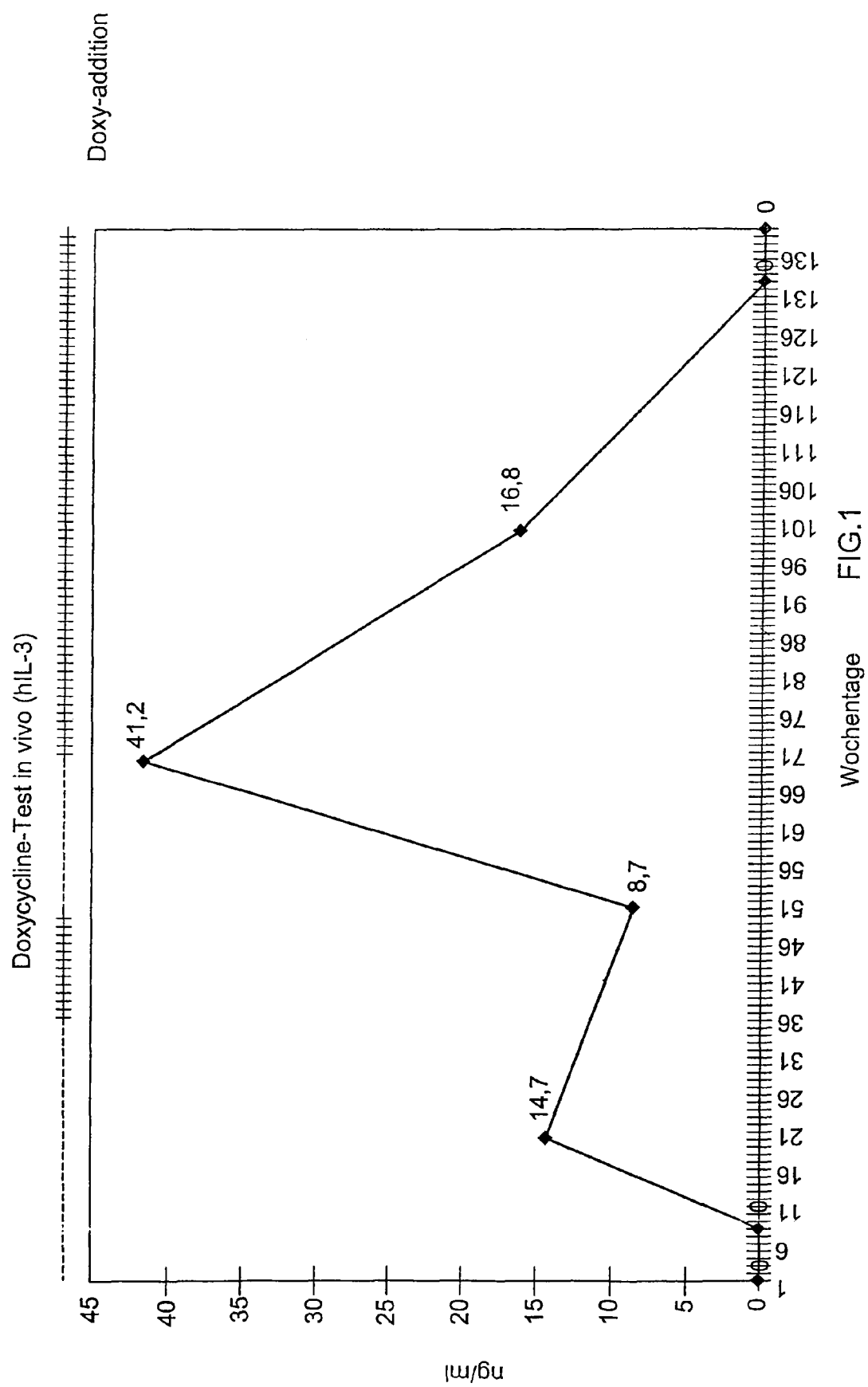
FIG. 1 shows the appearance of hIL-3, depending on the addition/removal of doxycycline in vivo.

Blood samples from such nude mice were collected from a tail vein of mice periodically. Sera were separated from blood clots. ELISA tests were performed on serum samples collected. After cytokines were demonstrated to appear in blood, such mice ingested doxycycline (200 μm/ml) included in the drinking water and blood collected at the time points indicated. As indicated in FIGS. 1 (hIL3) and 2 (hIL-6), hIL3 and hIL6 are shown to appear in the blood reaching a significant amount (14.7 pg/ml for hIL3, 15.9 pg/ml for hIL6), and they were decreased when doxycycline was included in the drinking water. Upon removal of doxycycline, hIL3 and hIL6 were shown to increase to higher levels again (41.2 pg/ml for hIL3, and 14.5 pg/ml for hIL6). Upon reingestion of doxycycline, the levels of cytokines were shown to decrease to zero. Similar data were obtained when scid-NOD mice were used as hosts.

Figure 2:
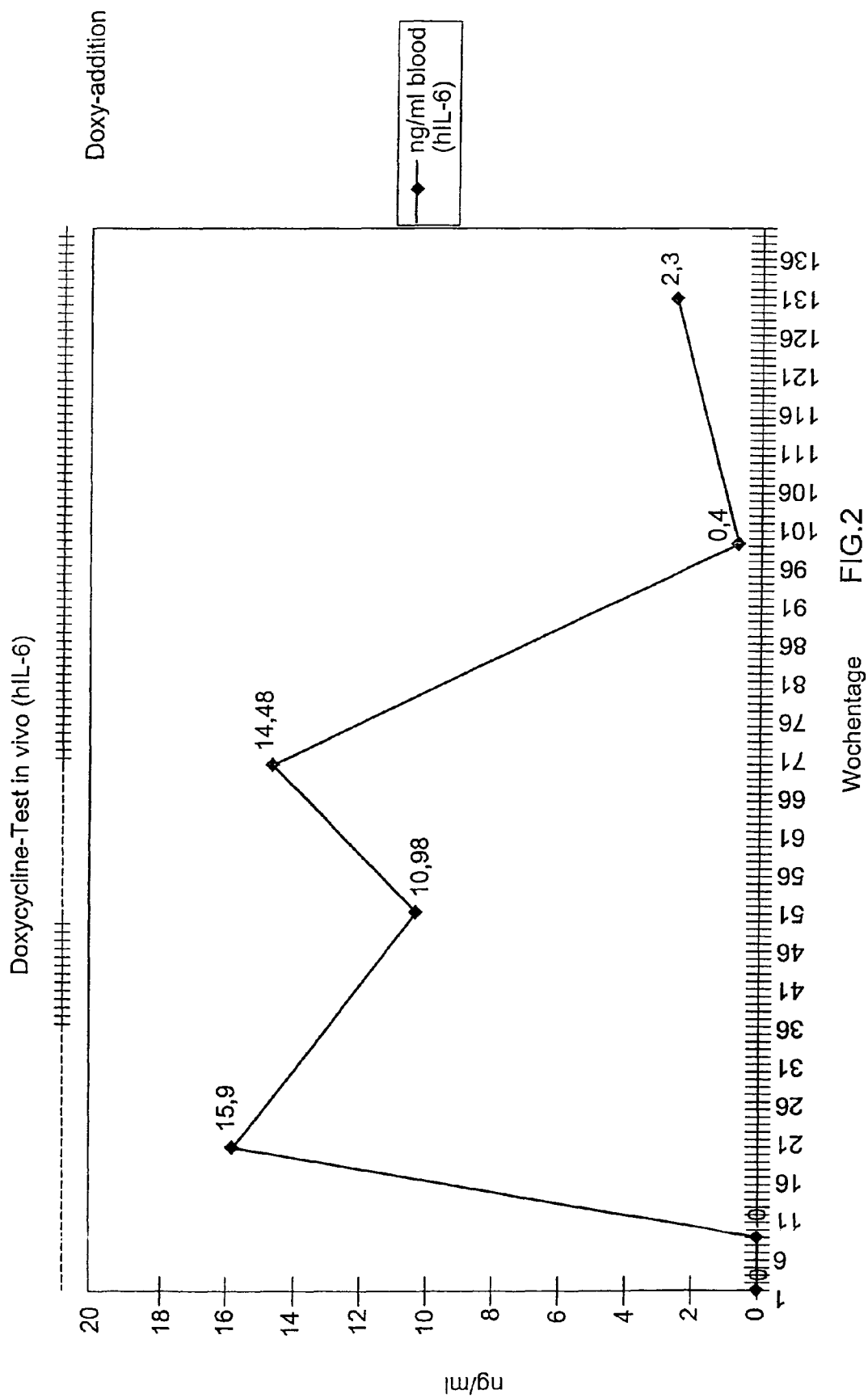
FIG. 2 shows the appearance of hIL-6 depending on the addition/removal of doxycycline in vivo (nude mice).

The mice survive over the 5-6 months of experiment without any sign of illness due to the implantation of engineered mouse stem cells delivering human cytokines. The pattern can be cyclic. Thus, in immuno-incompetent mice, it was shown that the secretion of cytokines such as hIL3 and hIL6 into the blood stream is regulated by doxycycline in the drinking water. Similar experiments were performed with pD12YCVJC-long-CNTF (FIG. 2a in nude mice, FIG. 2b in nude and scid-NOD mice) and it was shown that secretion of CNTF is regulated by doxycycline in the drinking water.

In summary, the above protocol of somatic engineering of immuno-incompetent mice with regulatable delivery of growth factors has been tested and shown to be deliverable to high titers in immuno-incompetent mice. The growth of transgenic keratinocytic stem cells and tracheal epithelial cells, and the delivery of cytokines are shown to be subjected to the regulation of doxycycline (in culture of some cells, such as HETA cells but not other cells, such as a hIL6-containing keratinocytic cell line, when doxycycline is included in the medium); and in vivo when included in the drinking water.

The principle of this protocol can also apply to the support of the growth of stem cells of any kind, such as neural and glial stem cells, in immuno-incompetent mice, as a novel diagnostic tool for evaluating the preclinical and clinical protocols.

Following 6 months in vivo, L14-hIL3 cells on cell matrix (DED, TED), increase cell mass drastically. Cell mess is formed by sponge-like, white fused tissue, similar to lung structure with emulsion of surfactant. The structure suggests the in vivo environment promotes the maturation process of L14-hIL3 airway precursor cells to surfactant positive, differentiated cells.

EXAMPLE 10

Establishment and Commercialization of SCID-NOD-Hu Systems as Diagnostics for Growth and Evaluation of Self-Renewal Property of Human Neuronal and Glial Stem Cells, Clinical Protocol and for Drug Targeting The keratinocytic stem cell line and tracheal epithelial stem cell line derived from CMV-tTA×tetoCMVm-SV40Tag double transgenic mice, and the neural-glial precursor cell lines derived from tk-rtTA×tetoCMVm-SV40Tag double transgenic mice are used in this type of experiment. These cell lines are inserted with cytokine constructs for the somatic delivery of neurotropic factors essential for the survival and maintenance of human adult brain stem cells in recipient hosts. The cytokines constructed are pD12YCVJC-driven GDNF and CNTF. The transgenic tracheal epithelial stem cells are pre-cultured on DED (denuded dermis) or DET (denuded trachea) or DEB (denuded brain) and implanted subcutaneously (flip-in) (in the head region) into nude or scid-NOD mice. The growth of transgenic keratinocytic stem cells and epithelial tracheal cells, neural-glial precursor cells, and the delivery of cytokines have been shown to be subjected to the regulation of doxycycline in culture and in vivo when included in the drinking water. The mice survive over the months of experiment without any sign of illness due to the implantation of engineered mouse cells delivering human cytokines. It was shown that the principle of the protocol works similarly in the immuno-competent mice for human neurotrophic factors. In addition, in vivo (nude mice), H3LC cells (H3 cells transgenic with long JCVpCNTF) induce the production of erythrocytes as shown by increasing hematocrite 3 fold over the control mice. They may become a drug to treat anemia.

When doxycycline is withdrawn from cultured neural-glial precursor cell line derived from tk-rtTA×tetoCMVm-SV40Tag double transgenic mice (designated Hirn-rtTA), these cells are induced to differentiate to mature type 2 astrocytes, neurons and oligodendrocytes and to secrete myeline in vitro and in vivo. In vitro, the presence of cell-based secreting cytokines such as hIL6, hIL3, CNTF is required. Scale up the production of myeline from culturing such cell line may become a therapeutic drug for repairment lost of myeline during nerve injuring and/or neuronal diseases. This neural-glial precursor cell line itself secretes neurotropic factors. Thus it has the application for neuroregeneration.

EXAMPLE 11

Protocol for Construction of pD12JCVPLong-CNTF Plasmid

Similar strategy and construction protocols held for pD12JCVPLong-GDNF, pD12JCVPshort-CNTF, pD12JCVPshort-GDNF.

1. pD12JCVPLong vector (from E. Beck and J. Henson) was linearized upon NsiI restriction enzyme.
2. The sticky ends of the vector were filled using Klenow fragments of *E. coli* polymerase I.
3. Digestion of the linearized pD12JCVPLong vector with restriction enzyme XhoI.
4. After digestion, the DNA sample was subjected to gel electrophoresis in 0.8% preparative agarose gel to obtain ca. 6.3 kb DNA fragment (pDl2JCVPLong×NsiI/XhoI).
5. pBS-hCNTF-079 vector (from E. Beck) was linearized with restriction enzyme NotI.

6. The termini of the linearized pBS-hCNTF-079 vector was filled with Klenow fragment of *E. coli* DNA polymerase I in order to obtain the blunt-end.
7. The linearized and blunt-ended (pBS-hCNTF-079×NotI) was digested with SahI.
8. After digestion, the DNA sample was subjected to gel electrophoresis in 0.8% preparative agarose gel and the 2469 bp DNA fragment containing CNTF gene was isolated.
9. The blunt- and sticky ended (CNTF×NotI/SahI) fragment (from step 8) was ligated with complementary blunt- and sticky-ended (pD12JCVPLong×NsiI/XhoI) (from step 4) vector.
10. VXL1-blue competent bacteria *E. coli* was transformed with DNA (from step 9), and ampicillin resistant clones were selected, and characterized to be correct.

EXAMPLE 12

Protocol for Construction of pRetro-off-E6E7 Plasmid 1. pLXSNE6E7 vector (from D. Galloway) was linearized upon EcoRI restriction enzyme digestion.
2. The sticky ends of the vector was filled using Klenow fragments of *E. coli* DNA polymerase I.
3. The termini of the linearized pLXSNE6E7 was ligated with synthetic-adaptor (XhoI-NotI-BglII) purchased from Roth, Karlsruhe.
4. The newly adapted-[pLXSNE6E7×NotI/BamHI] (step 3) was digested with NotI and BamHI.
5. After digestion, the DNA sample was subjected to gel electrophoresis in 1% preparative agarose gel to obtain ca. 830 bp fragment of [E6E7×Not/BamHI].
6. pRetro-off vector was digested with NotI and BamHI.
7. The fragment of [E6E7×NotI/BamHI] was then inserted into the [pRetro-off vector×NotI/BamHI] (step 6).
8. XL1-blue competent bacteria *E. coli* were transformed with the construct from step 7. Ampicillin resistant clones were selected and characterized to be correct.

EXAMPLE 13

Protocol-2 for Construction of pRetro-off-U19tsA58 Plasmid 1. pZipNEOSV(x) vector (from P. Jat) was digested with BamHI restriction enzyme.
2. After digestion, the DNA sample was electrophoresed in 0.8% preparative agarose gel to obtain ca 2.6 kb DNA fragment (U19tsA58×BamHI).
3. pRetro-off vector was linearized with restriction enzyme BamHI.
4. The terminal of the linearized pRetro-OFF vector was dephosphoried with Shrimp Alkaline Phosphatase (USB) from Amersham.
5. The fragment of (U19tsA58×BamHI) (from step 2) was then inserted into the (pRetro-off vector×BamHI) (from step 4).
6. The XL1-blue competent bacteria *E. coli* was transformed with DNA (from step 5), and ampicillin resistant clones were selected, and characterized to be correct.
7. A similar protocol yields the respective pRetro-tet-on-x (including pRetro-tet-ART-x, from H. Blau) derived vectors, other pRetro-tet-off-x (including pLP-TRE2 and pLP-RevTRE, Clontechniques) derived vectors, adeno5 viral derived (adeno5-x, from R. Gerald), and lenti-viral-x vectors, x=U19tsA58, SV40Tag, E6/E7, Bcl2, T2, and TGFbeta3.

EXAMPLE 14

Protocol-3 for Construction of pRetro-off-(tTA deleted)-E6/E7 Plasmid 1. pRetro-off-E6/E7 vector was digested with BamHI and EcoRI restriction enzymes to delete DNA motif coding for tTA.
2. After digestion, the DNA sample was electrophoresed in 0.8% preparative agarose gel to obtain ca. 6.3 kb DNA fragment (pRetro-off-E6/E7×BamHI-EcoRI).
3. pRetro-off-E6/E7×BamHI-EcoRI vector was blunt-ended with Klenow fragment of pol.I and was ligased with enzyme Ligase T7 (Bohringer-Mannheim).
4. XL1-blue competent bacteria *E. coli* was transformed with DNA (from step 3), and ampicillin resistant clones were selected, and characterized to be correct.

EXAMPLE 15

Protocol for the Construction of pUHD-Transactivator Vectors

A. Transactivator, pUHD15.1-pCMV-tTA-β-gal-neomycin Plasmid:
1. pUHD15.1 (from H. Bujard) was linearized using BamHI restriction enzyme.
2. 5'-end was dephosphorized using phosphatase, and the DNA sample was subjected to gel electrophoresis in 1% preparative agarose gel to obtain ca. 7255 bp fragment of (pUHD15.1BamHI).
3. IRES-βgeo fragment which contains lacZ+neo (Ca 3050 bp)) was obtained from another plasmid (ptetotsA58IRESβgeo) (from H. Schoeler) using BamHI restriction enzyme digestion.
4. After digestion, the DNA sample was subjected to gel electrophoresis in 1% preparative agarose gel to obtain ca. 3050 bp fragment of (IRES-βgeoBamHI).
5. The fragment of (IRES-βgeoBamHI) (step 4) was then inserted into the (pUHD15.1BamHI) (step 2).
6. XL1-blue competent bacteria *E. coli* were transformed with the construct from step 5. Ampicillin resistant clones were selected and characterized to be correct.

EXAMPLE 16

Protocol for the Construction of pUHD-Responder Vectors

B. Responder pUHD10.3 Cytokine Plasmids:
1. The multiple cloning site (MCS) of responder pUHD10.3 (from H. Bujard) was linearized using EcoRI and SacII (for hIL6), or EcoRI and BamHI (for hIL3), or EcoRI and XbaI (for TGFβ3) or Eco RI (for hflt3 ligand exon 6) restriction enzymes.
2. After digestion, the individual DNA sample was subjected to gel electrophoresis in 1% preparative agarose gel to obtain ca. 3150 bp fragment of DNA.
3. Fragments of cDNA coding for hIL6 (EcoRI-SacII), hIL3 (EcoRI-BamHI), TGFβ3 (EcoRI-XbaI) hflt3 ligand exon 6 (Eco RI) were obtained from the original supplier (A.

Bernad, Genetic Institute, ATCC, Immunex), and individual restriction enzyme digested as indicated in the original publications.
4. After digestion, the DNA sample was subjected to gel electrophoresis in 1% preparative agarose gel to obtain ca. 600 bp fragment of hIL6 (EcoRI-SacII), ca. 475 bp fragment of hIL3 (EcoRI-BamHI). and ca. 1233 bp fragment of TGFβ3 (EcoRI-XbaI), and ca. 1 000 bp fragment of hflt3 ligand exon 6 (Eco RI).
5. The fragment coding for the respective cytokine gene (step 4) was then inserted into the responder pUHD10.3 EcoRI-SacII (for hIL6), or EcoRI-BamHI (for hIL3), or EcoRI-XbaI (for TGFβ3) or Eco RI (for hflt3 ligand exon 6) (step 2).
6. XL1-blue competent bacteria E. coli were transformed with the construct from step 5. Ampicillin resistant clones were selected and characterized to be correct.
7. A similar protocol yields also for hNGF (nerve growth factor), CNTF, GNDF, hIL2, hIL7 (from W. Uckert), hGMCSF, and hIL4 (from NGVL, Univ. Michigan).

EXAMPLE 17

Protocol for Construction of pUHD10.3-hflt3 Ligand exon 6 Plasmid 1. pHuflt3l-exon6 (for human flt3 Ligand exon 6) vector was digested with EcoRI restriction enzyme.
2. After digestion, the DNA sample was electrophoresed in 0.8% preparative agarose gel to obtain ca. 1 kb DNA fragment (hflt3 Ligand exon 6×EcoRI).
3. pUHD 10.3 vector was linearized with restriction enzyme EcoRI (pUHD 10.3×EcoRI).
4. The terminal of the linearized pUHD10.3 vector was dephosphoried with Shrimp Alkaline Phosphatase (USB) from Amersham to give ca. 3150 bp fragment.
5. The fragment of (hflt3 Ligand exon 6×EcoRI) (from step 2) was then inserted into the (pUHD10.3 vector×EcoRI) (from step 4).
6. XL1-blue competent bacteria E. coli was transformed with DNA (from step 5), and ampicillin resistant clones were selected, and characterized to be correct.

EXAMPLE 18

Protocol for Construction of pAdeno5-TGFb3 Plasmid 1. pUHD10.3 TGFbeta 3 vector was digested with EcoRI and BamHI restriction enzymes.
2. After digestion, the DNA sample was electrophoresed in 0.8% preparative agarose gel to obtain ca. 1.2 kb DNA fragment (TGFbeta 3×EcoRI-BamHI).
3. pAdeno 5 (pACCMVpLpA) vector (from R. Gerald*) was linearized with restriction enzyme EcoRI and BamHI (pACCMVpLpA×EcoRI-BamHI).
   *A map is not included, since R. Gerald did not submit the vector sequence to the GeneBank. However, he published it in "DNA cloning—a practical approach: mammalian systems" pp. 285-307, eds. B D Hames and D. Glover, Oxford Univ. Press, 1995. He also provided a restriction map of this vector.
4. The terminal of the linearized pACCMVpLpA vector was dephosphoried with Shrimp Alkaline Phosphatase (USB) from Amersham.
5. The fragment of 1.2 Kb TGFbeta 3×EcoRI-BamHI (from step 2) was then inserted into the (pACCMVpLpA×EcoRI-BamHI) (from step 4).
6. XL1-blue competent bacteria E. coli was transformed with DNA (from step 5), and ampicillin resistant clones were selected, and characterized to be correct.

EXAMPLE 19

Protocol for Construction of pAdeno5-T2 Plasmid 1. pBabe puro T2 mutant beta-catenin vector (from F. Watt, pBabe puro T2 mutant beta-catenin vector was described in A. Zhu and F. Watt, Development 126: 2285-2298, 1999. A restriction map is provided.) was digested with BamHI restriction enzyme.
2. After digestion, the DNA sample was electrophoresed in 0.8% preparative agarose gel to obtain ca. 2.2 kb DNA fragment (T2×BamHI).
3. pAdeno 5 (pACCMVpLpA) vector (from R. Gerald, a map is not included, since R. Gerald did not submit the vector sequence to the GeneBank. However, he published it in "DNA cloning—a practical approach: mammalian systems" pp. 285-307, eds. B D Hames and D. Glover, Oxford Univ. Press, 1995. He also provided a restriction map of this vector.) was linearized with restriction enzyme BamHI (pACCMVpLpA×BamHI).
4. The terminal of the linearized pACCMVpLpA vector was dephosporied with Shrimp Alkaline Phosphatase (USB) from Amersham.
5. The fragment of 2.2 Kb T2×BamHI (from step 2) was then inserted into the (pACCMVpLpA×BamHI) (from step 4).
6. XL1-blue competent bacteria E. coli was transformed with DNA (from step 5), and ampicillin resistant clones were selected, and characterized to be correct.

EXAMPLE 20

Protocol for Construction of pAdeno5-U19tsA58 Plasmid 1. pRetro-off-U19tsA58 vector (see Example 13, Protocol-2) was digested with BamHI restriction enzyme.
2. After digestion, the DNA sample was electrophoresed in 0.8% preparative agarose gel to obtain ca. 2.5 kb DNA fragment (U19tsA58×BamHI).
3. pAdeno 5 (pACCMVpLpA) vector (from R. Gerald, A map is not included, since R. Gerald did not submit the vector sequence to the GeneBank. However, he published it in "DNA cloning—a practical approach: mammalian systems" pp. 285-307, eds. B D Hames and D. Glover, Oxford Univ. Press, 1995. He also provided a restriction map of this vector.) was linearized with restriction enzyme BamHI (pACCMVpLpA×BamHI).
4. The terminal of the linearized pACCMVpLpA vector was dephosphoried with Shrimp Alkaline Phosphatase (USB) from Amersham.
5. The fragment of 2.5 Kb U19tsA58×BamHI (from step 2) was then inserted into the (pACCMVpLpA×BamHI) (from step 4).
6. XL1-blue competent bacteria E. coli was transformed with DNA (from step 5), and ampicillin resistant clones were selected, and characterized to be correct.

EXAMPLE 21

Protocol for Construction of pRetro-off-T2-Catenin Plasmid 1. pBabe puro T2 mutant beta-catenin vector (from F. Watt, pBabe puro T2 mutant beta-catenin vector was described in A. Zhu and F. Watt, Development 126: 2285-2298, 1999. A restriction map is provided.) was digested with BamHI restriction enzymes.
2. After digestion, the DNA sample was electrophoresed in 0.8% preparative agarose gel to obtain ca. 2.2 kb DNA fragment (T2×BamHI).
3. pRetro-off vector was linearized with restriction enzyme BamHI (pRetro-off×BamHI).
4. The terminal of the linearized pRetro-off vector was dephosphoried with Shrimp Alkaline Phosphatase (USB) from Amersham.
5. The fragment of 2.2 Kb T2×BamHI (from step 2) was then inserted into the pRetro-off×BamHI (from step 4).
6. XL1-blue competent bacteria *E. coli* was transformed with DNA (from step 5), and ampicillin resistant clones were selected, and characterized to be correct.

The vector systems Tet™ and RevTet™ (Clontechniques, April 2000, p. 10) yield similar results.

EXAMPLE 22

Protocol for Construction of pRetro-off-[tTA deleted] E6/E7 Plasmid 1. pRetro-off-E6/E7 vector (see Example 12) was digested with BamHI and EcoRI restriction enzymes to delete DNA motif coding for tTA.
2. After digestion, the DNA sample was electrophoresed in 0.8% preparative agarose gel to obtain ca. 6.3 kb DNA fragment (pRetro-off-E6/E7×BamHI-EcoRI).
3. pRetro-off-E6/E7×BamHI-EcoRI vector was blunt-ended with Klenow fragment of pol.I and was ligased with enzyme Ligase T7 (Bohringer-Mannheim).
4. XL1-blue competent bacteria *E. coli* was transformed with DNA (from step 3), and ampicillin resistant clones were selected, and characterized to be correct.

The vector systems Tet™ and RevTet™ (Clontechniques, April 2000, p. 10) yield similar results.

EXAMPLE 23

Protocol for Construction of pRetro-off-Bcl2 Plasmid 1. pPBS-Bcl2 vector (from N. McCarkthy, pPBS-Bcl2 was provided by N. McCarkthy. A restriction map and the complete sequences are provided.) was digested with EcoRI restriction enzyme.
2. After digestion, the DNA sample was electrophoresed in 0.8% preparative agarose gel to obtain ca. 1.0 kb DNA fragment (Bcl2×EcoRI).
3. pRetro-off vector was linearized with restriction enzyme NotI. 5 (pRetro-off×NotI), and filled with Klenow fragment of pol.I.
4. The terminal of the linearized pRetro-off vector was dephosphoried with Shrimp Alkaline Phosphatase (USB) from Amersham.
5. The fragment of 1.0 Kb Bcl2×EcoRI (from step 2) was then inserted into the pRetro-off×NotI (from step 4).
6. XL1-blue competent bacteria *E. coli* was transformed with DNA (from step 5), and ampicillin resistant clones were selected, and characterized to be correct.

The vector systems Tet™ and RevTet™ (Clontechniques, April 2000, p. 10) yield similar results.

The invention claimed is:

1. A method for growing stem cells comprising the steps of providing a stem cell and a supporter cell selected from the group consisting of keratinocytic stem cells, lung and tracheal epithelial cells, bone marrow and hepatic stroma cells, neural-glial precursor cells, tissue cells, and "spore"-like stem cells,
the supporter cell being genetically modified by a vector comprising (i) a gene for interleukines, protooncogenes, oncogenes, cell cycle control genes, signal transduction genes, and/or cell based growth factors and (ii) a tetracycline regulatable expression system, in order to provide externally regulatable interactions between the supporter cell and the stem cell,
and
applying an external signal for starting or stopping the interactions.

2. The method of claim 1 wherein the interactions are based on secretion or display of substances by the supporter cell.

3. The method of claim 1 wherein the interactions are based on secretion or display of substances by the supporter cell and the secretion or display of substances is under control of the expression system promoter.

4. The method of claim 1, wherein the supporter cells form a micro-environment.

5. The method of claim 1, wherein the supporter cells are secreting or displaying cell based growth factors and/or interleukines.

6. A supporter cell for use in the method of claim 1, the supporter cell being selected from the group consisting of keratinocytic stem cells, lung and tracheal epithelial cells, bone marrow and hepatic stroma cells, neural-glial precursor cells, primary tissue cells, and "spore"-like stem cells,
the supporter cell being genetically modified by a vector comprising (i) a gene for interleukines, protooncogenes, oncogenes, cell cycle control genes, signal transduction genes, and/or cell based growth factors and (ii) a tetracycline regulatable expression system, in order to provide externally regulatable interactions between the supporter cell and the stem cell and,
the supporter cell being genetically modified in order to provide a regulatable secretion and/or a display of substances of the supporter cell.

7. A supporter cell, the supporter cell being selected from the group consisting of keratinocytic stem cells, lung and tracheal epithelial cells, bone marrow and hepatic stroma cells, neural-glial precursor cells, primary tissue cells, and "spore"-like stem cells,
the supporter cell being genetically modified by a vector comprising (i) a gene for interleukines, protooncogenes, oncogenes, cell cycle control genes, signal transduction genes, and/or cell based growth factors and (ii) a regulatable expression system, in order to provide externally regulatable interactions between the supporter cell and a stem cell and,
the supporter cell being genetically modified, genetically mutated, and/or modified using molecular and cellular breeding in order to change tet-on to tet-off and vice versa, to change oncogenicity, and to change trans-lineage-commitment.

8. The supporter cell according to claim 7, wherein the change in oncogenicity is SV40Tag to E6/E7 and the change in trans-lineage-commitment is brain to skin.

9. A cell line obtainable by transforming a cell with a vector,
the cell being selected from the group consisting of keratinocytic stem cells, lung and tracheal epithelial cells, bone marrow and hepatic stroma cells, neural-glial precursor cells, primary tissue cells, and "spore"-like stem cells, and
the vector comprising (i) a gene for interleukines, protooncogenes, oncogenes, cell cycle control genes, signal transduction genes, and/or cell based growth factors and (ii) a tetracycline regulatable expression system.

* * * * *